US009192635B2

(12) United States Patent
Huang et al.

(10) Patent No.: US 9,192,635 B2
(45) Date of Patent: *Nov. 24, 2015

(54) METHOD OF TREATING DAMAGED MUCOSAL OR GASTROINTESTINAL TISSUE BY ADMINISTERING A COMPOSITION COMPRISING A MIXTURE OF POMEGRANATE AND GREEN TEA EXTRACTS AND RELEASABLY BOUND HYDROGEN PEROXIDE

(75) Inventors: Alexander L. Huang, Menlo Park, CA (US); Gin Wu, San Rafael, CA (US)

(73) Assignee: LIVELEAF, INC., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/135,125

(22) Filed: Jun. 24, 2011

(65) Prior Publication Data

US 2012/0328710 A1 Dec. 27, 2012

(51) Int. Cl.
| | |
|---|---|
| *A61K 36/00* | (2006.01) |
| *A61K 36/185* | (2006.01) |
| *A61K 36/82* | (2006.01) |
| *A61K 31/353* | (2006.01) |
| *A61K 33/40* | (2006.01) |
| *A61K 31/7024* | (2006.01) |

(52) U.S. Cl.
CPC .............. *A61K 36/00* (2013.01); *A61K 31/353* (2013.01); *A61K 33/40* (2013.01); *A61K 36/185* (2013.01); *A61K 36/82* (2013.01); *A61K 31/7024* (2013.01)

(58) Field of Classification Search
None
See application file for complete search history.

(56) References Cited

U.S. PATENT DOCUMENTS

| | | |
|---|---|---|
| 1,844,018 A | 12/1929 | Sailer |
| 1,891,149 A | 11/1931 | Elger |
| 1,965,458 A | 2/1933 | Elger |
| 3,817,835 A | 3/1969 | Neidleman |
| 3,484,248 A | 12/1969 | Nathaniel et al. |
| 3,824,184 A | 9/1970 | Hatcher et al. |
| 3,649,297 A | 3/1972 | Millin |
| 3,692,904 A | 9/1972 | Tsutsumi |
| 3,821,440 A | 6/1974 | Revee |
| 3,860,694 A | 1/1975 | Jayawant |
| 3,864,454 A | 2/1975 | Pistor et al. |
| 4,008,339 A | 2/1977 | Matsuda et al. |
| 4,072,671 A | 2/1978 | Sodini et al. |
| 4,171,280 A | 10/1979 | Maddox et al. |
| 4,435,601 A | 3/1984 | Formanek et al. |
| 4,472,302 A | 9/1984 | Karkhanis |
| 4,472,602 A | 9/1984 | Bordelon et al. |
| 4,514,334 A | 4/1985 | Mark |
| 4,623,465 A | 11/1986 | Klibanov |
| 4,829,001 A | 5/1989 | Mencke et al. |
| 4,900,671 A | 2/1990 | Pokora et al. |
| 4,966,762 A | 10/1990 | Pfeffer et al. |
| 5,008,248 A | 4/1991 | Bywater et al. |
| 5,141,611 A | 8/1992 | Ford |
| 5,208,010 A | 5/1993 | Thaler |
| 5,231,193 A | 7/1993 | Mizusawa et al. |
| 5,260,021 A | 11/1993 | Zeleznick |
| 5,296,376 A | 3/1994 | Bridges et al. |
| 5,328,706 A | 7/1994 | Endico |
| 5,389,369 A | 2/1995 | Allen |
| 5,614,501 A | 3/1997 | Richards |
| 5,653,746 A | 8/1997 | Schmitt |
| 5,661,170 A | 8/1997 | Chodosh |
| 5,700,769 A | 12/1997 | Schneider et al. |
| 5,756,090 A | 5/1998 | Allen |
| 5,824,414 A | 10/1998 | Kobayashi et al. |
| 5,834,409 A | 11/1998 | Ramachandran et al. |
| 5,839,369 A | 11/1998 | Chatterjee et al. |
| 5,879,733 A | 3/1999 | Ekanayake et al. |
| 5,891,440 A | 4/1999 | Lansky |
| 6,068,862 A | 5/2000 | Ishihara et al. |
| 6,071,541 A | 6/2000 | Murad |
| 6,080,573 A | 6/2000 | Convents et al. |
| 6,136,849 A | 10/2000 | Hoffmann et al. |
| 6,284,770 B1 | 9/2001 | Mangel et al. |
| 6,383,523 B1 | 5/2002 | Murad |
| 6,420,148 B2 | 7/2002 | Yamaguchi |
| 6,436,342 B1 | 8/2002 | Petri et al. |
| 6,444,805 B1 | 9/2002 | Sohn et al. |
| 6,537,546 B2 | 3/2003 | Echigo et al. |
| 6,551,602 B1 | 4/2003 | Barrett et al. |
| 6,630,163 B1 | 10/2003 | Murad |
| 6,642,277 B1 | 11/2003 | Howard et al. |

(Continued)

FOREIGN PATENT DOCUMENTS

| | | |
|---|---|---|
| CN | 200910167930.5 | 10/2009 |
| EP | 0390107 | 10/1990 |
| EP | 0797451 | 9/2004 |
| EP | 1736165 | 12/2006 |
| GB | 1204576 | 9/1970 |
| JM | 2000026310 | 3/1999 |
| JP | 1987126130 | 11/1995 |
| JP | H11043696 | 7/1997 |
| JP | 2005519151 | 2/2002 |
| JP | 2005533027 | 5/2002 |

(Continued)

OTHER PUBLICATIONS

Do-It-Yourself Health. Somerville, R. Ed. Time Life Books, 1997 ISBN:81-7021-858-6.*

(Continued)

*Primary Examiner* — Scarlett Goon
*Assistant Examiner* — Dale R Miller
(74) *Attorney, Agent, or Firm* — Bryan S. Boyer; Syndicated Law, PC

(57) ABSTRACT

The teachings provided herein generally relate to site-activated binding systems that selectively increase the bioactivity of phenolic compounds at target sites. More particularly, the systems taught here include a phenolic compound bound to a reactive oxygen species, wherein the phenolic compound and the reactive oxygen species react at a target area in the presence of an oxidoreductase enzyme.

6 Claims, 13 Drawing Sheets

(56) References Cited

U.S. PATENT DOCUMENTS

Figure 1A:
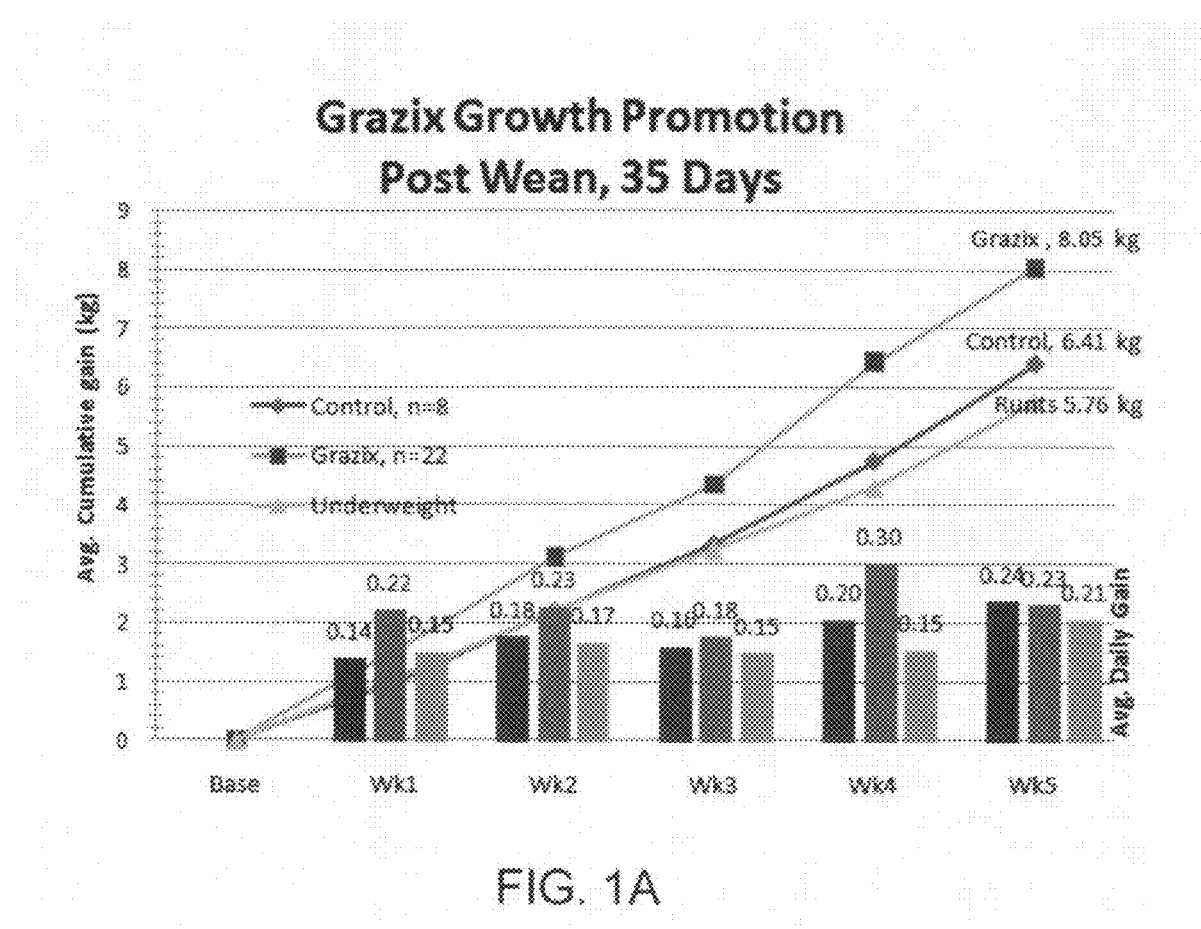

| | | | |
|---|---|---|---|
| 6,926,881 | B2 | 8/2005 | Hirose et al. |
| 7,018,660 | B2 | 3/2006 | Murad |
| 7,241,461 | B2 | 7/2007 | Myhill et al. |
| 7,297,344 | B1 | 11/2007 | Fleischer et al. |
| 7,341,744 | B1 | 3/2008 | Rozhon et al. |
| 7,504,251 | B2 | 3/2009 | Olshenitsky et al. |
| 8,067,041 | B2 | 11/2011 | Quart et al. |
| 8,716,351 | B1 * | 5/2014 | Huang et al. .................. 514/714 |
| 8,716,352 | B1 * | 5/2014 | Huang et al. .................. 514/714 |
| 8,716,353 | B1 * | 5/2014 | Huang et al. .................. 514/714 |
| 8,765,818 | B1 * | 7/2014 | Huang et al. .................. 514/714 |
| 8,772,350 | B1 * | 7/2014 | Huang et al. .................. 514/714 |
| 8,772,351 | B1 * | 7/2014 | Huang et al. .................. 514/714 |
| 8,772,352 | B1 * | 7/2014 | Huang et al. .................. 514/714 |
| 8,809,399 | B1 * | 8/2014 | Huang et al. .................. 514/714 |
| 8,822,544 | B2 * | 9/2014 | Huang et al. .................. 514/714 |
| 8,822,545 | B1 * | 9/2014 | Huang et al. .................. 514/714 |
| 8,946,304 | B2 * | 2/2015 | Huang et al. .................. 514/714 |
| 8,952,072 | B2 * | 2/2015 | Huang et al. .................. 514/714 |
| 9,023,895 | B1 * | 5/2015 | Huang et al. .................. 514/714 |
| 2001/0007762 | A1 | 7/2001 | Echigo et al. |
| 2002/0034553 | A1 | 3/2002 | Zayas |
| 2002/0041901 | A1 | 4/2002 | Murad |
| 2002/0172719 | A1 | 11/2002 | Murad |
| 2003/0078212 | A1 | 4/2003 | Li et al. |
| 2003/0228379 | A1 | 12/2003 | Shi et al. |
| 2004/0137077 | A1 | 7/2004 | Ancira et al. |
| 2004/0228831 | A1 | 11/2004 | Belinka, Jr. et al. |
| 2005/0169988 | A1 | 8/2005 | Tao et al. |
| 2006/0024339 | A1 | 2/2006 | Murad |
| 2006/0024385 | A1 | 2/2006 | Pedersen |
| 2006/0051429 | A1 | 3/2006 | Murad |
| 2006/0165812 | A1 | 7/2006 | Charron |
| 2007/0010632 | A1 | 1/2007 | Kaplan et al. |
| 2007/0110812 | A1 | 5/2007 | Xia et al. |
| 2007/0154414 | A1 | 7/2007 | Bonfiglio |
| 2007/0178055 | A1 | 8/2007 | Buch et al. |
| 2008/0003314 | A1 | 1/2008 | Ochiai et al. |
| 2008/0118602 | A1 | 5/2008 | Narayanan et al. |
| 2009/0023804 | A1 | 1/2009 | Baugh et al. |
| 2009/0048312 | A1 | 2/2009 | Greenberg et al. |
| 2009/0083885 | A1 | 3/2009 | Daniell |
| 2009/0093440 | A1 | 4/2009 | Murad |
| 2010/0055138 | A1 | 3/2010 | Margulies et al. |
| 2010/0278759 | A1 | 11/2010 | Murad |
| 2012/0136019 | A1 | 5/2012 | Boyd et al. |
| 2012/0328711 | A1 * | 12/2012 | Huang et al. .................. 424/616 |
| 2012/0329736 | A1 * | 12/2012 | Huang et al. .................... 514/25 |
| 2013/0078322 | A1 | 3/2013 | Huang et al. |
| 2014/0370118 | A1 | 12/2014 | Huang et al. |
| 2015/0010645 | A1 | 1/2015 | Huang et al. |

FOREIGN PATENT DOCUMENTS

| | | | |
|---|---|---|---|
| JP | 2004510717 | 1/2004 | |
| JP | 2007531771 | 4/2004 | |
| JP | 2006-045121 | 8/2004 | |
| JP | 2006182727 | 12/2004 | |
| JP | 2008542286 | 5/2005 | |
| JP | 2008072961 | 9/2006 | |
| WO | WO 94/03607 | 2/1994 | |
| WO | WO 00/06116 | 2/2000 | |
| WO | WO 00/61166 | 10/2000 | |
| WO | WO 2004/003607 | 2/2004 | |
| WO | WO 2005/067727 | 7/2005 | |
| WO | WO 2005/099721 | 10/2005 | |
| WO | WO 2006/038893 | 4/2006 | |
| WO | WO 2006/096778 | 11/2006 | |
| WO | WO 2007/003068 | 1/2007 | |
| WO | WO 2007003068 A1 * | 1/2007 | ............... A23K 1/14 |
| WO | WO 2010/018418 | 2/2010 | |
| WO | WO 2010/101844 | 9/2010 | |
| WO | WO 2010/138082 | 12/2010 | |
| WO | PCT/US2013/075221 | 12/2012 | |
| WO | WO 2012/178127 | 1/2013 | |

OTHER PUBLICATIONS

DelRio D., Stewart, A., Mullen, W., Burns, J., Lean, M., Brighenti, F., Crozier, A. HPLC-MS analysis of phenolic compounds and purine alkaloids in green and black tea. J. Agric. Food Chem. 2004, 52, 2807-2815.*

Wang et al. WO 2007003068 A1 (2007) machine translation. Retrieved on Feb. 22, 2013 from http://translate.google.com.*

Definition of "compound" and "composition" in Grant and Hackh's chemical dictionary, 5th Ed. McGraw Hill. 1987.p. 148. ISBN 0-07-024067-1.*

Related U.S. Appl. No. 12/317,638, filed Dec. 23, 2008, Huang, et al.
Related U.S. Appl. No. 12/868,634, filed Mar. 1, 2010, Huang, et al.
Related U.S. Appl. No. 12/715,270, filed Mar. 1, 2010, Huang, et al.
Related U.S. Appl. No. 13/680,007, filed Nov. 16, 2012, Huang, et al.
Related U.S. Appl. No. 13/135,123, filed Jun. 24, 2011, Huang, et al.
Related U.S. Appl. No. 13/135,124, filed Jun. 24, 2011, Huang, et al.
Related U.S. Appl. No. 13/135,125, filed Jun. 24, 2011, Huang, et al.
Related U.S. Appl. No. 13/135,128, filed Jun. 24, 2011, Huang, et al.
International Search Report for PCT/US2010/02805, Apr. 23, 2010, Metaactiv, Inc.—related case.

Absolute Astronomy, Catechin, The Source of this article is Wikipedia,http://en.wikipedia.org/w/index.php?title=Catechin&oldid=77274034, Jan. 2008, 5 pages.

Akagawa et al., Production of Hydrogen Peroxide by Polyphenols and Polyphenol-rich Beverages UndeQuasi-physiological Conditions, Bioscience Biotechnol Biochem, 67(12), Sep. 2003, pp. 2632-2640.

Akiyama et al. Antibacterial Action of Several Tannins Against Staphylococcus Aureus, Journal of Antimicrobial Chemotherapy, Jan. 2001, 48, pp. 487-491.

Aoshima et al., Antioxidative and Anti-hydrogen Peroxide Activities of Various Herbal Teas, Department of Chemistry, Faculty of Science, Yamaguchi University, 1677-1 Yoshida, Yamaguchi 753-8512, Japan, Available online Oct. 2 ,2006, 1 page.

Asquith, T.N., et al., Interactions of Condensed Tannins with Selected Proteins, Phytochemistry, 1986, 25, pp. 1591-1593.

Avdiushko, S.A., et al., Detection of Several Enzymatic Activities in Leaf Prints of Cucumber Plant, Physiological and Molecular Plant Pathology, 1993, 42, pp. 441-454.

Baeuerle, P.A., Reactive Oxygen Intermediates as Second Messengers of a General Pathogen Response, Pathol Biol., 1996, 44(1), pp. 29-35.

Barroso, J.B., et al., Localization of Nitric-oxide Synthase in Plant Peroxisomes, The Journal of Biological Chemistry, 1999, 274(51), pp. 36729-36733.

Berglin, E.H., et al., Potentiation by L-Cysteine of the Bactericidal Efffect of Hydrogen Peroxide in Escherichia Coli, J. Bacteriol., 1982, 152(1), pp. 81-88.

Berglin, E. H., et al., Potentiation by Sulfide of Hydrogen Peroxide-Induced Killing of Escherichia Coli, Infection and Immunity, 1985, 49(3), pp. 538-543.

Bernays, E.A., et al., Herbivores and Plant Tannins, Advances in Ecological Research, 1989, 19, pp. 263-302.

Bittner, When Quinones Meet Amino Acids: Chemical, Physical, and Biological Consequences, Amino Acids, Apr. 13, 2006, 30, pp. 205-224.

Blair, T.S., Botanic Drugs Their Materia Medica, Pharmacology and Therapeutics, The Therapeutic Digest Publishing Company, Cincnnati, Ohio, Jan. 1917, 20 pages.

Bowditch, M.I., et al., Ascorbate Free-Radical Reduction by Glyoxysomal Membranes, Plant Physiology, 1990, 94, pp. 531-537.

Bowler, C., et al., Superoxide Dismutase and Stress Tolerance, Annu Rev Plant Physiol Plant Mol Biol, 1992, 43, pp. 83-116.

Bowler, C., et al., Superoxide Dismutase in Plants, Crit Rev Plant Sci, 1994, 13(3), pp. 199-218.

Breusegem, F.V., et al., The Role of Active Oxygen Species in Plant Signal Transduction, Plant Science, 2001, 161, pp. 405-414.

(56) References Cited

OTHER PUBLICATIONS

Buchanan-Wollaston, V., The Molecular Biology of Leaf Senescence, 1997, J. Exp. Bot, 48(2), pp. 181-199.
Bunkelmann, J.R., et al., Ascorbate Peroxidase. A Prominent Membrane Protein in Oilseed Glyoxysomes, 1996, Plant Physiol.,110(2), pp. 589-598.
Butler, E., et al., The role of Lysyl Oxidase and Collagen Crosslinking During Sea Urchin Development, Exp Cell Res, 1987, 173, pp. 174-182.
Butler, L.G., et al., Interaction of Proteins with Sorghum Tannin: Mechanism, Specificity and Significance, Journal of the American Oil Chemists' Society, 1984, 61(5), pp. 916-920.
Chemtutor Solutions, [online] http://www.chemtutor.com/solution.htm, 11 pages. May 8, 1998, [retrieved from the Internet archive Wayback Machine using internet URL http://wayback.archive.org/web/*/http://www.chemtutor.com/solution.htm].
Cheng, et al., Progress in Studies on the Antimutagenicity and Anticarcinogenicity of Green Tea Epicatechins, abstract, Chin. Med. Sci. J., Dec. 1991, 6(4), 1 page.
Cheng, H.Y., et al., Antiherpes Simplex Virus Type 2 activity of Casuarinin from the Bark of Terminalia Arjuna Linn, Antiviral Research, 2002, 55(3), pp. 447-455.
Cordeiro, C., et al., Antibacterial Efficacy of Gentamicin encapsulated in pH-Sensitive Liposomes against an In Vivo Salmonella enteric Serovar Typhimurium Intracelllular Infection Model, Antimicrobial agents and Chemotherapy, 2000, 44(3), pp. 533-539.
Corpas, F.J., et al., A Role for Leaf Peroxisomes in the Catabolism of Purines, 1997, J. Plant Physiol, 151, pp. 246-250.
Corpas, F.J., et al., Copper—Zinc Superoxide Dismutase is a Constituent Enzyme of the Matrix of Peroxisomes in the Cotyledons of Oilseed Plants, New Phytol, 1998, 138(2), pp. 307-314.
Dayan et al., Oleic Acid-induced Skin Penetration Effects of a Lamellar Delivery System, excerpt (Cosmetics & Toiletries Magazine. Cosmetics and Toiletries.com, http://www.cosmeticsandtoiletries.com/formulating/ingredientldelivery/9496857.html, Aug. 31, 2007, 2pages.
De Paepe, K., et al., Repair of Acetone and Sodium Lauryl Sulphate-Damaged Human Skin Barrier Function Using Topically Applied Emulsions Containing Barrier Lipids, abstract, Journal of European Academy of Dermatology & Venereology, Nov. 2002, 1 page.
Del Río, L.A., et al., Metabolism of Oxygen Radicals in Peroxisomes and Cellular Implications, Free Radical Biol Med, 1992, 13(5), pp. 557-580.
Del Río, L.A., et al., Peroxisomes as a Source of Superoxide and Hydrogen Peroxide in Stressed Plants, Biochem Soc Trans, 1996, 24, pp. 434-438.
Del Rio, L.A., et al., The Activated Oxygen Role of Peroxisomes in Senescence, Plant Physiol, 1998, 116(4), pp. 1195-1200.
Doke, N., et al., The Oxidative Burst Protects Plants Against Pathgen Attack: Mechanism and Role as an Emergency Signal for Plant Bio-Defence, Gene, 1996, 179(1), pp. 45-51.
Dudley et al., Cysteine as an Inhibitor of Polyphenol Oxidase, abstract, Journal of Food Biochemistry. Feb. 23, 2007,13(1), 1 page.
El Amin, F.M., et al., Genetic and Environmental Effects upon Reproductive Performance of Holstein Crossbreds in the Sudan, Dairy Sci, 1986, 69, pp. 1093-1097.
Elstner, E.F., et al., Mechanisms of Oxygen Activation During Plant Stress, Proceedings of the Royal Society of Edinburgh B Biology, 1994, 102B, pp. 131-154.
Fang, T.K., et al., Electron Transport in Purified Glyoxysomal Membranes from Castor Bean Endosperm, Planta, 1987, 172(1), pp. 1-13.
Feldman et al,. Binding Affinities of Gallotannin Analogs with Bovine Serum Albumin: Ramifications for Polyphenol-protein Molecular Recognition, Phytochemistry Jan. 1999, 51, Elsevier Science Ltd., pp. 867-872.
Fridovich, I., Superoxide Dismutases, Adv Enzymol Relat Areas Mol Biol, 1986, 58, pp. 61-97.
Funatogawa, K., et al., Antibacterial Activity of Hydrolysable Tannins Derived from Medicinal Plants against Helicobacter Pylori, Microbiol Immunol, 2004, 48(4), pp. 251-261.
Gallily, R., et al., Non-immunological Recognition and Killing of Xenogeneic Cells by Macrophages. III. Destruction of Fish Cells by Murine Macrophages, Dev Comp Immunol., 1982 Summer, 6(3), pp. 569-578.
Gallochem Co., Ltd., Gallotannin, http://www.gallochem.com/Gallochem I.htm, Jan. 2002, 4 pages.
Gan, S., et al., Making Sense of Senescence. Molecular Genetic Regulation and Manipulation of Leaf Senescence, Plant Physiol., 1997, 113, pp. 313-319.
Goel et al., Xylanolytic Activity of Ruminal Streptococcus Bovis in Presence of Tannic Acid, Annals of Microbiology, Jan. 2005, 55(4), pp. 295-297.
Grabber, Mechanical Maceration Divergently Shifts Protein Degradability in Condensed-Tannin vso-Quinone Containing Conserved Forages, Crop Science, Mar. 19, 2008, 48, 2 pages.
greentealovers.com, Green Tea, White Tea: Health Catechin,http://greentealovers.com/greenteahealthcatechin.htm#catechin, Accessed Feb. 9, 2010, pp. 1-13.
Guo et al., Studies on Protective Mechanisms of Four Components of Green Tea Polyphenols Against Lipid Peroxidation in Synaptosomes, abstract, Biochim. Biophys. Acta Dec. 13, 1996, 1304(3), 1 page.
Hagerman, A.E., et al., The Specificity of Proanthocyanidin-Protein Interactions, Journal of Biological Chemistry, 1981, 256(9), pp. 4494-4497.
Hagerman, A.E., et al., Specificity of Tannin-Binding Salivary Proteins Relative to Diet Selection by Mammals, Canadian Journal of Zoology, 1992, 71, pp. 628-633.
Halwani, M., et al., Bactericidal Efficacy of Liposomal Aminoglycosides against Burkholderia cenocepacia, Journal of Antimicrobial Chemotherapy, 2007, 60, pp. 760-769.
Hasson, et al., Protein Cross-linking by Peroxidase: Possible Mechanism for Sclerotization of Insect Cuticle, abstract Archives of Insect Biochemistry and Physiology, Dec. 16, 1986, 1 page.
Ho, et al., Antioxidative Effect of Polyphenol Extract Prepared from Various Chinese Teas, abstract Prev. Med .Jul. 1992, 21(4), 1 page.
Ishiguro et al., Effects of Conjugated Linoleic Acid on Anaphylaxis and Allergic Pruritus,Biol. Pharm. Bull., Dec. 2002, 25(12), pp. 1655-1657.
Ishikawa et al Effect of Tea Flavonoid Supplementatation on the Susceptibility of Low-density Lipoprotein to Oxidative Modification, abstract, Am J Clin Nutr, Aug. 1997, 66(2), 1 page.
Jiménez, A., et al., Evidence for the Presence of the Ascorbate-Glutathione Cycle in Mitochondria and Peroxisomes of Pea Leaves, Plant Physiol., 1997, 114(1), pp. 275-284.
Jiménez, A., et al., Ascorbate-Glutathione Cycle in Mitochondria and Peroxisomes of Pea Leaves: Changes Induced by Leaf Senescence, Phyton, 1997, 37, pp. 101-108.
Kabara, J. J., et al., Fatty Acids and Derivatives as Antimicrobial Agents, Antimicrobial Agents and Chemotherapy, 2(1), Jul. 1972, pp. 23-28.
Kamin et al., Stimulation by Dinitrophenol of Formation of Melanin-like Substance from Tyrosine by Rat Liver Homogenates, The Journal of Biological Chemistry, downloaded from www.jbc.org, on Oct. 31, 2008, pp. 735-744.
Kashiwada et al., Antitumor Agents, 129. Tannins and Related Compounds as Selective Cytotoxic Agents, abstract, J Nat Prod, Aug. 1992, 55(8), 1 page.
Kilic et al., Fatty Acid Compositions of Seed Oils of Three Turkish Salvia Species and Biological Activities, Chemistry of Natural Compounds, 41(3), Jan. 2005, Springer Science+Business Media, Inc., pp. 276-279.
Kim et al., Effect of Glutathione, Catechin and Epicatechin on the Survival of Drosophilia Melanogaster Under Paraquat Treatment, abstract, Biosci. Biotechnol Biochem, Feb. 1997 ,61(2), 1 page.
Kim et al., Research Note: Antimicrobial Effect of Water-Soluble Muscadine Seed Extracts on Escherichia coli 0157:H7, abstract, Journal of Food Protection, 71(7), Jul. 2008, 1 page.
Kim et al., Measurement of Superoxide Dismutase-like Activity of Natural Antioxidants, abstract, Viosci Biotechnol Biochem, May 1995, 59(5), 1 page.

(56) References Cited

OTHER PUBLICATIONS

Kolodziej, H., et al., Antileishmanial Activity and Immune Modulatory Effects of Tannins and Related Compounds on Leishmania Parasitised Raw 264.7 Cells, Phytochemistry, 2005, 66(17), pp. 2056-2071.

Krab-Husken, L., Production of Catechols, Microbiology and Technology, Thesis Wageningen University, The Netherlands, Jan. 2002, ISBN 90-5808-678-X, pp. 9-144.

Kuboe, et al., Quinone cross-Linked Polysaccharide Hybrid Fiber, Biomacromolecules, 2004, 5(2), pp. 348-357.

Lagrimini, L.M., Wound-Induced Deposition of Polyphenols in Transgenic Plants Overexpressing Peroxidase, Plant Physiol, 1991, 96, pp. 577-583.

Lamb, C., et al., The Oxidative Burst in Plant disease Resistance, Annu Rev Plant Physiol Mol Bio, 1997, 48, pp. 251-275.

Landolt, R., et al., Glyoxysome-like Microbodies in Senescent Spinach Leaves, Plant Sci., 1990, 72(2), pp. 159-163.

Lane, B.G., Oxalate Oxidases and Differentiating Surface Structure in Wheat: Germins, Biochem J., 2000, 349, pp. 309-321.

Lee et al., Antimicrobial Synergistic Effect of Linolenic Acid and Monoglyceride Against Bacillus Cereus and Staphylococcus Journal of Agricultural and Food Chemistry, Jan. 2002, 50, pp. 2193-2199.

Leshem, Y.Y., Plant Senescence Processes and Free Radicals, Free Radical Biol. Med., 1988, 5(1), pp. 39-49.

Li, J., et al., Hydrogen Peroxide and Ferulic Acid-Mediated Oxidative Cross-linking of Casein catalyzed by Horseradish Peroxidase and the Impacts on Emulsifying Property and Microstructure of Acidified Gel, African Journal of Biotechnology, 2009, 8(24), pp. 6993-6999.

Li, W-Z., et al.., Stabilizing the Bactericidal Activity of Hydrogen Peroxide: A Brandnew Function of Certain Chinese Herbs, Chin J Integr Med, Dec. 3, 2012, 6 pages.

Lin, C.C., et al., Hydrogen Peroxide Level and NaCl-inhibited Root Growth of Rice Seedlings, Plant and Soil, 2001, 230, pp. 135-143.

López-Huertas, E., et al., Superoxide Generation in Plant Peroxisomal Membranes: Characterization of Redox Proteins Involved, Biochem. Soc. Trans., 1996, 24, 195S.

López-Huertas, E., et al., Superoxide Radical Generation in Peroxisomal Membranes: Evidence for the Participation of the 18-kDa Integral Membrane Polypeptide, Free Radical Res., 1997, 26(6), pp. 497-506.

Lopez-Huertas, E., et al., Stress Induces Peroxisome Biogenesis Genes, The EMBO Journal, 2000, 19(24), pp. 6770-6777.

Lotito et al., Catechins Delay Lipid Oxidation and α-Tocopherol and β-Carotene Depletion Following Ascorbate Depletion in Human Plasma, Society for Experimental Biology and Medicine, Apr. 2000, pp. 32-38.

Low, P.S., et al., The Oxidative Burst in Plant Defense: Function and Signal Transduction, Physiologia Plantarum, 1996, 96(3), pp. 533-542.

Lu, L., et al., Tannin Inhibits HIV_1 Entry by Targeting gp41, Acta Pharmacol Sin, Feb. 2004, 25(2), pp. 213-218.

Luster, D.G., et al., Orientation of Electron Transport Activities in the Membrane of Intact Glyoxysomes Isolated from Castor Bean Endosperm, Plant Physiol, 1987, 85, pp. 796-800.

MacPhillamy, HB., Drugs from Plants, Plant Science Bulletin, Apr. 1963, 9(2), pp. 1-15.

Maffei, et al., Relevance of Apple Consumption for Protection Against Oxidative Damage Induced by Hydrogen Peroxide in Human Lymphocytes; The British Journal of Nutrition, Cambridge, 97(5), May 2007, pp. 921-928.

Matile, P., et al., Chlorophyll Breakdown in Senescent Leaves, Plant Physiol., 1996, 112(4), pp. 1403-1409.

Matsumoto et al. Inhibitory Effects of Tea Catechins, Black Tea Extract and Oolong Tea Extract on Hepatocarcinogenesis in Rat, abstract, Jpn. J. Cancer Res., Oct. 1996, 87(10), 1 page.

Mohammadi, M., et al., Changes in Peroxidase and Polyphenol activity in Susceptible and Resistant Wheat Heads Inoculated with fusarium Granminearum and Induced Resistance, Plant Science, 2002, 162, pp. 491-498.

Mole, S., et al., In G.R. Waller, Allelochemicals: Role in Agriculture and Forestry, 1987, pp. 572-587, Washington D.C., A.C.S.

Morris et al.Affinity Precipitation of Proteins by Polyligands, http://www.ncbi.nlm.nih.gov/pubmed/18601281. Biotechnol Bioeng, Apr. 25, 1993, 41(10), 1 page.

Mugabe, C., et al., Mechanism of Enhanced Actibvity of Liposoome-entrapped Aminoglycosides Against Resistant Strains of Pseudomonas aeruginosa, Antimicrob. Agents Chemother., 2006, 50, pp. 2016-2022.

Nanjo et al., Scavenging Effects of Tea Catechins and Their Drivia-tives on 1, 1-diphenyl- 2-picrythydrazyl Radical, abstract free Radic. Bioi. Med .Jan. 1996, 21(6), 1page.

Narayanan, B., et al., p53/p21 (WAF1/CIP1) Expression and Its Possible Role in G1 Arrest and Apoptosis in Ellagic Acid Treated Cancer Cells, Cancer Letters, 1999, 136, pp. 215-221.

Nishimura, M., et al., Leaf peroxisomes are Directly Transformed to Glyoxysomes During Senescence of Pumpkin Cotyledons, Protoplasma, 1993, 175(3-4), pp. 131-137.

Nonaka, G-I., et al., Anti-AIDS Agents, 2: Inhibitory Effects of Tannins on HIV Reverse Transcriptase and HIV Replication in H9 Lymphocyte Cells, J. Natl. Prod., 1990, 53(3), pp. 587-595.

Obermeier et al., Effects of Bioflavonoids on Hepatic P450 Activities, abstract, Xenobiotica, Jun. 1995, 25(6), 1 page.

Omega-3 Fatty Acids, University of Maryland Medical Center, http://www.umm.edulaltmedlarticles/omeza-3-000316.htm accessed Feb. 12, 2010.

Orozco-Cardenas, M., et al., Hydrogen Peroxide is Generated Systematically in Plant Leaves by Wounding and Systemin via the Octadecanoid Pathway, Proc. Natl. Acad. Sci. USA, May 1999, 96, pp. 6553-6557.

Parrish, JR et al., Effects of Conjugated Linoleic Acid (CLA) on Swine Performance and Body Composition, Jan. 1998/997 Swine Research Report, Iowa State University, AS-638, pp. 187-190.

Pastori, G.M., et al., an Activated-Oxygen-Mediated Role for Peroxisomes in the Mechanism of Senescence of Pisum Sativum, Planta, 1994, 193(3), pp. 385-391.

Pastori, G.M., et al., Activated Oxygen Species and Superoxide Dismutase Activity in Peroxisomes from Senescent Pea Leaves, Proc R Soc Edinb Sect B Biol, 1994, 102B, pp. 505-509.

Pastori, G.M., et al., Natural Senescence of Pea Leaves: an Activated Oxygen-Mediated Function for Peroxisomes, Plant Physiol., 1997, 113(2), pp. 411-418.

Pistelli, L., et al., Glyoxylate Cycle Enzyme Activities are Induced in Senescent Pumpkin Fruits. Plant Sci., 1996, 119(1-2), pp. 23-29.

Preuss, H.G., et al., Minimum Inhibitory Concentrations of Herbal Essential Oils and Monolaurin for Gram-positive and Gram-negative Bacteria, Molecular and Cellular Biochemistry, Jan. 2005, 272, pp. 29-34.

Prottey et al., The Mode of Action of Ethyt Lactate as a Treatment for Acne, British Journal of Dermatology, 110(4), Jul. 29, 2006.

Pryor, M.G.M., On the Hrdening of the Ootheca of Blatta Orientalis, Soc Lond Ser B, 1940, 128, pp. 378-393.

Quideau, S., et al., Main Structural and Stereochemical Aspects of the Antiherpetic Activity of Nonahydroxyterphenoyl-Containing C-Glycosidic Ellagitannins, Chemistry and Biodiversity, 2004, 1(2), pp. 247-258.

Raskin, et al., Can an Apple a Day Keep the Doctor Away?, Current Pharmaceutical Design, 2004, 10, pp. 3419-3429.

Ray, H., et al., Transformation of Potato with Cucumber Peroxidase: Expression and disease Response, Physiological and Molecular Plant Pathology, 1998, 53, pp. 93-103.

Robertson, J.A., et al., Peroxidase-Mediated Oxidative Cross-Linking and Its Potential to Modify Mechanical Properties in Water-Soluble Polysaccharide Extracts and Cereal grain Residues, abstract, J Agric Food Chem, 2008, 56(5), 1 page.

Roginsky et al., Oxidation of Tea Extracts and Tea Catechins by Molecular Oxygen, abstract, Journal of Agricultural Food Chemistry, 52(II), Apnl 30, 2005, 1 page.

Rucker et al, Copper, Lysyl Oxidase, and Extracellular Matrik Protein Cross-linking, The American Journal of Clinical Nutrition, '67(suppl.), Jan. 1998, pp. 996S-1002S.

(56) References Cited

OTHER PUBLICATIONS

Sachinidis et al., Are Catechins Natural Tyrosine Kinase Inhibitors? Drug News & Perspectives, Jan. 2002, 15(7), 432, ISSN 0214-0934, 1 page.
Sasaki, et al., Ecabet Sodium Prevents the Delay of Wound Repair in Intestinal Epithelial Cells Induced by Hydrogen Peroxide, J. Gastroenterol, 40, 2005, pp. 474-482.
Sato, et al., Ammonia Hydrogen Peroxide, and Monochloramine Retard Gastric Epithelial Restoration in Rabbit Cultured Cell Model, Digestive Diseases and Sciences, New York, 44(12), Dec. 1, 1999, pp. 2429-2434.
Schweikert et al., Scission of Polisaccharides by Peroxidase-Generated Hydroxyl Radicals, Phytochemistry, 53(5), Mar. 1, 2000, 2 pages.
Scott, et al., Evaluation of the Antioxidant Actions of Ferulic Acid and Catechins, abstract, Free Radic Res Commun, Jan. 1993, 19(4), 1 page.
Sebedio, J-L, et al., Vegetable Oil Products, Advances in Conjugated Linoleic Acid Research, Jan. 2003, 2, Urbana, IL, 2 pages.
Selinheimo,Tyrosinase and Laccase as Novel Crosslinking Tools for Food Biopolymers,http:/lib.tkk.fi/Diss/2008/isbn9789513871185/index.html, age last updated: Feb. 2, 2010, Page maintained by: diss@tkk, fi, 5 pages.
Smart, C.M., Gene Expression During Leaf Senescence, New Phytol, 1994, 126(3), pp. 419-448.
Stachowicz, J.J., et al., Reducing Predation Through Chemically Mediated Camouflage: Indirect Effects of Plant Defenses on Herbivores, Ecology, 1999, 80(2), pp. 495-509.
Stahmann, M.A., et al., Cross Linking of Proteins In Vitro by Peroxidase, Biopolymers, 16(6), pp. 1307-1318.
Stapleton et al., Potentiation of Catechin Gallate-Mediated Sensitization of Staphylococcus Aureus to Oxacillin by Nongalloylated Catechins, Antimicrobial Agents and Chemotherapy, Feb. 2006, pp. 752-755.
Steele, et al., Chemopreventive Efficacy of Black and Green Tea Extracts in Vitro Assays, meeting abstract, Proc Annu Meet Am Assoc Cancer Res, Jan. 1996, 37, 1 page.
Sugumaran, M., Comparative Biochemistry of Eumelanogenesis and the Protective Roles of Phenoloidase and Melamin in Insects, Pigment Cell Res., 2002, 15(1), pp. 2-9.
Tanimura, S., et al., Suppression of Tumor Cell Invasiveness by Hydrolyzable Tannins (Plant Polyphenols) via the Inhibition of Matrix Metalloproteinase-2/-9 Activity, Biochemical and Biophysical Research Communications, 2005, 330, pp. 1306-1313.
Terao et al., Protective Effect of Epicatechin, Epicatechin Gallate, and Quercetin on Lipid Peroxidation in Phospholipid Bilayers, abstract; Arch Biochem Biophys, Jan. 1994, 308(1), 1 page.
Thompson, J.E., et al., Tansley Review No. 8. The Role of Free Radicals in Senescence and Wounding, New Phytol, 1987, 105, pp. 317-344.
Tomisato, et al., Maturation Associated Increase in Sensitivity of Cultured Guinea Pig Gastric Pit Cells to Hydrogen Peroxide, Digestive Diseases and Sciences, New York, Sep. 2002, 47(9), pp. 212-2132.
Uyama et al., Enzymatic Synthesis and Properties of Polymers from Polyphenols, Advances in Polymer Science, Jan. 2006, 194, ISSN 0065-3195, 1 page.
Valcic et al., Inhibitory Effect of Six Green Tea Catechins and Caffeine on the Growth of Four Selected Human Tumor Cell Lines, abstract, Anticancer Drugs, Jun. 1996, 7(4),1 page.
Van Den Bosch, H., et al., Biochemistry of Peroxisomes, Annu. Rev. Biochem., 1992, 61, pp. 157-197.
Van Gerlder, C.W.G., et al., Sequence and Structural Features of Plant and Fungal Tyrosinases, Phytochemistry, 1997, 45(7), pp. 1309-1323.
Varghese et al., Effect of Asoka on the Intracellular Glutathione Levels and Skin Tumor Promotion in Mice, abstract, Cancer Lett, Apr. 15, 1993 , 69(1), 1 page.

Wang, S.X., et al., A crosslinked Cofactor in Lysyl Oxidase: Redox Function for Amino Acid Side Chains, Science, 1996, 273(5278), pp. 1078-1084.
Weiss, et al., Review: Conjugated Linoleic Acid: Historical Context and Implications 1, Professional Animal Scientist, Apr. 2004, 29 pages.
Wiechers, J.W., Nutraceuticals and Nanoparticles, Cosmetics & Toiletries Magazine, CosmeticsAndToiletries.com, http://www.cosmeticsandtoiletries.com/research/techtransfer/9431641.html?page=4.
Willekens, H., et al., Catalase is a Sink for $H_2O_2$ and is Indispensable for Stress Defense in $C_3$ Plants, The EMBO Journal, 1997, 16(16), pp. 4806-4816.
Wikipedia, Tannin, http://en.wikipedia.org/wikilTannin, This page was last modified on Jan. 30, 2010, 35 pages.
Woo, E.-J., et al., Germin is a Manganese Containing Homohexamer with Oxalate Oxidase and Superoxide Dismutase Activities, Nature Structural Biology, 2000, 7(11), pp. 1036-1040.
Wu-Yuan et al.,Gallotannins Inhibit Growth, Water-insoluble Glucan Synthesis, and Aggregation of Mutans Streptococci, J Dent Res, Jan. 1988, 67(1), pp. 51-55.
Yamaguchi, K., et al., A Novel Isoenzyme of Ascorbate Peroxidase Localized on Dlyoxysomal and Leaf Peroxisomal Membranes in Pumpkin, Plant Cell Physiol., 1995, 36(6), pp. 1157-1162.
Yamamoto et al., Roles of Catalase and Hydrogen Peroxide in Green Tea Polyphenol-Induced Chemopreventive Effects, Journal of Pharmacology and Experimental Therapeutics Fast forward, 2003, 32 Pages, DOI:10.1124/jpet.103.058891, JPET #58891.
Yamamoto et al., Studies on Quinone Cross-linking Adhesion Mechanism and Preparation of Antifouling Surfaces Toward the Blue Mussel, abstract, Journal of Marine Bitechnology, 5(2-3), May 1997, 1 page.
Yang, L-L., et al., Induction of Apoptosis by Hydrolyzable Tannins from Eugenia Jambos L. on Human Leukemia Cells, Cancer Letters, 2000, 157, pp. 65-75.
Yokozawa, T., et al., Effects of Rhubarb Tannins on Renal Function in Rats with Renal Failure, abstract, Nippon Jinzo Gakkai Shi, Jan. 1993, 35(1), 1 page.
Yoshino et al., Antioxidative Effects of Black Tea Theaflavins and Thearubigin on Lipid Peroxidation of Rat Liver Homogenates Induced by Tert-butyl Hydroperoxide, abstract, Biol Pharm Bull, Jan. 1994, 17(1), 1 page.
Zhang et al., Inhibitory Effects of Jasmine Green Tea epicatechin Isomers on Free Radical-induced Lysis of Red Blood Cells, abstract Life Sci, Jan. 1997, 61(4), 1 page.
Zheng, C.J., et al., Fatty Acid Synthesis is a Target for Antibacterial Activity of Unsaturated Fatty Acids, FEBS Letters, 2005, 579, pp. 5157-5162.
Zhu et al., Antioxidant Chemistry of Green Tea Catechins: Oxidation Products of (−)- Epigallocatechin Gallate and (−)-With Peroxidase, Wiley InterScience Journals: Journal of Food Lipids, May 5, 2007, 7(4), 1 page.
Related U.S. Appl. No. 13/726,180, filed Dec. 23, 2012, Huang, et al.
Related U.S. Appl. No. 13/772,264, filed Feb. 20, 2013, Huang, et al.
International Search Report for PCT/US2012/043900, Jan. 30, 2013, LiveLeaf, Inc—related case.
Agnivesa, Caraka Samhita, Edited & translated by P. V. Sharma, vol. II: Chaukhamba Orientalia, Varanasi, Edn. $5^{th}$, 2000. [ time of origin 1000 BC—$4^{th}$ century] p. 418.
Bhavamisra; Bhavaprakasa, Edited & translated by Brahmasankara Misra, Part II: Chaukhamba Sanskrit Sansthan, Varanasi, Edn $7^{th}$, 2000. [Time of orgin $16^{th}$ centuty] p. 474.
Guo, et al., Evaluation of Antioxidant Activity and Preventing DNA Damage Effect of Pomegrante Extracts by Chemiluminescence Method, J Agric Food Chem, 2007, 55, pp. 3134-3140.
Hagerman, Tannin Chemistry, Oxford, OH, Jan. 1998, 116 pages.
Kahn, Khazaain-al-advia, vol. II ($20^{th}$ century AD), Nadeem Yunas Printer/Sheikh Mohd Basheer & Sons, Lahore, 1911 p. 611.
Lin, et al Tannin inhibitas HIV-1 entry by targeting gp41 Acta Pharmacol Sin. Feb. 2004: 25(2): 213-218.
Mohammad.Bin Zakariyya Al-Razi; Kitaab-al-Haawi-fil-Tibb, vol. IX ($9^{th}$ century A.D.), Dayerah-al-Ma'aarif Usmania, Hyderabad, (First Edition) 1960 p. 194.

(56) References Cited

OTHER PUBLICATIONS

Mohammad.Bin Zakariyya Al-Razi; Kitaab-al-Haawi-fil-Tibb, vol. XX ($9^{th}$ century A.D.), Dayerah-al-Ma'aarif Usmania, Hyderabad, (First Edition) 1967 p. 226.
Ratnakara, Complied by Naginadasa Chaganalala Saha, Translated by Gopinath Gupta, vol. V: B. Jain Publishers, New Delhi, Edn. $2^{nd}$ Reprint, Aug. 1999.[This book contains back references from 1000 B.C. to 20 th century] p. 736.
Smkaradajisastripade: Aryabhisaka-Gujarati Edited (Hindustana No Vaidyaraja) Translation by Harikrishna Bhagwan Lal Vyas: Sastu Sahitya Vardhaka Karyalaya, Bhadra, Ahmedabad, Edn. $12^{th}$, 1957 p. 92.
Stark, D., et al., Irritable Bowel Syndrome: A Review of the Role of Intestinal Protozoa and the Importance of their Dectection and Diagnosis, Intl J Parasitology, 2007, 37, pp. 11-20.
Vangasena, Commentator Shaligram Vaisya, Edited Shankar Lalji Jain:Khemraj Shrikrishna Das Prakashan, Bombay, Edn. 1996 p. 1046.
Vermerris, W., et al., Phenolic Compound Biochemistry, Springer, 2008, 13 pages.
Ziya Al-Din Abdullah Ibn Al-Baitar: Al-Jaam'e-li-Mufradaat-al-Advica-wal-Aghzia, vol. 1 ($13^{th}$ century AD), Matba Amra, Cairo, Egypt, 1874 A.D. p. 162.
Related U.S. Appl. No. 14/027,228, filed Sep. 15, 2013, Huang, et al.
Related U.S. Appl. No. 14/027,235, filed Sep. 15, 2013, Huang, et al.
International Search Report for PCT/US2011/06276-7, Aug. 15, 2013, Metaactiv, Inc.
Clyde E.H., Effects of temperature on catalase activity. Ohio Journal of Science. 50(6): 273-277 (Nov. 1950).
Croft, K.D. The chemistry ad biological effects of flavonoids and phenolic acids. Annals of the New York Academy of Sciences. 845-442. 1998.
Dayyf et al. Recent advances in polyphenol research. Blackwell publishing 264, 3. (2008).
Dec, J. et al., use of plant material for the decontamination of water polluted with phenols. Biotechnology and Bioengineering, 44, 1132-1139. (1994).
Gee, J.M., et al. Polyphenolic compounds: Interactions with the gut and implications for human health. Current medical chemistry. 8, 1245-1255 (2001).
Heber, D. Multitargeted therapy of cancer by ellagitannins. Cancer Letters 269: 262-268. (2008).
Kirsch M. et al. Metastasis and angiogenesis. Cancer treat res.117: 285-304 (2004).
Koloski N.A., et al. The brain-gut pathway in functional gastrointestinal disorders is bidirectional. A 12-year prospective population-based study. Gut 61(9): 1284-1290. (2012).
Labieniec, M., et al. Study of interactions between phenolic compounds and $h_2o_2$ or cu(ii) ions in b14 chinese hamster cells. Cell Biology Int'l, 30, pp. 761-768 (2006).
Labieniec, M., et al. Response of digestive gland cells of freshwater mussel Unio tumidus to phenolic compound exposure in vivo. Cell Biology International. 31(7): 683-690 (2007).
Longstreth G., et al. Functional bowel disorders. Gastroenterology 130: 1480-1491. 2006.
Poyrazoglu, E., et al., Organic acids and phenolic compounds in pomegranates (punica granatum I.) grown in turkey. J Food Comp Analysis, 15, 567-575 (2002).
Schiller L.R. Definitions, pathophysiology, and evaluation of chronic diarrhea. Best pract res clin gastroenterol 26(5): 551-562. 2012.
Schopfer, P. et al., Realease of reactive oxgen intermediates (Superoxide radicals, hydrogen peroxide, and hydroxyl radicals) and peroxidase in germinating radish seeds controlled by light, gibberellin, and abscisic acid. Plant Physiology vol. 125, pp. 1591-1602 Apr. 2001.
Related U.S. Appl. No. 14/142,895, filed Dec. 23, 2012, Huang, et al.
Related U.S. Appl. No. 14/142,902, filed Dec. 23, 2012, Huang, et al.
Related U.S. Appl. No. 14/173,079, filed Dec. 23, 2012, Huang, et al.
Related U.S. Appl. No. 14/173,357, filed Dec. 23, 2012, Huang, et al.
Related U.S. Appl. No. 14/178,459, filed Dec. 28, 2007, Huang, et al.
Related U.S. Appl. No. 14/203,517, filed Jun. 24, 2011, Huang, et al.
Related U.S. Appl. No. 14/221,500, filed Dec. 28, 2007, Huang, et al.
Related U.S. Appl. No. 14/222,605, filed Dec. 23, 2012, Huang, et al.
Related U.S. Appl. No. 14/222,607, filed Dec. 23, 2012, Huang, et al.
Related U.S. Appl. No. 14/255,431, filed Jun. 24, 2011, Huang, et al.
Related U.S. Appl. No. 14/272,047, filed Dec. 23, 2012, Huang, et al.
Related U.S. Appl. No. 14/272,163, filed Dec. 23, 2012, Huang, et al.
English translated office action for JP2011553012, Mar. 17, 2014, Shinsuke Aramaki.
A technical journal on food chemistry & chemicals 21(11) 2005. reference No. 12 on English translated office action for JP2011-553012 for relevance.
Definition of "Compound" and "Composition". Grant and Hackh's Chemical Dictionary, $5^{th}$ Ed. McGraw Hill 2 pages. (1987).
Del Rio, D., et al. HPLC-$MS^n$ analysis of phenolic compounds and purine alkaloids in green and black tea. J Agric Food Chem 52: 2807-2815 (2004).
Do-It-Yourself Health. Editor: R. Somerville, Time Life Books 2 pages (1997).
Drugs in Japan 2004 Jiho Inc. 494 (2003), reference No. 11 on English translated office action for JP2011-553012 for relevance.
Food processing 43(6): 44-58 (2008). reference No. 15 on English translated office action for JP2011-553012 for relevance.
Ghosh, A., et al. Antibacterial activity of some medicinal extracts. J Nat Med 62: 259-262 (2008). reference No. 14 on translated office actionfor JP2011-553012 for relevance.
Glossary of Medical Eduction Terms. (Online) URL: http://www.iime.org/glossary.htm [retrived on Mar. 24, 2011].
Hara-Kudo, Y., et al. Antibactreial action on pathogenic bacterial spore by green tea catechins. Journal of the science of food and agriculture 85: 2354-2361 (2005).
Mattiello, T. et al. Effects of pomegranate juice and extract polyphenols on platelet function. J med food 12(2): (2009).
Naz, S., et al. Antibacterial activity directed isolation of compounds from Punica granatum. 27(8): Journal of food science 27(9): 341-345 (2007). reference No. 13 on translated office action for JP2011-553012 for relevance.
Palombo, E. A. Phytochemicals from traditional medicinal plants used in the treatment of diarrhea: Modes of action and effects on intestinal function. Pyhtotherapy research 20: 717-724 (2006).
Prophylactic in websters new world dictionary (on line) URL: http://search.credoreference.com/content/entry/webstermed/prophylactic/0 retrieved on Jan. 28, 2014; cumulative of http://issuu.com/thilibrary/docs/webster_s_new_world_medical_dictionary_fully_revi. (downloaded Feb. 18, 2014).
Rasheed K. J. Detection of the klebsiella pneumonia carbapenemase type 2 carbapenem-hydrolyzing enzyme in clinical isolates of Citrobacter freundii and K. oxytoca carring a common plasmid. Journal of clinical microbiology 46(6): 2006-2069 (2008).
Youn H. J. et al. Screening of the anticoccidial effects of herb extracts against Eimeria tenella. Veterinary parasitology 96: 257-263 (2001).
Related U.S. Appl. No. 14/304,812, filed Jun. 13, 2014, Huang, et al.
European search report for EP 12802538, Sep. 30, 2014.
International Search Report for PCT/US2010/025805, Aug. 15, 2013, Metaactiv, Inc.
Ahn, et al. Tea polyphenols: Selective growth inhibitors of Clostridium spp. Algric Biol Chem 55(5): 1425-1426 (1991).
Azim T, et al. Lipopolysaccharid-specific antibodies in plasma and stool of children with shigella-associated leukemoid reaction andhemolytic-uremic syndrome. Clin diagn lab immunol 3(6): 701-705 (1996).
Bailey, et al. Regulation of mucosal immune responses in effector sites. Proc Nutr Soc 60: 427-435 (2001).
Bialonska, et al. Urolithias, intestinal microbial metabolites of pomegranate ellagitannins exhibit antioxidant activity in a cell-based assay. J Agric Food Chem 57: 10181-10186 (2009).
Biasi, et al. Polyphenol supplementation as a complementary medicinal approach to treating inflammatory bowel disease. Curr Med Chem 18: 4851-4865 (2011).
Biesalaki, H.K. Polyphenols and inflammation: basic interactions. Curr Opin Clin Nutr Metab Care 10: 724-728 (2007).

(56) References Cited

OTHER PUBLICATIONS

Bird, et al. Newer insights into the mechanism of action of Psidum guajava L. leaves in infectious diarrhea. BMC complement altern med 10: 33 (2010).
Bontempo, et al. Effects of a novel plant extract administred through drinking water on the post-weaning gut health of piglets. Submitted to J Anim Sci Jun. 2012.
Boudry, et al. Weaning induces both transient and long-lasting modifications of absorptive, secretory, and barrier properties of piglet intestine. J Nutr 134: 2256-2262 (2004).
Brown, et al. Outcomes of diarrhea management in operations Iraqi Freedom and Enduring Freedom. Travel med infect dis 7: 337-343 (2009).
Bruins, et al. In vivo and in vitro effects of tea extracts on enterogoxigenic Escherihia coli-induced instestinal fluid loss in animal models. J Pediatr Gastroenterol Nutr 43: 459-469 (2006).
Coates, et al. Molecular defects in serotonin content and decreased serotonin reuptake transporter in ulcerative colitis and irritable bowel syndrome. Gastroenterology 126(7): 1657-1664 (2004).
Desnoeck et al. Reducing sour in commercial pig farms with a novel plant extract-results of veterinary field trials. Poster presentation at international symposium on alternatives to antibiotics. Program to Alternatives to antibiotics (ATA). The world organization for animal health, Paris, France:78 (Sep. 25-28, 2012.).
Denes, et al. Minimal inhibitory concentration of a novel plant extract on growth of bacterial isolates with veteriany importance. Poster presentation at international symposium on alternatives to antibiotics. Program to Alternatives to antibiotics (ATA). The world organization for animal health, Paris, France:33 (Sep. 25-28, 2012.).
Domeneghini, et al. Gut topic feed additives and their effects upon the gut structure and intestinal metabolism. State of the art in the pig, and perspectives towards humans. Histol Histopathal 21: 273-883 (2006).
Faure, et al. Serotonin signaling in altered irritable bowel syndrome with diarrhea but not in functional dyspepsia in pediatric patients. Gastroenterology 139(1): 249-258 (2010).
FDA. The judicious use of medically important antimicrobial drugs in food-producing animals. U.S. Government Printing Office Washington, DC. 26 pp (2012).
Gulcin, et al. Radical scavenging and antioxidant activity of tannic acid. Arabian Journal of Chemistry 3: 43-53 (2010).
Hamman. Composition and application of aloe vera leaf gel. Mocecules 13: 1599-1610 (2008).
Hanauer, et al. Randomized, double-blind, placebo-controlled clinical trial of loperamide plus simethicone versus loperamide alone and simethicone alone in the treatment of acute diarrhea with gas-related abdominal discomfort. Curr med res opin 23(5): 1033-1043 (2007).
Heumann, et al. Initial responses to endotoxins and Gram-negative bacteria. Int J Clin Chem 323: 59-72 (2002).
Hughes. First-line treatment in acute non-dysenteric diarrhea: clinical comparison of loperamide oxide, loperamide and placebo. BJCP 49(4): 181-185 (1995).
Hyslop, et al. Hydrogen peroxide as a potent bacteriostatic antibiotic: implactions for the host. Free Radical Biology & Medicine 19(1): 31-37 (1995).
Ismail, et al. Pomegrante peel and fruit extracts: a review of potential anti-imflammatory and anti-infective effects. J Ethnopharmacol 143(2): 397-405 (2012).
Izzi, V., et al. The effects of dietary flavonoids on the regulation of redox inflammatory networks. Front biosci 17: 2396-2418 (2012).
Kaplan, et al. Loperamide-simethicone vs loperamide alone, simethicone alone, and placebo in the treatment of acute diarrhea with gas-related abdominal discomfort. Arch Fam med 8: 243-248 (1999).
Khennouf, et al. Effect of tannins from Quercus suber and Quercus coccifera leaves on ethanol-induced gastric lesions in mice. Journal of agricultural and food chemistry 51(5): 1469-1473 (2003).
Kostyuk, et al. The promose of plant polyphenois as the golden standard skin anti-inflammatory agents. Curr drug metab 11(15): 414-424 (2010).
Laine, et al. Risk factors for post-weaning diarrhea on piglet producing farms in Finland. Acta Vet Scand 50: 21-32 (2008).
Lalles, et al. Nutritional management of gut health in pigs around weaning. Proc Nutr soc 66: 260-268 (2007).
Lewis, et al. Stool form scale as a useful guide to intestinal transit time. Scand j gastroenterol 32(9): 920-924 (1997).
Liebregts T., et al. Immune activation in patents with irritable syndrome. Gastroenterology 132(3): 913-920 (2007).
Manzanilla, et al. Effect of plant extracts and formic acid on the intestinal equilibrium of early-weaned pigs. J Anim Soc 82: 3210-3218 (2004).
Opal, SM. Endotoxins and other sepsis triggers. Contrib Nephrol 167: 14-24 (2010).
Park, et al. Rapid cessation of acute diarrhea in pediatric patents using a novel plant extract. . Poster presentation at the annual meeting of North America Society of Pediatric Gastronterology, Hepatology and Nutrition, Oct. 2012. Cumulative of poster at Park, K. T. et al. Ann Mtg North Soc Ped Gastro Hepato and Nutrition (Oct. 2012) online http://lifedropsinternation.com/solution (downloaded Feb. 11, 2015).
Quideau, S., et al. Plant polyphenols: chemical properties, biological activities, and synthesis. Angew Chem Int Ed 50: 586-621 (2011).
Romier, B., et al. Dietary polyphenols can modulate the intestinal inflammatory response. Nutr rev 67(7): 368-378 (2009).
Sarmiento, et al. Postweaning diarrhea in swine. Am J Vet Res 49: 1154-1159 (1988).
Shimizu, M. Modulation of intestinal functions by food substances. Nahrung 43: 154-158 (1999).
Spreeuwenberg, et al. Small intestine epithelial barrier function is compromised in pigs with low feed intake at weaning. J Nutr 131: 1520-1527 (2004).
Taguri, et al. Antimicrobial activity of 10 different plant polyphenois against bacteria causing food-borne disease. Biol. Pharm. Bull. 27(12): 1965-1969 (2004).
Taras, et al. Performance, diarrhea incidence, and occurrence of Escherichia coli virulence genes during long-term administration of a probiotic Enterococcus faecium strain to sows and piglets. J Anim Sci 84: 608-616 (2006).
Tsao, R. Chemistry and biochemistry of dietary polyphenols. Nutrients 2: 1231-1246.
Vauzour, D., et al. Polyphenois and human health: prevention of disease and mechanisms of action. Nutrients 2(11): 1106-1131 (2010).
Vetel, et al.Comparision of raceadotril and loperamide in adults with acute diarrhea. Aliment Pharmacol Ther 13(6): 21-26 (1999).
Wang, H.H., et al. A blind, randomized comparison of raceadotril and loperamide for stopping acute diarrhea in adults. World J Gastroenterol 11(10): 1540-1543 (2005).
Wu, et al. A novel plantextract mix is capable of binding endotoxin. Poster presentation at international symposium on alternatives to antibiotics. Program to Alternatives to antibiotics (ATA). The world organization for animal health, Paris, France:77 (Sep. 25-28, 2012).
Wu. Phytobiologics: Novel natural compounds for improving enteric health in nursing pigs. American association of swine veterinarians 207-210 (2013).

* cited by examiner

|  | T1 | Control 2 | T3 | T4 | Control 5 | T6 | T7 | T8 | Control 9 | T10 |
|---|---|---|---|---|---|---|---|---|---|---|
| Sow ID | LY325 | LY421 | LY386 | LY521 | LY410 | LY350 | LD418 | LY385 | LD430 | LY460 |
| Farrow date | 2/11 | 3/11 | 3/11 | 3/11 | 4/11 | 4/11 | 4/11 | 5/11 | 6/11 | 6/11 |
| Breed | Cross | Cross | Cross | Cross | Cross | Cross | Cross | Cross | Cross | Cross |
| Parity | 6 | 3 | 4 | 2 | 3 | 5 | 6 | 4 | 3 | 2 |
| Born alive | 10 | 8 | 10 | 7 | 10 | 9 | 12 | 11 | 7 | 9 |
| 1st-7 day GI * | ++ | +++ | ++ | + | ++ | + | + | + | ++ | + |
| 8th-14 day GI | + | + | + | − | + | − | + | + | + | + |
| Survivors | 10 | 7 | 9 | 7 | 8 | 8 | 12 | 10 | 7 | 9 |

- GI disorder diarrhea index   + mild   ++ moderate   +++ severe

FIG. 1B

Comparison of Minimum Inhibitory Concentrations (ug/ml) @10³ – 10⁵ CFU Bacteria

| | FURA-P03 herbal oils | Methyl paraben Cosmetic preservative | Poloxol pesticide | Kathon Industrial germicide | Benzal-konium Chloride antiseptic | Rifaxa-mm antibiotic | Triclosan germicide |
|---|---|---|---|---|---|---|---|
| E. Coli | 1,250 | 1,250 | * | 8 | 50 | 128 | 5 |
| Pseudomonas A | 5,000 | 2,500 | 12 | 5 | 250 | >8 | >300 |
| Staphylococcus A | 2,500 | 5,000 | * | 2 | 0.5 | >8 | 0.1 |

FIG. 2

| Bacterium species | Concentration (dry plant wt. equiv) | | | | | | | | | | |
|---|---|---|---|---|---|---|---|---|---|---|---|
| (µl/ml or ppm) | 500 / 750 | 250 / 375 | 125 / 188 | 62.5 / 94 | 31.3 / 47 | 15.6 / 23 | 7.81 / 12 | 3.9 / 6 | 1.95 / 3 | 0.98 / 1.5 | 0.49 / 0.74 |
| *Escherichia coli* | − | − | − | − | − | − | − | − | + | + | + |
| *Salmonella enterica st. Typh.* | + | − | − | − | − | − | + | + | + | + | + |
| *Staphylococcus aureus* | − | − | − | − | − | − | − | − | + | + | + |
| *(MRSA) Staphylococcus aureus* | − | − | − | − | − | − | − | − | + | + | + |
| *Pseudomonas aeruginosa* | − | − | − | − | − | − | − | + | + | + | + |
| *Listeria monocytogenes* | − | − | − | − | − | − | + | + | + | + | + |
| *Pasteurella multocida* | − | − | − | − | − | − | − | + | + | + | + |
| *Proteus vulgaris* | − | − | − | − | − | + | + | + | + | + | + |
| *Klebsiella pneumoniae* | − | − | − | − | − | − | − | + | + | + | + |
| *Bacillus cereus* | − | − | − | − | − | − | − | − | + | + | + |
| *Bordetella brochiseptica* | − | − | − | − | − | − | − | − | + | + | + |

FIG. 3

PEARL effect on
Swine Vesicular Disease Virus

— Virus Titer

Grazix Concentration (ug/ml plant wt equiv)

FIG. 4

METHOD OF TREATING DAMAGED MUCOSAL OR GASTROINTESTINAL TISSUE BY ADMINISTERING A COMPOSITION COMPRISING A MIXTURE OF POMEGRANATE AND GREEN TEA EXTRACTS AND RELEASABLY BOUND HYDROGEN PEROXIDE

BACKGROUND

1. Field of the Invention

The teachings provided herein relate to site-activated binding systems that selectively increase the bioctivity of phenolic compounds at target sites.

2. Description of Related Art

Some phenolic compounds, such as the polyphenols, are considered beneficial for use as antioxidants in animals, such as humans, due to their ability to scavenge unwanted reactive oxygen species in vivo. Such reactive oxygen species can include, for example, singlet oxygen, peroxynitrite, and hydrogen peroxide. This ability to scavenge these reactive oxygen species can affect cell-to-cell signaling, receptor sensitivity, inflammatory enzyme activity and even gene regulation. An antioxidant molecule can, for example, inhibit the oxidation of molecules and are characterized as having a multiplicity of polar moieties that form bonds with oxidizers such as hydrogen peroxide.

Nutritionists have long-recognized the unique health benefits of "live" uncooked fruits and vegetables in the diet. The main source of polyphenols for humans is currently dietary, since they are found in a wide array of phytochemical-bearing foods. For example, honey; most legumes; fruits such as apples, blackberries, blueberries, cantaloupe, cherries, cranberries, grapes, pears, plums, raspberries, and strawberries; and vegetables such as broccoli, cabbage, celery, onion and parsley are rich in polyphenols. red wine, chocolate, green tea, olive oil, argan oil, bee pollen and many grains are sources of these compounds. It is well known that many plant polyphenols ingested or otherwise introduced to animal physiology vary greatly in bioavailability and potency. Moreover, many examples of traditional medicines using living or freshly harvested plant materials have only short lived potency. In addition, all current extraction methods including solvent, reflux heating, sonication, maceration and microwave techniques disrupt intracellular structures, triggering mixing of oxidoreductase enzymes with polyphenols. The polyphenols typically oxidize in the process and have a tendency to autopolymerize or complex indiscriminately with other extracted compounds, destroying significant bioactive potential in a short period of time. Another problem is that many medicinally useful polyphenol compounds also have poor bioavailability. Oxidized polyphenols typically have increased astringent binding activity but also have the tendency to complex indiscriminately with body tissues, body fluids, or foods in the digestive tract. In addition, another problem is that bioactivation of the phenolic compounds requires reactive oxygen species and, in some embodiments, the target site is an anaerobic physiologic environment, and the phenolic compound has difficulty activating.

As a result of at least the above, studies have failed to demonstrate definitive health benefits from dietary supplementation with antioxidants, such as polyphenols. Others have even shown negative effects, including toxic effects from an excessive ingestion of an antioxidant in an attempt to achieve the desired effects. And, most studies, at best, have shown a low bioavailability and rapid excretion of orally ingested antioxidant polyphenol supplements from in vivo systems. As such, the art has still not found an effective way to utilize the health improving potential of these natural phenolic compounds.

One of skill would appreciate having a broad spectrum system to bind compromised tissues, irritants and pathogens that includes these seemingly desirable phenolic compounds, particularly a system that (i) is stable, or at least substantially stable, for storage or administration; (ii) selectively bioactivates the binding system at a target site without significant indiscriminate complexing in undesirable locations; (iii) functions as an astringent, an antitoxin, an antimicrobial, an antinflammatory, an anti-infectant, and the like, reacting with pathogens, their virulence factors, pro-inflammatory compounds and damaged host tissues; and, (iv) functions surprisingly well in small amounts on dermal, mucosal, or in the GI tract tissue of an animal subject, whether human or non-human, aeorobic or anaerobic environments, to target and bind or exclude unwanted materials to treat health conditions, maintain health, and supplement the health and nutrition of the subject.

SUMMARY

The teachings provided herein generally relate to site-activated binding systems that selectively increase the bioactivity of phenolic compounds at a target site.

The teachings include a binding system that selectively increases the bioactivity of phenolic compounds at a target site. In some embodiments, the system can include a phenolic compound component and a reactive oxygen species component. The phenolic compound component can comprise a tannin having a molecular weight ranging from about 500 Daltons to about 4000 Daltons; and, the reactive oxygen species component can comprise hydrogen peroxide. In some embodiments, the hydrogen peroxide can be releasably bound to the tannin at a tannin:peroxide weight ratio (a molar weight ratio) that ranges from about 1:1000 to about 10:1. In some embodiments, the weight ratio of the tannin:peroxide ranges from about 1:1 to about 1:50. And, in some embodiments, the binding system is bioactivated at a target site having an oxidoreductase enzyme that is expressed in response to a tissue damage. In these embodiments, the phenolic compound component can bind to the target site selectively. Moreover, in some embodiments, the binding system contains no, or substantially no, unbound hydrogen peroxide prior to the bioactivating at the target site. The teachings also include a pharmaceutical formulation comprising the binding systems taught herein and a pharmaceutically acceptable excipient.

In some embodiments, the binding molecule comprises a hydrolysable tannin. In some embodiments, the binding molecule comprises a condensed tannin. And, in some embodiments, the binding molecule comprises a combination of a hydrolysable tannin and a condensed tannin.

In some embodiments, the phenolic compound component comprises a flavanol. In some embodiments, the phenolic compound component comprises a catechin. And, in some embodiments, the phenolic compound component comprises gallic acid, epigallic acid, or a combination thereof.

The target site can be a damaged tissue of a subject. As such, the teachings include a method of treating a damaged dermal, mucosal, or gastrointestinal tissue. In some embodiments, the method includes administering an effective amount of a binding system taught herein to the damaged tissue of the subject. In some embodiments, the binding system functions as an antitoxin when bioactivated at the target site of the damaged tissue and assists in the healing of the damaged tissue by inactivating toxic compounds at the target site.

The teachings are also directed to a method of treating a damaged dermal, mucosal, or gastrointestinal tissue. In some embodiments, the method can comprise administering an effective amount of a binding systema taught herein to the damaged tissue of the subject. The binding system can function as an antimicrobial when bioactivated at the target site of the damaged tissue and assist in the healing of the damaged tissue by inactivating compounds that promote infection at the target site.

The teachings are also directed to a method of treating a gastrointestinal condition. In some embodiments, the method can comprise administering an effective amount of a binding system taught herein to the gastrointestinal tract of the subject. The binding system can function as an astringent, an anti-toxin, an anti-inflammatory, or an antimicrobial, for example, when bioactivated at the target site of the damaged tissue and assists in the healing of the damaged tissue by inactivating compounds that promote the condition at the target site.

The teachings are also directed to a method of treating acute diarrhea in a subject. In some embodiments, the methods comprise orally administering an effective amount of a binding system taught herein to the subject. The binding system can prevent, inhibit, or ameliorate a symptom of acute diarrhea in the subject when compared to a second subject in a control group in which the binding system was not administered. In some embodiments, the symptom is selected from the group consisting of a stool score, heartburn, indigestion, urgency of defecation, nausea, vomiting, stomach pain, and bloating.

The teachings are also directed to a method of promoting weight gain in a subject. In some embodiments, the method comprises orally administering an effective amount of a binding system taught herein to the subject as a supplement to the diet of the subject. The binding systems can increase the feed conversion ratio of the subject when compared to a second subject in a control group in which the binding system was not administered.

The teachings are also directed to a method of treating irritable bowel syndrome in a subject. In some embodiments, the method comprises orally administering an effective amount of a binding system taught herein to the subject. The binding system can prevent, inhibit, or ameliorate the symptoms of irritable bowel syndrome in the subject when compared to a second subject in a control group in which the binding system was not administered. In some embodiments, the symptom is selected from the group consisting of a stool score, heartburn, indigestion, urgency of defecation, nausea, vomiting, stomach pain, and bloating.

The teachings are also directed to a method of treating an inflammatory bowel disease in a subject. In some embodiments, the method comprises orally administering an effective amount of a binding system taught herein to the subject. The binding system can prevent, inhibit, or ameliorate the symptoms of inflammatory bowel disease in the subject when compared to a second subject in a control group in which the binding system was not administered. In some embodiments, the symptom is selected from the group consisting of a stool score, heartburn, indigestion, urgency of defecation, nausea, vomiting, stomach pain, and bloating.

The teachings are also directed to a method of treating food poisoning in a subject. In some embodiments, the method comprises orally administering an effective amount of a binding system taught herein to the subject. The binding system can prevent, inhibit, or ameliorate the symptoms of food poisoning in the subject when compared to a second subject in a control group in which the binding system was not administered. In some embodiments, the symptom is selected from the group consisting of a stool score, heartburn, indigestion, urgency of defecation, nausea, vomiting, stomach pain, and bloating.

The teachings are also directed to a method of treating a wound on a tissue of a subject. In some embodiments, the method comprises administering an effective amount of a binding system taught herein to a wound of the subject. The binding system can enhance the rate of healing in the subject when compared to a second subject in a control group in which the binding system was not administered. In some embodiments, the wound is to a dermal tissue, mucosal tissue, or gastrointestinal tissue.

The teachings are also directed to a method of improving the gastrointestinal health of in a subject. In some embodiments, the method comprises orally administering a binding system taught herein, wherein, the binding system improves the gastrointestinal health in the subject when compared to a second subject in a control group in which the binding system was not administered.

The teachings are also directed to a stabilized reagent pair for aqueous transport to a target site. In some embodiments, the reagent pair comprises a tannin having a molecular weight ranging from about 500 Daltons to about 4000 Daltons; and, hydrogen peroxide. The hydrogen peroxide can be hydrogen bonded to the tannin at a tannin:peroxide weight ratio that ranges from about 1:1000 to about 10:1; the binding system can be bioactivated at a target site having an oxidoreductase enzyme; and, the binding molecule binds to the target site.

The teachings are also directed to a pharmaceutical formulation comprising the a reagent pair taught herein, and a pharmaceutically acceptable excipient. The tannin can comprise a catechin, and the tannin:peroxide ratio can ranges from about 1:10 to about 1:50. In some embodiments, the oxidoreductase can comprise a peroxidase; and, there can be no, or substantially no, unbound hydrogen peroxide in the formulation.

One of skill reading the teachings that follow will appreciate that the concepts can extend into additional embodiments that go well-beyond a literal reading of the claims, the inventions recited by the claims, and the terms recited in the claims.

BRIEF DESCRIPTION OF THE FIGURES

FIGS. 1A and 1B illustrate the surprising results of adding the binding system to the drinking water of piglets, according to some embodiments.

FIG. 2 shows the minimal inhibitory concentration (MIC) tests for a composition of 50/50 pomegranate-green tea extract binding system with hydrogen peroxide at a ratio of 10:1 for the hydrogen peroxide:plant compound (molar wt/dry wt). compared to the MIC for other common antimicrobial compounds taken from published data, according to some embodiments.

FIG. 3 shows the binding system's the effective inhibition of a broad spectrum of bacteria by the binding system, according to some embodiments.

FIG. 4 shows effective reduction of virus maintaining the host cell culture viability, according to some embodiments.

FIGS. 5A and 5B are studies showing significant elevation of polymixin B inhibition, according to some embodiments.

Figure 6A:
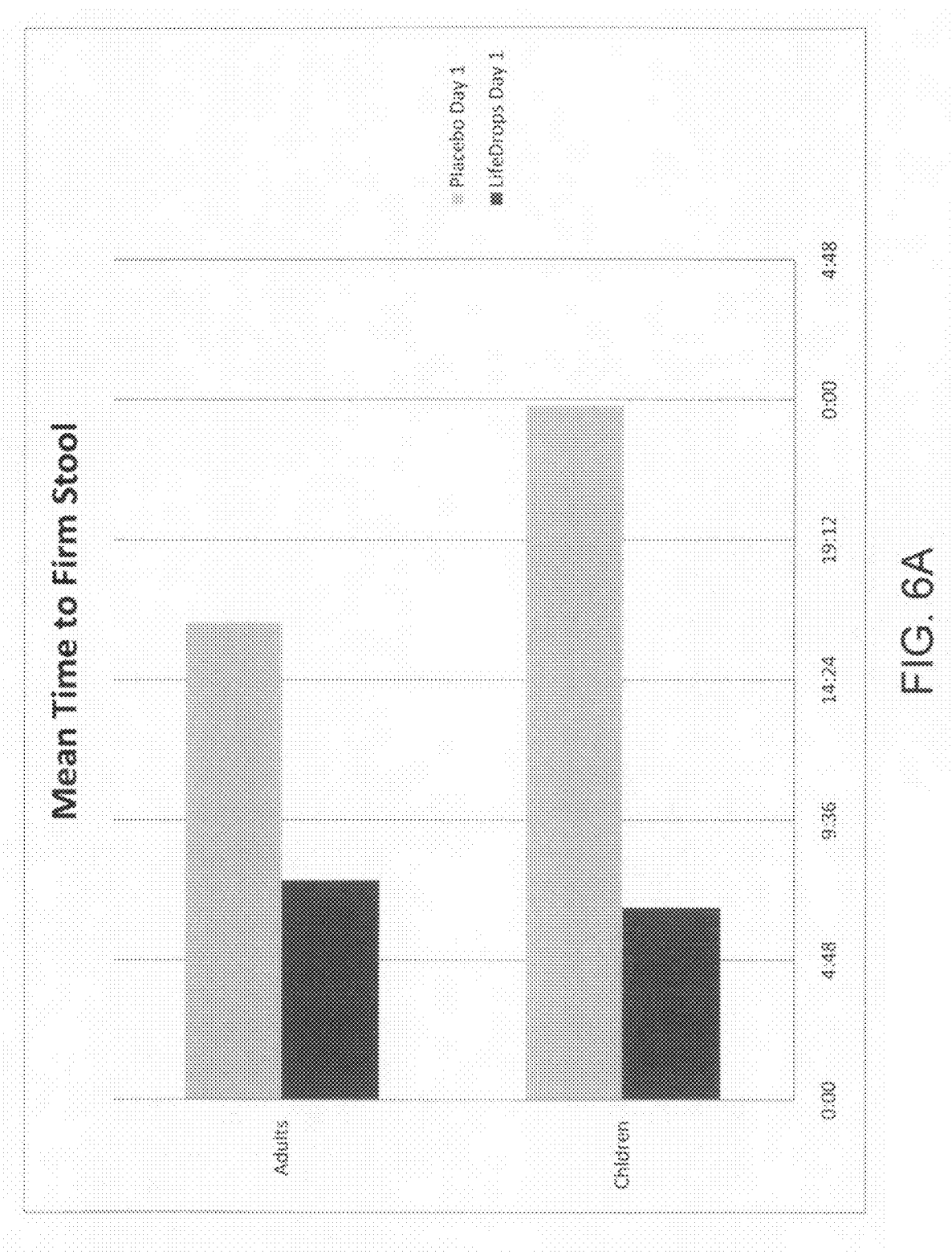
Figure 6B:
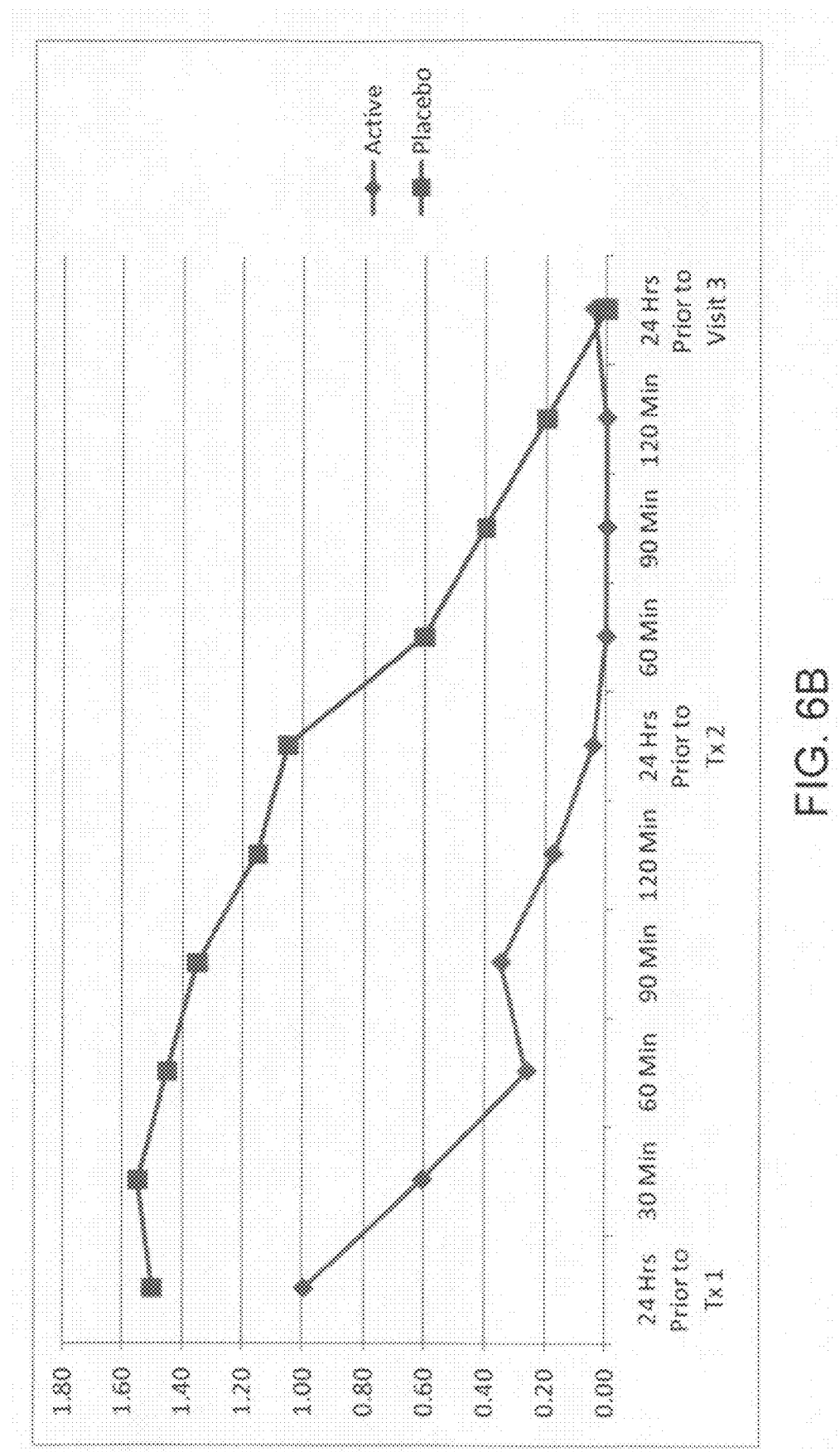
Figure 6C:
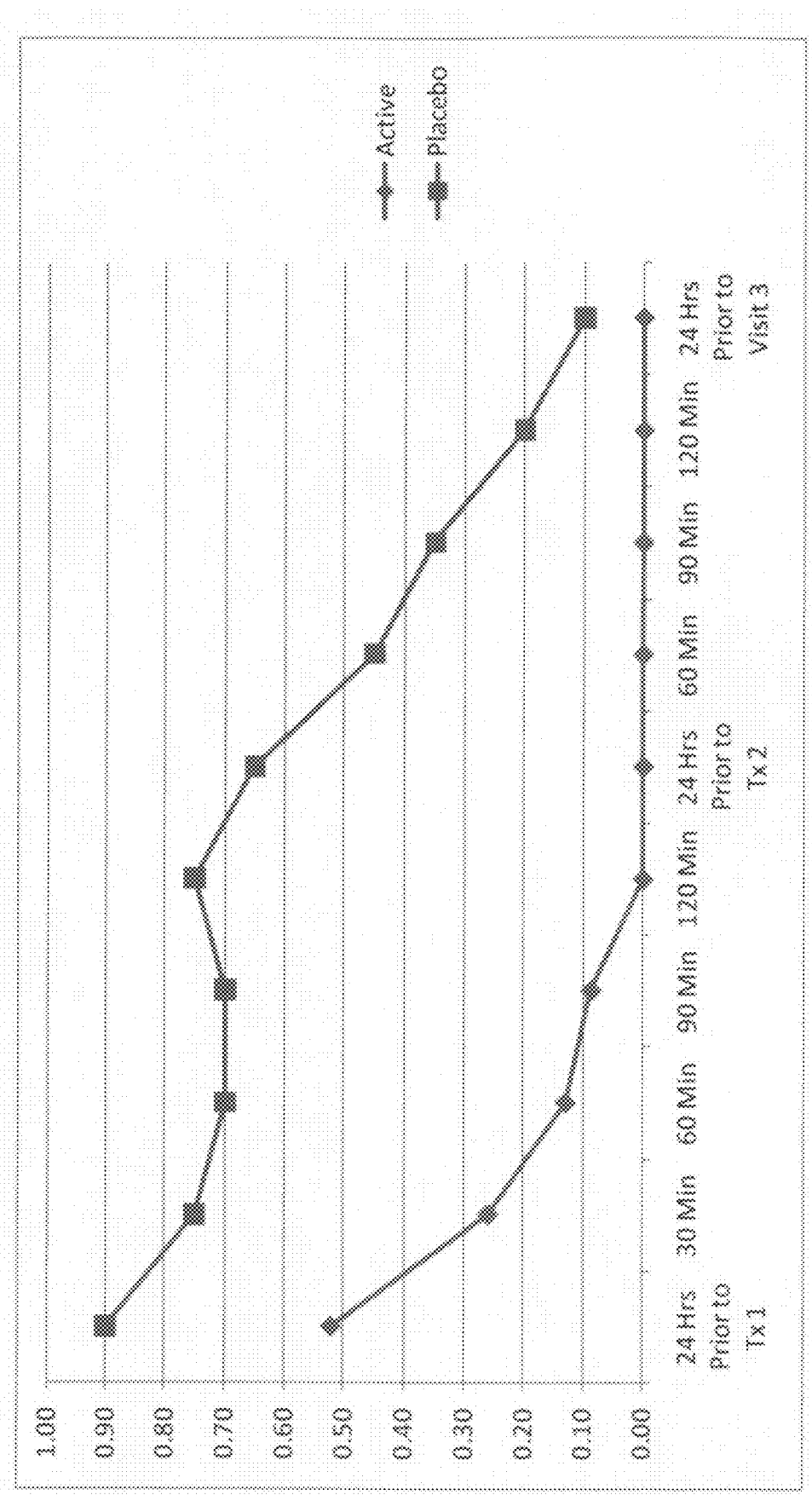
Figure 6D:
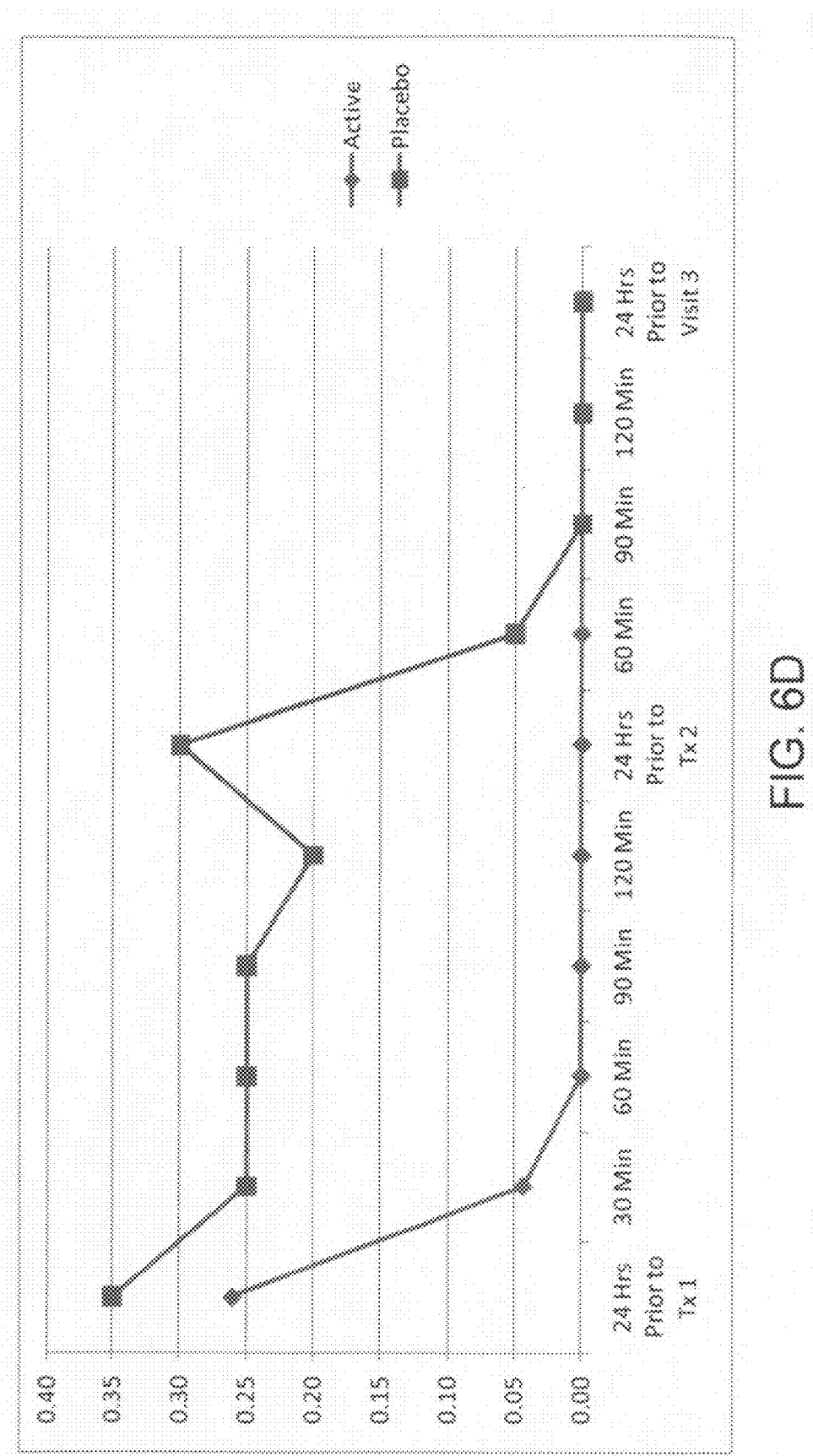
Figure 6E:
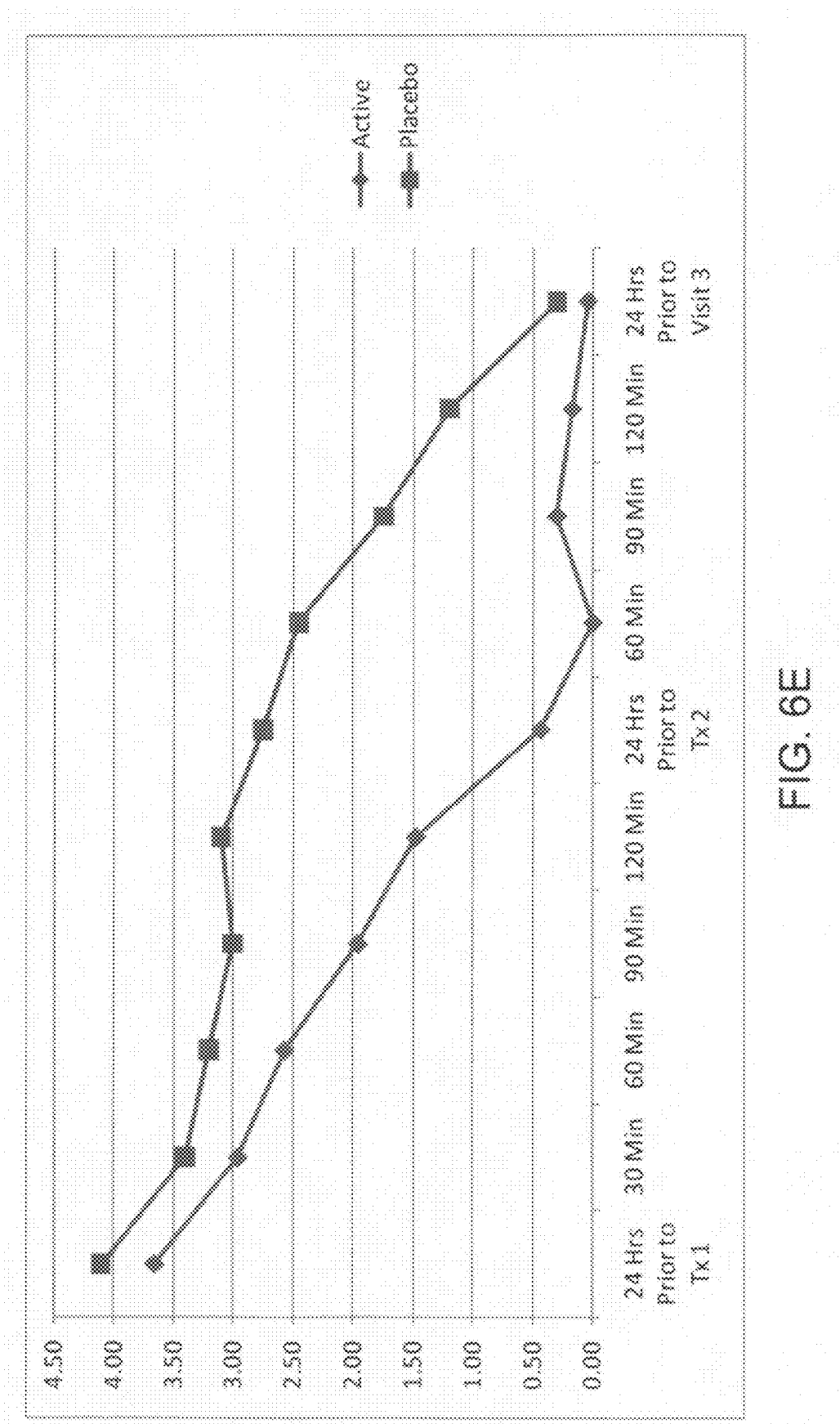
Figure 6F:
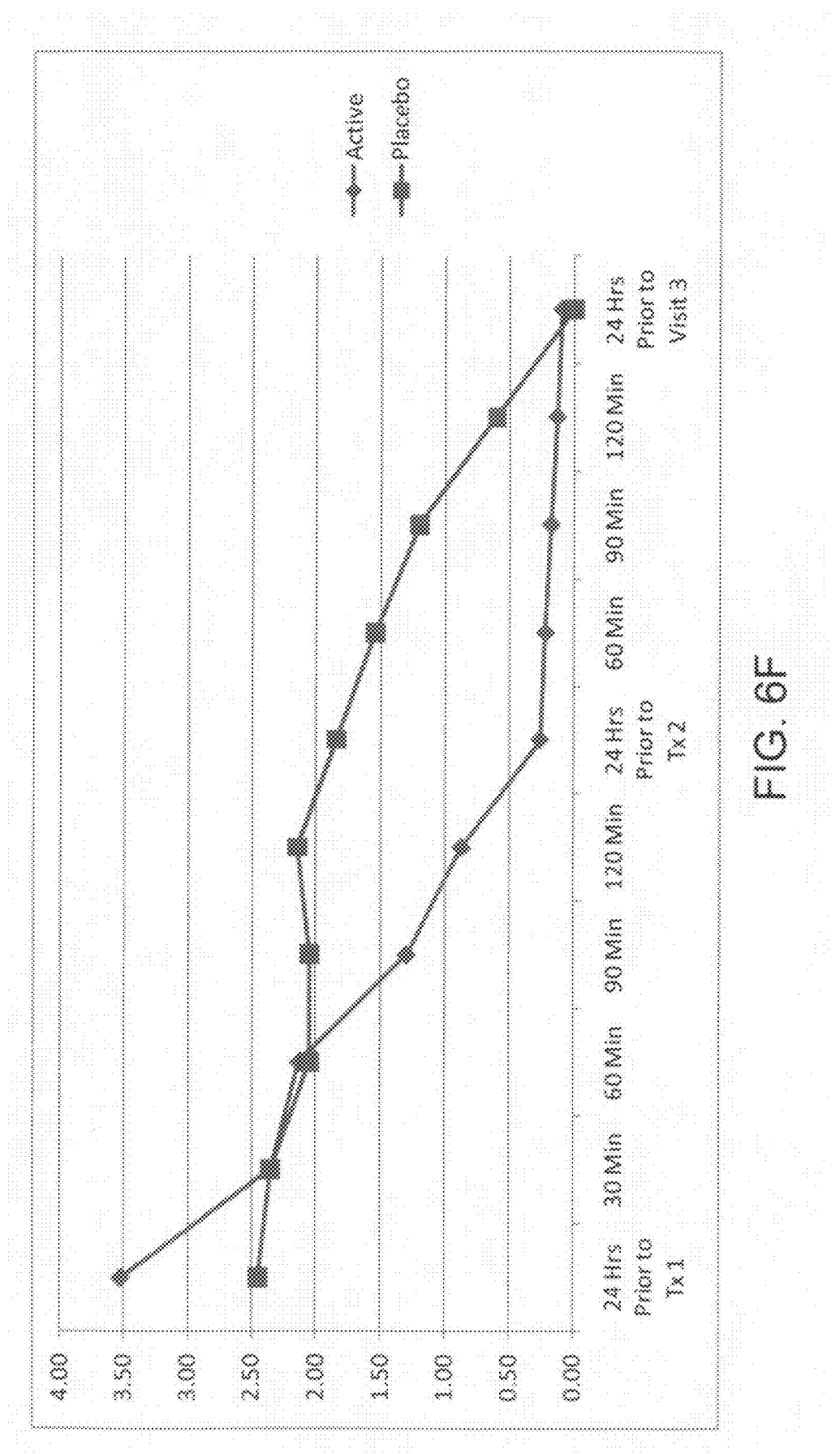

FIGS. 6A and 6F show the rapid resolution of acute watery diarrhea in 86 subjects, according to some embodiments.

DETAILED DESCRIPTION

The teachings provided herein generally relate to site-activated binding systems that selectively increase the bioactivity of phenolic compounds at a target site. More particularly, the systems taught here include a phenolic compound bound to a reactive oxygen species, wherein the phenolic compound and the reactive oxygen species react at a target area in the presence of an oxidoreductase enzyme to provide a site-specific bioactivation of the binding system.

Without intending to be bound by any theory or mechanism of action, the phenolic compounds taught herein are selected to form multiple hydrogen bonds with a reactive oxygen species to form a binding system that is deliverable to a target site as a stable, or substantially stable, structure. The structure has a targeted and enhanced effect from the selective and localized, site-activation of the binding pair at the target site when compared to the effect observed from administration of the phenolic compound alone. Such a composition can be delivered to a target site, for example, in a polar solution such as water or an alcohol. In some embodiments, the reactive oxygen species is hydrogen peroxide, and at least a substantial amount of the hydrogen peroxide remains bound, and thus stable or substantially stable, with the phenolic compound.

The teachings include a binding system that selectively increases the bioactivity of phenolic compounds at a target site. In some embodiments, the system can include a phenolic compound component and a reactive oxygen species component. The phenolic compound component can comprise a tannin having a molecular weight ranging from about 500 Daltons to about 4000 Daltons; and, the reactive oxygen species component can comprise hydrogen peroxide. In some embodiments, the hydrogen peroxide can be releasably bound to the tannin at a tannin:peroxide weight ratio (a molar weight ratio) that ranges from about 1:1000 to about 10:1. In some embodiments, the weight ratio of the tannin:peroxide ranges from about 1:1 to about 1:50. And, in some embodiments, the binding system is bioactivated at a target site having an oxidoreductase enzyme that is expressed in response to a tissue damage. In these embodiments, the phenolic compound component can bind to the target site selectively. Moreover, in some embodiments, the binding system contains no, or substantially no, unbound hydrogen peroxide prior to the bioactivating at the target site. The teachings also include a pharmaceutical formulation comprising the binding systems taught herein and a pharmaceutically acceptable excipient.

In some embodiments, the binding molecule comprises a hydrolysable tannin. In some embodiments, the binding molecule comprises a condensed tannin. And, in some embodiments, the binding molecule comprises a combination of a hydrolysable tannin and a condensed tannin.

In some embodiments, the phenolic compound component comprises a flavanol.

In some embodiments, the phenolic compound component comprises a catechin. And, in some embodiments, the phenolic compound component comprises gallic acid, epigallic acid, or a combination thereof.

The terms "composition," "compound," "binding system," and "binding pair," can be used interchangeably in some embodiments and, it should be appreciated that a "formulation" can comprise a composition, compound, binding system or binding pair presented herein. Likewise, in some embodiments, the binding systems can also be referred to as an "agent," a "bioactive agent," or a "supplement" whether alone, in a pharmaceutically acceptable composition or formulation, and whether in a liquid or dry form. Moreover, the term "bioactivity" can refer to the increase in function of the phenolic compound that occurs through the use of the binding systems provided herein, where the function can refer to an increase in the binding of the phenolic compound at a target site upon bioactivation.

One of skill will appreciate that the term "bind," "binding," "bound," "attached," "connected," "chemically connected," or "chemically attached" can be used interchangeably, in some embodiments. Such terms can refer to any chemical bonding mechanism known to one of skill, such as covalent, ionic, dipole-dipole interactions, London dispersion forces, and hydrogen bonding, for example. In some embodiments, the binding system comprises a phenolic compound sharing hydrogen bonds with a reactive oxygen species, such as hydrogen peroxide. In some embodiments, the phenolic compound can comprise a polyphenol that covalently binds to an amino acid or polyol.

In some embodiments, the term "target site" can be used to refer to a select location, that provides, either endogeneously or exogeneously, an oxidoreductase enzyme that can bioactivate a binding system taught herein upon contact with the binding system. In some embodiments, the target system can be in or on a subject. In some embodiments, the target site can be located on or in a plant or a non-living material. One of skill will appreciate that the target can include any site of action in which the phenolic compound can be site-activated by an oxidoreductase enzyme that is available at the site. The oxidoreductase enzyme can be produced endogeneously by a tissue at a target site, produced endogeneously by a microbe, introduced exogenously to the target site, include more than one enzyme, co-enzyme, catalyst, or cofactor, or a combination thereof.

The target site can be a damaged tissue of a subject. As such, the teachings include a method of treating a damaged dermal, mucosal, or gastrointestinal tissue. In some embodiments, the method includes administering an effective amount of a binding system taught herein to the damaged tissue of the subject. In some embodiments, the binding system functions as an antitoxin when bioactivated at the target site of the damaged tissue and assists in the healing of the damaged tissue by inactivating toxic compounds at the target site.

One of skill will appreciate that the binding systems should remain stable, or at least substantially stable, until useful or activated, and this can relate to a shelf life, or a time between creation of the binding pair and administration of the binding pair, or some combination thereof. In some embodiments, the binding pair is stable, or substantially stable, when usable as intended within a reasonable amount of time. In some embodiments, the binding pair should be usable within a reasonable time from the making of the binding pair to the administration of the binding pair and, in some embodiments, the binding pair should have a reasonable commercial shelf life.

The binding pair can be considered as "stable" if the binding pair loses less than 10% of it's original oxidation potential, and this can be measured by comparing it's oxidation potential after making the binding pair to the time of administration, and this can include a reasonable shelf life, in some embodiments. In some embodiments, the binding pair can be considered as stable if the binding pair loses less than 5%, 3%, 2%, or 1% of it's original oxidation potential when comparing it's oxidation potential after making the binding pair to the time of administration, and this can include a reasonable shelf life, in some embodiments.

The binding pair can be considered as "substantially stable" if the binding system loses greater than about 10% of it's original oxidation potential, as long as the composition can perform it's intended use to a reasonable degree of efficacy. The loss can be measured, as above, by measured by comparing it's oxidation potential after making the binding pair to the time of administration, and this can include a reasonable shelf life, in some embodiments. In some embodiments, the binding pair can be considered as substantially stable if a reactive oxygen species loses greater than about 12%, about 15%, about 25%, about 35%, about 45%, about 50%, about 60%, or even about 70% of it's original oxidation potential. The loss may be measured by measured by comparing it's oxidation potential after making the binding pair to the time of administration, and this can include a reasonable shelf life, in some embodiments.

In some embodiments, the binding pair is stable or substantially stable, if useful for a period ranging from about 2 minutes to about 10 minutes, from about 10 minutes to about 30 minutes, from about 30 minutes to about one hour, from about one hour to about 12 hours, from about 12 hours to about 1 day, from about one day to about one week, from about 1 week to about 1 month, from about 1 month to about 3 months, from about 1 month to a year, from 3 months to a year, from 3 months to 2 years, from 3 months to 3 years.

In some embodiments, the binding pair is stable, or substantially stable for a period ranging from about 1 second to about 2 days, from about 1 second to about 5 seconds, from about 5 seconds to about 10 seconds, from about 10 seconds to about 30 seconds, from about 30 seconds to about 1 minute, from about 1 minute to about 5 minutes, from about 5 minutes to about 15 minutes, from about 15 minutes to about 30 minutes, from about 30 minutes to about an hour, from about 1 hour to about 12 hours, from about 12 hours to about 1 day, from about 1 day to about 2 days, or any range therein. In some embodiments, the binding pair is stable, or substantially stable for up to about 2 days, about 1 week, or any range therein.

The stable structure of the binding system provides for, over an extended period of time, an improved binding between the phenolic compound and the target when compared to the binding of the phenolic compound and the target in a diffuse solution. As such, the site-activated binding systems generally increase the bioactivity of the phenolic compounds at the target sites to a surprising degree, which has been shown to result in a surprising level of bioactivity and overall potency at target sites.

One of skill will appreciate that the phenolic compound in the binding system can be any phenolic compound that functions consistent with the teachings provided herein, and there are at least several thousand phenolic compounds known to those of skill. As such, the teachings provided herein can only include examples of the general concepts rather than a comprehensive listing of all possibilities and permutations of the systems that are enabled by the teachings. Likewise, one of skill will appreciate that there are numerous reactive oxygen species that can be used in the systems taught herein, as long as the reactive oxygen species function consistent with such teachings.

Generally speaking, phenolic compounds are those that include a hydroxyl group bonded directly to an aromatic hydrocarbon group. The simplest of the class is phenol ($C_6H_5OH$). One of skill will appreciate that the entire class of phenolic compounds is very large, and that not all of the phenolic compounds can be used with the teachings provided herein. For example, phenol is inoperable with the teachings provided herein, as it cannot crosslink or polymerize with itself under the conditions in which the binding systems are used. However, the person of skill will also appreciate that the teachings provided herein can be used with many compounds within the entire class of phenolic corn pounds.

In some embodiments, the phenolic compounds in the binding systems (i) have phenolic hydroxyl groups that are oxidizable in the presence of a reactive oxygen species and an oxidoreductase enzyme, (ii) can crosslink or polymerize with other phenolic compounds in the systems; and (iii) are soluble in a polar liquid, such as water or an alcohol, for example, or at least moderately soluble. And, in some embodiments, the phenolic compounds should also be (iv) non-toxic to a subject upon administration.

In some embodiments, the phenolic compound has at least one aryl group, or arene moiety, and at least two polar aromatic groups, such as aromatic hydroxyl groups. In some embodiments, the polar aromatic groups can be, for example, hydroxyl, amine, amide, acyl, carboxy, or carbonyl. In some embodiments, the phenolic compound has at least two aryl groups, and at least two hydroxyl groups. In some embodiments, the phenolic compounds can be naturally occurring, such as from a plant or other natural product. And, in some embodiments, the phenolic compounds can be synthetically or semi-synthetically produced. The compounds can be simple monomers, oligomers, or polymers. The polymers can be in the class of polyphenols or polymeric phenols, where one of skill will understand that the general difference is typically that polyphenols generally do not have a repeating unit, whereas polymeric phenols do. There are exceptions, however, such that groups of polyphenols and polymeric phenols can overlap. In most embodiments, the phenolic compound used in the binding system can be any phenolic compound taught herein, or any prodrugs, codrugs, metabolites, analogs, homologues, congeners, derivatives, salts, solvates, and combinations thereof.

In some embodiments, the phenolic compounds bind to hydrogen peroxide to form a binding pair and, in some embodiments, the binding pair remains stable, or substantial stable in water. In some embodiments, the binding pair remains stable, or substantial stable in an alcohol. And, in some embodiments, the binding pair remains stable, or substantial stable, in a polar solvent such as, for example, a saline solution, an an aqueous emulsion, a hydrogel, and the like.

In some embodiments, the phenolic compounds are polyphenols having molecular weights ranging from about 500 to about 4000 Daltons, having from about 12 to about 16 phenolic hydroxyl groups, and having from about five to about seven aromatic rings, for every about 1000 Daltons in molecular weight. In some embodiments, the phenolic compounds function to precipitate alkaloids and proteins. In some embodiments, the phenolic compounds can bind to amino acids, peptides, oligopeptides, polyols, saccharides, or combinations thereof. In some embodiments, the phenolic compounds have at least from about 1 to about 20 polyhydroxylated phenolic units and have at least moderate water solubility.

In some embodiments, the phenolic compounds are polyphenols having molecular weights ranging from about 300 to about 4000 Daltons, having from about 2 to about 16 phenolic hydroxyl groups, and having from about five to about seven aromatic rings, for every about 1000 Daltons in molecular weight. In some embodiments, the phenolic compounds function to precipitate alkaloids and proteins. In some embodiments, the phenolic compounds can bind to amino acids, peptides, oligopeptides, polyols, saccharides, or combinations thereof. In some embodiments, the phenolic compounds have at least from about 1 to about 20 polyhydroxylated phenolic units and have at least moderate water solubility.

In some embodiments, the phenolic compounds are polyphenols having molecular weights ranging from about 500 to about 4000 Daltons, greater than 12 to phenolic hydroxyl groups, and having from about five to about seven aromatic rings, for every about 1000 Daltons in molecular weight. In some embodiments, the phenolic compounds function to precipitate alkaloids and proteins. In some embodiments, the phenolic compounds can bind to amino acids, peptides, oligopeptides, polyols, saccharides, or combinations thereof. In some embodiments, the phenolic compounds have at least from about 1 to about 20 polyhydroxylated phenolic units and have at least moderate water solubility.

The term "solubility" can refer to a concentration of a solute in a solvent, for example, the phenolic compound in water. The concentration can be expressed by mass, for example, mg of the phenolic compound per kg of water at ambient temperature and pressure. This ratio of mg/kg can be used interchangeably with ppm, and ng/kg can be used interchangeably with ppb. In some embodiments, the solubility of the phenolic compound can be higher than about 500,000 ppm or less than about 1 ppm. In some embodiments, the solubility of the phenolic compound range from about 10 ppb to about 500,000 ppm, from about 100 ppb to about 250,000 ppm, from about 1 ppm to about 100,000 ppm, from about 10 ppm to about 50,000 ppm, from about 50 ppm to about 25,000 ppm, from about 100 ppm to about 10,000 ppm, from about 100 ppm to about 100,000 ppm, from about 200 ppm to about 100,000 ppm, from about 250 ppm to about 50,000 ppm, from about 500 ppm to about 25,000 ppm from about 250 ppm to about 10,000 ppm, or any range therein. In some embodiments, the solubility can range from about 1 g/L to about 10,000 g/L, from about 5 g/L to about 5000 g/L, from about 10 g/L to about 3000 g/L, from about 20 g/L to about 2000 g/L, from about 50 g/L to about 1000, g/L, from about 100 g/L to about 500 g/L, or any range therein. For purposes of the teachings provided herein, a compound can be considered to have a low solubility if the solubility is less than about 50 g/L, a moderate solubility if the solublity ranges from about 50 g/L to about 1000 g/L, and a high solubility if the solubility is above about 1000 g/L. In some embodiments, the phenolic compound can have a low solubility. In some embodiments, the phenolic compound can have a moderate solubility. And, in some embodiments, the phenolic compound can have a high solubility.

One of skill will appreciate that the phenolic compounds can still be useful at low solubilities in cases where the solubility is too low to form a true solution. In some embodiments the phenolic compounds can be ground into particles to form a colloidal mixture or suspension that will function consistent with the teachings provided herein. As such, liquid formulations include colloids and suspensions in some embodiments. The formulations can be a dispersed phase mixture in the form of colloidal aerosols, colloidal emulsions, colloidal foams, colloidal dispersions, or hydrosols. In some embodiments, the liquid formulation can include particles having sizes ranging, for example, from about 5 nm to about 200 nm, from about 5 nm to about 500 nm, from about 5 nm to about 750 nm, from about 50 nm to about 1 um. In some embodiments, the liquid formulations can be suspensions, in which the particle size range from about 1 urn to about 10 um, from about 1 um to about 7 um, from about 1 um to about 5 um, or any range therein. In some embodiments, the liquid formulation can include particles having sizes ranging from about 1 nm to about 10 um.

The functionality of a phenolic compound in the teachings herein can, for at least the reason of solubility, depend on molecular weight, alone or in addition to other factors discussed herein such as, for example, extent of hydroxylation, presence and location of ketone or quinine groups, and the presence of other functional groups. In some embodiments, the molecular weights of the phenolic compounds can range from about 110 Daltons to about 40,000 Daltons. In some embodiments, the molecular weights of the phenolic compounds can range from about 200 Daltons to about 20,000 Daltons, from about 300 Daltons to about 30,000 Daltons, from about 400 Daltons to about 40,000 Daltons, from about 500 Daltons to about 10,000 Daltons, from about 1000 Daltons to about 5,000 Daltons, from about 500 Daltons to about 4000 Daltons, from about 500 Daltons to about 3,000 Daltons, from about 300 Daltons to about 2,000 Daltons, from about 110 Daltons to about 30,000 Daltons, from about 200 to about 5000 Daltons, or any range therein.

In some embodiments, the ratio of aromatic rings to molecular weight of the phenolic compounds can range from about five to about seven aromatic rings for every about 1000 Daltons. In some embodiments, the ratio of aromatic rings to molecular weight of the phenolic compounds can range from about 2 to about 10 aromatic rings for every about 1000 Daltons, from about 3 to about 9 aromatic rings for every about 1000 Daltons, from about 4 to about 8 aromatic rings for every about 1000 Daltons, from about 5 to about 7 aromatic rings for every about 1000 Daltons, from about 1 to about 5 for every about 500 Daltons, from about 1 to about 4 for every about 500 Daltons, from about 1 to about 3 for every about 500 Daltons, from about 2 to about 4 for every about 500 Daltons, or any range therein.

One of skill will appreciate that the phenolic compounds should have functional groups that are capable of releasably bonding to a reactive oxygen species, in a stable or substantially stable form, until released upon bioactivation at a target site. In some embodiments, a releasable bond can include any bond other than a covalent bond. In some embodiments, a releasable bond is a hydrogen bond. As such, the phenolic compounds should be capable of forming, for example, a hydrogen bond with a reactive oxygen species upon such bioactivation. In some embodiments, the phenolic compound shares hydrogen bonding with hydrogen peroxide and is released through a bioactivation that occurs when the binding pair comes into contact with an oxidoreductase enzyme or other reducing agent. In some embodiments, the phenolic compound can have functional groups that comprise acyl, amido, amino, carbonyl, carboxyl, hydroxyl, or peroxyl functionality. In some embodiments, the hydrogen bond between the reactive oxygen species and the phenolic compound can include any hydrogen donor and any hydrogen acceptor having an available lone pair of electrons. In some embodiments, the hydrogen acceptor can include, for example a N, O, or F atom, or a combination thereof. In some embodiments, the phenolic compound can have such a functionality, can be derivatized to have such a functionality, can be linked to another compound having such a functionality, can be placed in a carrier having such a functionality, or some combination thereof.

In some embodiments, phenolic compounds can include simple phenols, such as those containing 6 carbons, a C6 structure, and 1 phenolic cycle, such as the benzene alcohols, examples of which include phenol, benzene diols and it's isomers such as catechol, and the benzenetriols. In some embodiments, phenolic compounds can include phenolic acids and aldehydes, such as those containing 7 carbons, a C6-C1 structure, and 1 phenolic cycle, examples of which include gallic acid and salicylic acids. In some embodiments, phenolic compounds can include, for example, tyrosine derivatives, and phenylacetic acids, such as those containing 8 carbons, a C6-C2 structure, and 1 phenolic cycle, examples of which include 3-acetyl-6-methoxybenzaldehyde, tyrosol, and p-hydroxyphenylacetic acid. In some embodiments, phenolic compounds can include hydroxycinnamic acids, phenylpropenes, chromones, such as those containing 9 carbons, a C6-C3 structure, and 1 phenolic cycle, examples of which include caffeic acid, ferulic acids, myristicin, eugenol, umbelliferone, aesculetin, bergenon, and eugenin. In some embodiments, phenolic compounds can include naphthoquinones, such as those containing 10 carbons, a C6-C4 structure, and 1 phenolic cycle, examples of which include juglone and plumbagin. In some embodiments, phenolic compounds can include xanthonoids, such as those containing 13 carbons, a C6-C1-C6 structure, and 2 phenolic cycles, examples of which include mangiferin. In some embodiments, phenolic compounds can include stilbenoids, and anthraquinones, such as those containing 14 carbons, a C6-C2-C6 structure, and 2 phenolic cycles, examples of which include resveratrol and emodin. In some embodiments, phenolic compounds can include chalconoids, flavonoids, isoflavonoids, and neoflavonoids, such as those containing 15 carbons, a C6-C3-C6 structure, and 2 phenolic cycles, examples of which include quercetin, myricetin, luteolin, cyanidin, and genistein. In some embodiments, phenolic compounds can include lignans and neolignans, such as those containing 18 carbons, a C6-C3-C6 structure, and 2 phenolic cycles, examples of which include pinoresinol and eusiderin. In some embodiments, phenolic compounds can include biflavonoids, such as those containing 30 carbons, a $(C6-C3-C6)_2$ structure, and 4 phenolic cycles, examples of which include amentoflavone. In some embodiments, phenolic compounds can include polyphenols, polyphenolic proteins, lignins, and catechol melanins, such as those containing >30 carbons. In these embodiments, the phenolic compounds can have, for example, a $(C6-C3)_n$ structure, a $(C6)_n$ structure, a $(C6-C3-C6)_n$ structure, or some combination thereof, as well as greater than about 12 phenolic cycles. Examples of such embodiments can include, for example, the flavolans, in the class of condensed tannins.

In some embodiments, the phenolic compounds are natural phenols that can be enzymatically polymerized. Derivatives of natural phenols can also be used in some embodiments. These embodiments can include phenolic compounds having less than 12 phenolic groups, such that they can range from monophenols to oligophenols. In some embodiments, the natural phenols are found in plants, have an antioxidant activity, or a combination thereof. Examples of the natural phenols include, for example, catechol- and resorcinol-types (benzenediols) with two phenolic hydroxy groups, and pyrogallol- and phloroglucinol-types (benzenetriols) with three hydroxy groups. Natural phenols may have heteroatom substituents other than hydroxyl groups, ether and ester linkages, carboxylic acid derivatives, or some combination thereof. In some embodiments, the natural phenols include natural phenol drugs and their derivatives. Examples of such drugs include, but are not limited to, anthraquinone drugs, flavone drugs, and flavonol drugs. Examples of anthraquinone drugs include, but are not limited to, aloe emodin, aquayamycin, and diacerein. Examples of flavone drugs include, but are not limited to, ansoxetine and hidrosmin. Examples of flavonol drugs include, but are not limited to, monoxerutin and troxerutin.

In some embodiments, the phenolic compound is a tannin, a polyphenolic phenylpropanoid, or a combination thereof. In some embodiments, the tannin is a hydrolysable tannin, a condensed tannin, or a combination thereof. Hydrolysable tannins can be found, for example, in chinese gall, which is almost pure in that it has no or substantially no condensed tannins. Condensed tannins can be found, for example, in green tea, which is also almost pure that it has no or substantially no hydrolysable tannins.

Examples of hydrolysable tannin can include gallotannic acids, quercitannic acids, ellagitannins, gallotannin, pentagalloyl glucose, galloylquinic acid, galloyl-shikimic acid, and punicalagin. In some embodiments, the hydrolysable tannin is a gallotannin or ellagitannin, and isomers thereof, such as isomers that can precipitate protein. Examples of gallotannins include the gallic acid esters of glucose in tannic acid ($C_{76}H_{52}O_{46}$) and pentagalloyl glucose (PGG), and isomers thereof, such as the isomers of PGG that function to precipitate proteins. Examples of an ellagitannin include castalin and punicalagin. In some embodiments, the tannin is a gallic acid ester having a molecular weight ranging from about 500 Daltons to about 3000 Daltons. In some embodiments, the tannin is a proanthocyanidin having a molecular weight of up to about 20,000 Daltons. In some embodiments, the hydrolysable tannins are derivatives of gallic acid and characterized by a glucose, quinic acid or shikimic acid core with its hydroxyl groups partially or totally esterified with gallic acid or ellagic acid groups. The compounds can have 3 to 12 galloyl residues but may be further oxidatively crosslinked and complex. Hydrolysable tannins can be readily synthesized, for example, to obtain a phenolic compound with a high number of polar functional groups that form multiple, stable hydrogen bonds between the tannin and hydrogen peroxide in the binding system.

It should be appreciated that, while hydrolysable tannins and most condensed tannins are water soluble, some very large condensed tannins are insoluble. In some embodiments, the phenolic compound can comprise a hydrolysable tannin such as, for example, burkinabin C, castalagin, castalin, casuarictin, chebulagic acid, chebulinic acid, corilagin, digallic acid, ellagitannin, gallagic acid, gallotannin, glucogallin, grandinin, hexahydroxydiphenic acid, pentagalloyl glucose, punicalagin alpha, punicalagins, raspberry ellagitannin, roburin A, stenophyllanin A, stenophyllanin A, tannate, tannic acid, tellimagrandin II, terflavin B, or 3,4,5-tri-O-galloylquinic acid.

In some embodiments, the phenolic compound can be a flavonoid which includes several thousand natural phenol compounds. Examples of the flavonoids include the flavonols, flavones, flavan-3ol (catechins), flavanones, anthocyanidins, isoflavonoids, and hybrids of any combination of these compounds. In some embodiments, the phenolic compounds are the hydrolysable tannins such as, for example, gallic acid. In some embodiments, the phenolic compounds are the lignins such as, for example, cinnamic acid. In some embodiments, the phenolic units can be dimerized or further polymerized to form any of a variety of hybrids. For example, ellagic acid is a dimer of gallic acid and forms the class of ellagitannins, or a catechin and a gallocatechin can combine to form theaflavin or the large class of thearubigins found in tea. In another example, a flavonoid and a lignan can combine to form a hybrid, such a flavonolignans.

In some embodiments, the phenolic compound can be a flavan-3ol. Examples include the catechins and the catechin gallates, where the catechin gallates are gallic acid esters of the catechins. In some embodiments, the phenolic compound is a catechin or epicatechin compound (the cis- or trans-isomers). In some embodiments, the phenolic compound is (−)-epicatechin or (+)-catechin. In some embodiments, the phenolic compound is epigallocatechin (EGC) or gallocatechin (EC). In some embodiments, the phenolic compound is a catechin gallate, such as epigallocatechin gallate (EGCG)

In some embodiments, the phenolic compound can be selected from the group of flavones consisting of apigenin, luteolin, tangeritin, flavonols, isorhamnetin, kaempferol, myricetin (e.g., extractable from walnuts), proanthocyanidins or condensed tannins, and quercetin and related phenolic compounds, such as rutin.

In some embodiments, the phenolic compound can be selected from the group of flavanones consisting of eriodictyol, hesperetin (metabolizes to hesperidin), and naringenin (metabolized from naringin).

In some embodiments, the phenolic compound can be selected from the group of flavanols consisting of catechin, gallocatechin and their corresponding gallate esters, epicatechin, epigallocatechin and their corresponding gallate esters, theaflavin and its gallate esters, thearubigins, isoflavone phytoestrogens (found primarily in soy, peanuts, and other members of the Fabaceae family), daidzein, genistein, glycitein, stilbenoids, resveratrol (found in the skins of dark-colored grapes, and concentrated in red wine), pterostilbene (methoxylated analogue of resveratrol, abundant in Vaccinium berries), anthocyanins, cyanidin, delphinidin, malvidin, pelargonidin, peonidin, and petunidin. And, In some embodiments, the phenolic compound can be ubiquinol an electron-rich (reduced) form of coenzyme Q10.

In some embodiments, the phenolic compound can be selected from the group of carotenoid terpenoid consisting of alpha-carotene, astaxanthin (found naturally in red algae and animals higher in the marine food chain, a red pigment familiarly recognized in crustacean shells and salmon flesh/roe), beta-carotene (found in high concentrations in butternut squash, carrots, orange bell peppers, pumpkins, and sweet potatoes), canthaxanthin, lutein (found in high concentration in spinach, kiwifruit and red peppers), lycopene (found in high concentration in ripe red tomatoes and watermelons) and zeaxanthin (the main pigment found in yellow corn, also abundant in kiwifruit).

In some embodiments, the phenolic compound can be selected from the group of phenolic acids and their esters consisting of chicoric acid (another caffeic acid derivative, is found only in the medicinal herb echinacea purpurea), chlorogenic acid (found in high concentration in coffee (more concentrated in robusta than arabica beans, blueberries and tomatoes, and produced from esterification of caffeic acid), cinnamic acid and its derivatives, such as ferulic acid (found in seeds of plants such as in brown rice, whole wheat and oats, as well as in coffee, apple, artichoke, peanut, orange and pineapple), ellagic acid (found in high concentration in raspberry and strawberry, and in ester form in red wine tannins), ellagitannins (hydrolysable tannin polymer formed when ellagic acid, a polyphenol monomer, esterifies and binds with the hydroxyl group of a polyol carbohydrate such as glucose), gallic acid (found in galinuts, sumac, witch hazel, tea leaves, oak bark, and many other plants), gallotannins (hydrolysable tannin polymer formed when gallic acid, a polyphenol monomer, esterifies and binds with the hydroxyl group of a polyol carbohydrate such as glucose), rosmarinic acid (found in high concentration in rosemary, oregano, lemon balm, sage, and marjoram), and salicylic acid (found in most vegetables, fruits, and herbs; but most abundantly in the bark of willow trees, from where it was extracted for use in the early manufacture of aspirin).

In some embodiments, the phenolic compound can be selected from the group of nonflavonoid phenolics consisting of curcumin (has low bioavailability, because, much of it is excreted through glucuronidation, but bioavailability can be substantially enhanced by solubilization in a lipid (oil or lecithin), heat, addition of piperine, or through nanoparticularization, flavonolignans, for example, silymarin which is a mixture of flavonolignans extracted from milk thistle), eugenol and xanthones (mangosteen, for example, is purported to contain a large variety of xanthones, some of which, like mangostin are believed to be present only in the inedible shell).

In some embodiments, the phenolic compound can have a low molecular weight (less than about 400 Daltons), selected from the group consisting of caffeic acid, gentisic acid, protocatechuic acid, phenylacetic acid, gallic acid, phloroglucinol carboxylic acid, and derivatives thereof. Such compounds can form a sufficiently soluble binding pair, and their relatively high hydroxyl group to molecular weight ratio creates favorable conditions for obtaining the intermolecular hydrogen bonds desired for the binding systems.

In some embodiments, the phenolic compounds can be from a natural extract, such as an extract of a plant or other natural product. See, for example, U.S. Published Patent Application Nos. 20100158885 and 20110070198, each of which is hereby incorporated by reference herein in its entirety. Those skilled in the art of such extracts will understand that extracts of plant materials are not typically pure in one type of phenolic compound. Plant tannin extracts, for example, typically comprise heterogenous mixtures and derivatives of the above classes.

In some embodiments, the phenolic compound is extracted from a whole or partial plant tissue selected from the group consisting of seeds and fruits; ovaries; juice; pulp; galls; husks; bark; stems; leaves; flowers; sheaths; hulls; sprouts; bulbs; hips; tubers; roots of grains; grasses; legumes; trees; vegetables; medicinal herbs; tea leaves; algaes; marine plants; and, forages. One of skill will appreciate that the type and content of phenolic compound obtained can be expected to vary with the species, season, geographical location, cultivation, and storage.

Generally speaking, the reactive oxygen species include those that can facilitate the oxidation of a phenol hydroxyl group to a ketone group and form a reactive quinone structure upon the bioactivation. In some embodiments, the reactive oxygen species can include hydrogen peroxide, superoxide anion, singlet oxygen, or a hydroxyl radical. In some embodiments, the reactive oxygen species is hydrogen peroxide. In some embodiments, the reactive oxygen species is hydrogen peroxide.

In some embodiments, the reactive oxygen species is hydrogen peroxide or a material that release hydrogen peroxide including, but not limited to, hydration of adducts of hydrogen peroxide such as carbamide peroxide, magnesium peroxide, and sodium percarbonate; amino perhydrates; superoxide dismutase decomposition of ozone, superoxides or superoxide salts; glucose oxidase and glucose, aqueous dilution of honey; $H_2O_2$ production by lactobacillus; catalytic quinone hydrogenation; superoxides; and, superoxide dismutase. In some embodiments, the reactive oxygen species can include peroxide ion, organic peroxides, organic hydroperoxides, peracid superoxides, dioxygenyls, ozones, and ozonides.

And, generally speaking, one of skill will appreciate that there are a wide variety of enzymes that can activate the binding system taught herein. And, the enzyme that bioactivates the binding system is, at least in part, responsible for the selectivity of the binding systems at a target site. Generally, the enzymes fall into the classes of oxidoreductases. As such, there are several enzymes and isozymes that will be present at a target site and capable of bioactivating the binding system. In some embodiments, the oxidoreductases can be categorized into about 22 classes, and the selectivity of the bioactivation of the binding system at a target site depends, at least in part, on the selectivity of the oxidoreductase at the target site. In some embodiments, the oxidoreductase can include those oxidoreductases that act on the CH—OH group of donors (alcohol oxidoreductases, for example; EC Number class 1.1). In some embodiments, the oxidoreductase can include those oxidoreductases that act on diphenols and related substances as donors (catechol oxidase, for example, EC Number class 1.10). In some embodiments, the oxidoreductase can include those oxidoreductases that act on peroxide as an acceptor (peroxidases, such as horseradish peroxidase and catalase; EC Number class 1.11). In some embodiments, the oxidoreductase can include those oxidoreductases that act on phenols as an acceptor (tyrosinases, for example; EC Number class 1.14). Examples of other useful enzymes for the teachings provided herein include, but are not limited to, glutathione peroxidase 1 and 4 (in many mammalian tissues), glutathione peroxidase 2 (in intestinal and extracellular mammalian tissues), glutathione peroxidase 3 (in plasma mammalian tissues), lactoperoxidase, myeloperoxidase (in salivary & mucosal mammalian tissues), myeloperoxidase (in neutrophil mammalian tissues), cytochrome peroxidase (in yeasts such as *Candida albicans*) and horseradish peroxidase (common to show in vitro activity). One of skill will appreciate that oxidoreductases are selective and, in some embodiments, the oxidoreductase can include an alternate enzyme that are selective for a binding system having a phenolic compound that acts as a substrate for the alternative enzyme.

In some embodiments, the oxidoreductases include monooxygenases such as, for example, phenylalaning monooxygenase, tyrosine monooxygenase, and tryptophan monooxygenase. In some embodiments, the oxidoreductases include dioxygenases such as, for example, tryptophan dioxygenase, homogentisate dioxygenase, trimethyl lysine dioxygenase, and nitric oxide synthase. In some embodiments, the oxidoreductases include peroxidases such as, for example, catalase, myeloperoxidase, thyroperoxidase. In some embodiments, the oxidoreductases act in the presence of a co-factor or co-enzyme, such as nicotinamide adenine dinucleotide phosphate (NADP) or nicotinamide adenine dinucleotide (NAD).

The compounds described herein can have one or more chemical substitutions. In some embodiments, the substitution can be at any location on the molecule or macromolecule and may be designated as an "R-group." The R groups can be used to represent nearly any chemical moiety, or functional group. For example, one of skill would or could substitute the group and still obtain the functions consistent with the teachings provided herein. For example, in some embodiments, an R group can be an alkyl, alkanyl, alkenyl, alkynyl, alkoxy, acyl, aryl, aralkyl, halo, heteroalkyl, heteroalkanyl, heteroalkenyl, heteroalkynyl, heteroaryl, heteroaralkyl, and the like.

"Alkyl," by itself or as part of another substituent, can refer to a saturated or unsaturated, branched, straight-chain or cyclic monovalent hydrocarbon radical derived by the removal of one hydrogen atom from a single carbon atom of a parent alkane, alkene or alkyne. Typical alkyl groups can include, but are not limited to, methyl; ethyls such as ethanyl, ethenyl, ethynyl; propyls such as propan-1-yl, propan-2-yl, cyclopropan-1 -yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1 -en-1 -yl, cyclobut-1-en-3-yl, cyclobuta-1,3-dien-1-yl, but-1-yn-1-yl, but-1-yn-3-yl, but-3-yn-1-yl, etc.; and the like. The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In some embodiments, an alkyl group comprises from 1 to 20 carbon atoms ($C_1$-$C_{20}$ alkyl). In some embodiments, an alkyl group comprises from 1 to 2, 1 to 3, 1 to 4, 1 to 5, 1 to 6, 1 to 7, 1 to 8, 1 to 9, or 1 to 10 carbon atoms ($C_1$-$C_{10}$ alkyl). In some embodiments, an alkyl group comprises from about 1 to 3 to about 1 to 6 carbon atoms (from $C_1$-$C_3$ $_{to}$ $C_1$-$C_6$ alkyl). In some embodiments, an alkyl group comprises from 1 to 4 carbon atoms ($C_1$-$C_4$ alkyl).

"Alkanyl," by itself or as part of another substituent, can refer to a saturated branched, straight-chain or cyclic alkyl radical derived by the removal of one hydrogen atom from a single carbon atom of a parent alkane. Typical alkanyl groups can include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl," by itself or as part of another substituent, can refer to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups can include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl , but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl," by itself or as part of another substituent can refer to an unsaturated branched, straight-chain or cyclic alkyl radical having at least one carbon-carbon triple bond derived by the removal of one hydrogen atom from a single carbon atom of a parent alkyne. Typical alkynyl groups can include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkoxy," by itself or as part of another substituent, can refer to a radical of the formula —O—$R^{400}$, where $R^{400}$ is alkyl or substituted alkyl as defined herein.

"Acyl" by itself or as part of another substituent can refer to a radical —C(O)$R^{401}$, where $R^{401}$ is hydrogen, alkyl, substituted alkyl, aryl, substituted aryl, arylalkyl, substituted arylalkyl, heteroalkyl, substituted heteroalkyl, heteroarylalkyl or substituted heteroarylalkyl as defined herein. Representative examples include, but are not limited to formyl, acetyl, cyclohexylcarbonyl, cyclohexylmethylcarbonyl, benzoyl, benzylcarbonyl and the like.

"Aryl," by itself or as part of another substituent, can refer to a monovalent aromatic hydrocarbon group derived by the removal of one hydrogen atom from a single carbon atom of a parent aromatic ring system, as defined herein. Typical aryl groups can include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms ($C_6$-$C_{20}$ aryl). In some embodiments, an aryl group comprises from 6 to 15 carbon atoms ($C_6$-$C_{15}$ aryl). In still other embodiments, an aryl group comprises from 6 to 15 carbon atoms ($C_6$-$C_{10}$ aryl). In some embodiments, an aryl group can be an arene moiety that forms at least a part of a molecule used in the teachings herein.

"Arylalkyl," by itself or as part of another substituent, can refer to an acyclic alkyl group in which one of the hydrogen atoms bonded to a carbon atom, typically a terminal or $sp^3$ carbon atom, is replaced with an aryl group as, as defined herein. Typical arylalkyl groups can include, but are not limited to, benzyl, 2-phenylethan-1-yl, 2-phenylethen-1 -yl, naphthylmethyl, 2-naphthylethan-1-yl, 2-naphthylethen-1- yl, naphthobenzyl, 2-naphthophenylethan-1-yl and the like. Where specific alkyl moieties are intended, the nomenclature arylalkanyl, arylalkenyl and/or arylalkynyl is used. In some embodiments, an arylalkyl group is ($C_6$-$C_{30}$) arylalkyl, e.g., the alkanyl, alkenyl or alkynyl moiety of the arylalkyl group is ($C_1$-$C_{10}$) alkyl and the aryl moiety is ($C_6$-$C_{20}$) aryl. In some embodiments, an arylalkyl group is ($C_6$-$C_{20}$) arylalkyl, e.g., the alkanyl, alkenyl or alkynyl moiety of the arylalkyl group is ($C_1$-$C_8$) alkyl and the aryl moiety is ($C_6$-$C_{12}$) aryl. In still other embodiments, an arylalkyl group is ($C_6$-$C_{15}$) arylalkyl, e.g., the alkanyl, alkenyl or alkynyl moiety of the arylalkyl group is ($C_1$-$C_5$) alkyl and the aryl moiety is ($C_6$-$C_{10}$) aryl.

"Compounds" can refer to compounds encompassed by structural formulae disclosed herein and includes any specific compounds within these formulae whose structure is disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that may be incorporated into the compounds of the invention include, but are not limited to, $^2H$, $^3H$, $^{13}C$, $^{14}C$, $^{15}N$, $^{18}O$, $^{17}O$, etc. Compounds may exist in unsolvated or unhydrated forms as well as solvated forms, including hydrated forms and as N-oxides. In general, compounds may be hydrated, solvated or N-oxides. Certain compounds may exist in multiple crystalline or amorphous forms. In general, all physical forms are equivalent for the uses contemplated herein and are intended to be within the scope of the present invention. Further, it should be understood, when partial structures of the compounds are illustrated, that brackets indicate the point of attachment of the partial structure to the rest of the molecule.

In some embodiments, the compounds can have one or more electron withdrawing group. An "electron withdrawing group" can refer to a chemical functional group that draws electrons away from a reaction center. Examples of electron withdrawing groups can include halogens (e.g., Cl,). nitriles (e.g., CN); carbonyls (e.g., CO), and nitro groups ($NO_2$). Any one or any combination of nitro, acyl, formyl, alkylsulfonyl, arylsulfonyl, trifluoromethyl, cyano, halo (e.g., fluoro, chloro, bromo, and iodo) moieties, and other electron-withdrawing groups can be used in some embodiments. In some embodiments, halo, nitrate and fluoromethyl groups ($CF_3$, $CHF_2$ or $CH_2F$) can be suitable electron withdrawing groups. One of skill will appreciate that there are several atoms, chemical groups, or structures, i.e., chemical moieties, that can function as an electron withdrawing group for purposes of the teachings provided herein. Whether a particular chemical moiety acts as an electron withdrawing group can depend on the nature of the neighboring chemical moiety or moieties, as an electron withdrawing group draws electron density from neighboring atoms towards itself, usually by resonance or inductive effects. In some embodiments, a weaker base can draw electrons from stronger base. For purposes of illustration, trifluoroacetate ion is a weaker base than acetate ion because the trifluoromethyl group is able to draw electron density away from the carboxylate when in a neighboring chemical relationship, making the trifluoromethyl group an electron withdrawing group in this situation. One of skill will appreciate that electron withdrawing groups can be added in one or more positions of a chemical structure to produce a cumulative effect, and each electron withdrawing group can be independently selected.

"Halogen", or "halo," by itself or as part of another substituent can refer to a radical —F, —Cl, —Br or —I.

"Heteroalkyl," "Heteroalkanyl," "Heteroalkenyl" and "Heteroalkynyl," by themselves or as part of other substituents, refer to alkyl, alkanyl, alkenyl and alkynyl groups, respectively, in which one or more of the carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, —O—, —S—, —N—, —Si—, —NH—, —S(O)—, —S(O)$_2$—, —S(O)NH—, —S(O)$_2$NH— and the like and combinations thereof. The heteroatoms or heteroatomic groups may be placed at any interior position of the alkyl, alkenyl or alkynyl groups. Typical heteroatomic groups which can be included in these groups can include, but are not limited to, —O—, —S—, —O—O—, —S—S—, —O—S—, —NR$^{501}$R$^{502}$, =N—N=, —N=N—, —N=N—NR$^{503}$R$^{404}$, —PR$^{505}$—, —P(O)$_2$—, —POR$^{506}$—, —O—P(O)$_2$—, —SO—, —SO$_2$—, —SnR$^{507}$R$^{508}$— and the like, where R$^{501}$, R$^{502}$, R$^{503}$, R$^{504}$, R$^{505}$, R$^{506}$, R$^{507}$ and R$^{508}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl," by itself or as part of another substituent, can refer to a monovalent heteroaromatic radical derived by the removal of one hydrogen atom from a single atom of a parent heteroaromatic ring systems, as defined herein. Typical heteroaryl groups can include, but are not limited to, groups derived from acridine, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group comprises from 5 to 20 ring atoms (5-20 membered heteroaryl). In some embodiments, the heteroaryl group comprises from 5 to 10 ring atoms (5-10 membered heteroaryl). Exemplary heteroaryl groups can include those derived from furan, thiophene, pyrrole, benzothiophene, benzofuran, benzimidazole, indole, pyridine, pyrazole, quinoline, imidazole, oxazole, isoxazole and pyrazine.

"Heteroarylalkyl" by itself or as part of another substituent can refer to an acyclic alkyl group in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylakenyl and/or heteroarylalkynyl is used. In some embodiments, the heteroarylalkyl group is a 6-21 membered heteroarylalkyl, e.g., the alkanyl, alkenyl or alkynyl moiety of the heteroarylalkyl is ($C_1$-$C_6$) alkyl and the heteroaryl moiety is a 5-15-membered heteroaryl. In some embodiments, the heteroarylalkyl is a 6-13 membered heteroarylalkyl, e.g., the alkanyl, alkenyl or alkynyl moiety is ($C_1$-$C_3$) alkyl and the heteroaryl moiety is a 5-10 membered heteroaryl.

"Parent Aromatic Ring System" can refer to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System" can refer to a parent aromatic ring system in which one or more carbon atoms (and optionally any associated hydrogen atoms) are each independently replaced with the same or different heteroatom. Typical heteroatoms to replace the carbon atoms include, but are not limited to, N, P, O, S, Si, etc. Specifically included within the definition of "parent heteroaromatic ring system" are fused ring systems in which one or more of the rings are aromatic and one or more of the rings are saturated or unsaturated, such as, for example, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Salt" can refer to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Substituted," when used to modify a specified group or radical, means that one or more hydrogen atoms of the specified group or radical are each, independently of one another, replaced with the same or different substituent(s). Substituent groups useful for substituting saturated carbon atoms in the specified group or radical include, but are not limited to —$R^a$, halo, —$O^-$, =O, —$OR^b$, —$SR^b$, —$S^{31}$, =S, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2NR^b$, —$S(O)_2OR^b$, —$OS(O)_2R^b$, —$OS(O)_2O^b$, —$OS(O)_2OR^b$, —$P(O)(O)_2$, —$P(O)(OR^b)(O)$, —$P(O)(OR^b)(OR^b)$, —$C(O)R^b$, —$C(S)R^b$, —$C(NR^b)R^b$, —$C(O)O^-$, $C(O)OR^b$, —$C(S)OR^b$, —$C(O)NR^cR^c$, —$C(NR^b)NR^cR^c$, —OC(O)$R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)O^-$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, cycloalkyl, heteroalkyl, cycloheteroalkyl, aryl, arylalkyl, heteroaryl and heteroarylalkyl; each $R^b$ is independently hydrogen or $R^a$; and each $R^c$ is independently $R^b$ or alternatively, the two $R^c$s are taken together with the nitrogen atom to which they are bonded form a 4-, 5-, 6- or 7-membered cycloheteroalkyl which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl.

Similarly, substituent groups useful for substituting unsaturated carbon atoms in the specified group or radical include, but are not limited to, —$R^a$, halo, —$O^-$, -$OR^b$, —$SR^b$, —$S^-$, —$NR^cR^c$, trihalomethyl, —$CF_3$, —CN, —OCN, —SCN, —NO, —$NO_2$, —$N_3$, —$S(O)_2R^b$, —$S(O)_2O^-$, —$S(O)_2OR^b$, —$OS(O)_2R^b$, —$OS(O)_2O^{31}$, —$OS(O)_2OR^b$, —$P(O)(O)_2$, —$P(O)(OR^b)(O^-)$, —$P(O)(OR^b)(OR^b)$, —$C(O)R^b$, —$C(S)R^b$, —$C(NR^b)R^b$, —$C(O)O^{31}$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups useful for substituting nitrogen atoms in heteroalkyl and cycloheteroalkyl groups can include, but are not limited to, —$R^a$, —$O^-$, —$OR^b$, —$SR^b$, —$S^{31}$, —$NR^cR^c$, trihalomethyl, —$CF_3$, —CN, —NO, —$NO_2$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O)_2$, —$P(O)(OR^b)(O^-)$, —$P(O)(OR^b)(OR^b)$, —$C(O)R^b$, —$C(S)R^b$, —$C(NR^b)R^b$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)OR^b$, —$OC(S)OR^b$, —$NR^bC(O)R^b$, —$NR^bC(S)R^b$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups from the above lists useful for substituting other specified groups or atoms will be apparent to those of skill in the art. The substituents used to substitute a specified group can be further substituted, typically with one or more of the same or different groups selected from the various groups specified above.

Methods of Making the Binding Systems

The design of the binding systems include (i) selecting the phenolic compound, (ii) selecting the reactive oxygen species, (iii) selecting the ratio of phenolic compound to reactive oxygen species, and (iv) selecting a carrier. In some embodiments, the phenolic compound can be derivatized or attached to another chemical moiety via a linker, or another known method such as, for example, esterification to facilitate or improve an association between the phenolic compound and the reactive oxygen species, as well as to potentially modify, solubility, tissue absorption, or toxicity.

One of skill will appreciate that, at least from the teachings provided herein, there are a vast number of binding systems that can be selected for bioactivation at a given target site, the selection of which is, at least in part, dependent on type of enzyme, co-enzymes, cofactors or catalysts present at the target site for the bioactivation of the binding system. The design of the binding system can include for example, (i) identifying the target site; (ii) identifying an enzyme, co-enzymes, cofactors, or catalysts present at the target site but not present at tissue surrounding the target site; (iii) selecting a binding pair for activation at the target site by the enzyme, co-enzymes, cofactors, or catalysts; and, (iv) selecting a carrier in which the binding pair is stable or substantially stable.

Identifying the target site includes, for example, select a target tissue for treatment, such as a damaged tissue at which the enzyme, co-enzymes, cofactors or catalysts present. In some embodiments, the target site is a damaged mucosal tissue, such as a damaged GI tissue, at which peroxidase or oxidase may be present.

Identifying an enzyme, co-enzymes, cofactors, or catalysts present at the target site but not present at tissue surrounding the target site can include identifying the tissue type, and the type of damage, as well as the presence of a microbe, for example. Anaerobic pathogens such as *Pseudomonas* and *Vibrio* can express a peroxide or an oxidase, making these enzymes available at the target site.

Given the teachings provided herein, one of skill can select a binding pair for activation at the target site by the enzyme, co-enzymes, cofactors, or catalysts. After the binding pair and environment of use are known, one of skill can a carrier in which the binding pair is stable or substantially stable. In one example, the binding system can comprise a mixture of phenolic compounds in a desired ratio with hydrogen peroxide. The phenolic compounds include a mixture of a pomegranate extract and a green tea extract, and the ratio of phenolic compound to hydrogen peroxide can range from about 1:2 to about 1:20 on a wt/wt basis (molar weight). The hydrogen peroxide can be added to the phenolic compound using a concentration of about 0.1% to about 10% hydrogen peroxide solution. One of skill can easily selected the dose for a particular use, which will vary according to use, due to environmental conditions at the site of use. In another example, the binding system can comprise a mixture of phenolic compounds in a desired ratio with hydrogen peroxide. The phenolic compounds include a mixture of a pomegranate extract and a green tea extract, and the ratio of phenolic compound to hydrogen peroxide can range from about 3:1 to about 1:3 on a wt/wt basis (molar weight). The hydrogen peroxide can be added to the phenolic compound using a concentration of about 0.1% to about 10% hydrogen peroxide solution. One of skill can easily selected the dose for a particular use, which will vary according to use, due to environmental conditions at the site of use. In some embodiments, this formulation has worked well for uses in animals that are non-humans.

As such, the binding system will selectively target damaged tissues and pathogens infecting those tissues, whereas the same microbes passively occupying healthly surrounding tissues and healthy surround tissues themselves will not activate the binding system. The same type of localized and selective response can be expected, for example, for inflammations and infections as with toxins.

The binding system can be carried in a liquid, powder, capsule, tablet, or gas for administration to a subject. The selection of the phenolic compound should take into consideration the manner in which the reactive oxygen species will bind to the phenolic compound to form a stable, or substantially stable, binding pair. The binding pair can be considered substantially stable where the reactive oxygen species retains all, most, or at least a predictable amount of oxidation strength for the uses and functions recited herein.

One of skill will appreciate that a phenolic compound can be derivatized to introduce or enhance a desired function. The phenolic compound can be derivatized, for example, to increase it's functionality for binding to the reactive oxygen species, maintaining stability or miscibility in a carrier, or binding to a target site, using any method known to one of skill. In some embodiments, the phenolic compound can be bound to a polyol, pegylated, attached to a saccharide, or attached to glucose, for example.

One of skill will appreciate that a phenolic compound can be linked to another chemical entity by a linker in order to introduce or enhance a desired function. In some embodiments, a linker can include, for example, from 1 to 4 amino acids, natural or synthetic. In some embodiments, a synthetic linker can include an aminoalkanoic acid having from about 1 to about 20 carbons, from about 2 to about 14 carbons from about 3 to about 12 carbons, from about 4 to about 11 carbons, from about 5 to about 10 carbons, or any range therein. Examples can include, but are not limited to 4-aminobutanoic acid, 5-aminopentanoic acid, 6-aminohexanoic acid, 7-aminoheptanoic acid, 8-amino-octanoic acid, 9-aminononanoic acid 10-aminodecanoic acid, 11-aminoundecanoic, and the like. One of skill will appreciate that these linkers can be substituted, as long as the linker functions in accordance with the teachings provided herein. In some embodiments, the binding system can be cross linked onto a microbead, magnetic particle, nano-particle or other substrate to form a reaction enhanced, tissue specific or steerable ligand or therapeutic system.

The binding systems can include, for example, a weight ratio of phenolic compound to reactive oxygen species that ranges from about 1:1000 to about 1000:1. In some embodiments, the ratio of phenolic compound to reactive oxygen species can range from about 1:1000 to about 500:1, from about 1:500 to about 500:1, from about 1:250 to about 500:1, from about 1:500 to about 250:1, from about 1:250 to about 250:1, from about 1:100 to about 250:1, from about 1:250 to about 100:1, from about 1:100 to about 100:1, from about 1:100 to about 50:1, from about 1:50 to about 100:1, from about 1:50 to about 50:1, from about 1:25 to about 50:1, from about 1:50 to about 25:1, from about 1:25 to about 25:1, from about 1:10 to about 10:1, from about 1:1000 to about 250:1, from about 1:1000 to about 100:1, from about 1:1000 to about 50:1, from about 1:1000 to about 25:1, from about 1:1000 to about 10:1, from about 1:1000 to about 5:1, from about 1:10 to about 1:20, from about 1:10 to about 1:30, from about 1:10 to about 1:40, from about 1:10 to about 1:50, from about 1:10 to about 1:60, from about 1:10 to about 1:70, from about 1:10 to about 1:80, from about 1:10 to about 1:90, from about 1:20 to about 1:30, from about 1:20 to about 1:40, from about 1:20 to about 1:50, from about 1:20 to about 1:60, from about 1:20 to about 1:70, from about 1:20 to about 1:80, from about 1:20 to about 1:90, from about 1:30 to about 1:90, or any range therein.

In some embodiments, the binding system comprises a ratio of a tannin and hydrogen peroxide, a phenylpropanoid and a hydrogen peroxide, a catechin and hydrogen peroxide, an epigallic acid and a hydrogen peroxide, or a combination thereof an of these phenolic compounds with hydrogen peroxide.

In some embodiments, the binding systems include a stable hydrogen bonded complex between the phenolic compound and the reactive oxygen species. For example, a highly hydroxylated polyphenol compound can be combined with a high concentration of hydrogen peroxide, the combination leading to binding the hydrogen peroxide to the phenolic compound to produce the binding system. The binding system can be intended for dilution in water or a solid excipient. One of skill will appreciate that such a complex can be referred to as a polyphenol peroxysolvate, in some embodiments, when in a liquid form for storage or administration to a subject, and a phenolic perhydrate when in an anhydrous, or substantially anhydrous, form for storage or administration to a subject.

One of skill will appreciate that the binding systems should be produced free of compounds that can lead to degradation of the otherwise stable, or substantially stable, binding pairs. As such, in some embodiments, the compositions comprise solutes that are substantially free of transition metals, metal ions, heavy metals, oxidoreductase enzymes, other strong oxidizers, reactive halogen compounds, hydrogen halides, and other compounds that can cause a decomposition of the reactive oxygen species, or its disassociation from the phenolic compound with which it forms a binding pair.

Methods of Using the Binding Systems

The compositions taught herein can be used for medicinal purposes, as a health supplement, or a nutritional composition. The compositions can provide a therapeutic and/or prophylactic effect in the treatment of a condition in a subject. The targeted action of the binding systems allows for the administration of surprisingly low effective doses of the phenolic compounds. As a result, the binding systems also improve safety by substantially increasing the separation between an effective dose and any toxic/side effects.

The terms "treat," "treating," and "treatment" can be used interchangeably and refer to the administering or application of the binding systems taught herein, including such administration as a health or nutritional supplement, and all administrations directed to the prevention, inhibition, amelioration of the symptoms, or cure of a condition taught herein. The terms "disease," "condition," "disorder," and "ailment" can be used interchangeably in some embodiments. The term "subject" and "patient" can be used interchangeably and refer to an animal such as a mammal including, but not limited to, non-primates such as, for example, a cow, pig, horse, cat, dog, rat and mouse; and primates such as, for example, a monkey or a human. As such, the terms "subject" and "patient" can also be applied to non-human biologic applications including, but not limited to, veterinary, companion animals, commercial livestock, aquaculture, and the like. Many of the applications can include control environmental pathogens that are on or in plants, as well as places not necessarily in living hosts, such as those that are in water and water systems, for example, as well as soil, air, and food for microbial control, alteration of surface characteristics, or anywhere that can benefit from a supply of a stable oxidizer source.

In some embodiments, the binding system includes (i) a phenolic compound selected from the group consisting of condensed tannins, hydrolysable tannins, complex tannins, phlorotannins, psuedotannins, and derivatives thereof; and, (ii) hydrogen peroxide in a stable, or substantially stable, non-covalent association. When the binding system is combined with an oxidoreductase enzyme at a target site, the combination promotes increased binding, complexing, metabolizing or crosslinking of the phenolic compound with the tissues, pathogens and toxins in or on a subject. The binding systems can be administered to increase the bioactivity of the phenolic compound in a binding reaction. It should be noted that the bioactivity at a GI, dermal, or mucosal target site can be detrimentally affected by a reduced bioavailability, such as by absorption rates of the phenolic compound into the systemic circulation. And, the adverse effects of such absorption on a subject, the phenolic compounds that create them, and the amounts at which they occur, remain unkown. It is known, however, that gallic acid and isoflavones, for example, can be considered as the most well-absorbed phenols, followed by catechins (flavan-3-ols), flavanones, and quercetin glucosides, each having different kinetics. In contrast, the least well-absorbed phenols are the proanthocyanidins, galloylated tea catechins, and anthocyanins.

Generally speaking, the binding systems provided herein selectively bind to, and reduce, the infectivity or propogation of virus, bacteria, yeast or fungi; and, upon enzymatic bioactivation by pathogens or damaged tissues, exhibit increased binding inactivation of endotoxins, such as lipopolysaccharides, and exotoxins, such as cholera toxin, botulism, and other virulence factors of bacteria that are pathogenic to a subject, human or non-human. Likewise, the binding systems exhibit a localized astringent effect upon a damaged tissue of a subject. Without intending to be bound by any theory or mechanism of action, this is believed to be due to the tissue presenting higher levels of oxidoreductase enzymes than comparable undamaged tissues, making the action of the binding system serve as a localized and targeted action that is selective to the damaged tissue. Moreover, the binding systems function to treat a tissue suffering from inflammation by reducing the inflammation in, also in a targeted manner upon bioactivation of the binding system at the target site. The systems can be used, for example, to treat a GI condition, a dermal condition, or a mucosal condition. And, it should be appreciated that, in some embodiments, the binding systems can be used as a health or nutritional supplement as a prophylactic method of treatment to prevent the onset of a condition; a treatment. management, or cure of a condition that has already onset; or a way to ameliorate the symptoms of such a condition that has already onset.

In some embodiments, the binding systems taught herein can be used to protect, maintain, improve, or restore a digestive health of a subject when administered orally in an effective amount, the effectiveness measured by comparing to a control group that did not receive the binding system. The binding systems can be used to prevent, inhibit, or ameliorate the symptoms associated with a loss of digestive tract homeostasis. In some embodiments, the binding systems can be used to prevent, treat, ameliorate the symptoms of, or even cure, a chronic gastrointestinal condition. Such conditions can include, but are not limited to, hyperacidity, colitis, irritable bowel syndrome, crohn's disease, necrotic enteritis, functional colonic diseases, malabsorption, a peptic ulcer, gastroesophageal reflux disease, ulcerative colitis, and diverticulitis. In some embodiments, the binding systems can be used to reduce mucosal tissue inflammation, dysfunction, or damage. Such conditions can be induced, for example, by drug side effects, chemotherapy, dysbiosis, radiation, changes in normal flora, hyperimmunity, autoimmune reactions, immune deficiencies, nervousness, allergies, chemical irritation, and stress. In some embodiments, the binding systems can be administered for selectively inhibiting the growth of gastrointestinal pathogens. It should be appreciated that there may be lesser inhibition of non-pathogenic strains, particularly common probiotic bacteria such as bifidobacteria and lactobacilli. And, in some embodiments, administration of the binding systems can produce short term immune modulation effects as well as potentially change the chronic expression of the activating enzymes associated with some conditions with longer term use of the binding systems.

In some embodiments, the symptoms of a gastrointestinal condition can include, for example, diarrhea, dehydration, malnutrition, constipation, nausea, and/or cramping. And, in some embodiments, the symptoms of a gastrointestinal condition can be temporary and include acid irritation, indigestion, bloating, cramps, spasmodic peristalsis, diarrhea, and constipation. Administering the binding systems for the treatment and/or management of gastrointestinal conditions can be considered a nutritional or health supplement, in some embodiments. In some such embodiments, for example, the binding pair can be administered to prevent, inhibit, or ameliorate the effect, infectivity, and virulence of pathogens including bacteria, virus, fungi, yeast, prions, protazoa and parasites in a subject orally taking an effective amount of the supplement.

As such, in some embodiments, the teachings are directed to a system to facilitate an improved bioactivity and increased enzyme activation rates upon contact of the binding system with damaged cells, white blood cells or bacterial infection, while remaining passive to tissues that do not present such enzymes and non-pathogenic microbiota. In these embodiments, the bioactivation can be mediated by oxidoreductase enzymes, for example, which modify phenolic compounds in-situ. The reaction rate can be limited, for example, by availability of hydrogen peroxide or one of its degradation products. In some embodiments, the oxidoreductase enzymes may be native to damaged animal cells or pathogenic bacteria. The system can, therefore, provide a localized increase in ability of the phenolic compounds taught herein to form covalent complexes with a target. The target can include, for example, amino acids, alcohols, peptides, oligopeptides, proteins, saccharides, polyols, and the like, as well as other macromolecules involved with bacterial infection, inflammatory response, tissue damage, tissue healing.

The binding systems are also useful in treating wounds. Generally speaking, the binding systems can protect, seal, disinfect, promote healing, or improve function of skin or mucosa. In some embodiments, for example, a wound and a chronic inflammatory condition can be treated including, but not limit to, a wound by (i) physical damage, (ii) adiabetic skin lesion, (iii) abed sore, (iv) a burn, (v) a cold sore, (vi) psoriasis, (vii) eczema, and (viii) dermatological inflammation caused by pathogens, to name a few.

The binding systems are also useful in treating inflammations. In some embodiments, the binding systems are useful in treating inflammations of gastrointestinal system, urinary tract, reproductive system, or respiratory system inflammations in a subject, in which the binding systems can be administered, for example, in the form of an enema, nasal spray, or respiratory mist to prevent, treat, inhibit, or ameliorate the symptoms of an inflammation of a mucosal tissue.

The binding systems are also useful in treating infections. In some embodiments, the binding systems can be used to treat infections of gastrointestinal system, urinary tract, reproductive system, or respiratory system infections in a subject, in which the binding systems can be administered, for example, in the form of an enema, nasal spray, or respiratory mist to prevent, treat, inhibit, or ameliorate the symptoms of an infection of a mucosal tissue. In some embodiments, the binding systems find a particularly useful application in women, children, and pets.

In some embodiments, the binding system is in a liquid form as a general health tonic. Liquid systems can include, but are not limited to, any liquid formulation known to one of skill. In some embodiments, the liquid formulation can include a solution, a colloid, a suspension, an emulsion, a liposomal formulation, and the like. In some embodiments, the binding system is in a liquid form for treatment of a short term acute digestive condition. Examples of such conditions include, but are not limited to, diarrhea, food poisoning, and traveler's diarrhea. And in some embodiments, the binding system is in a liquid form for treatment of a chronic digestive condition. Examples of such conditions include, but are not limited to, gastroesophageal reflux disease, inflammatory bowel disease, irritable bowel syndrome, and food allergies.

In some embodiments, the binding system is a dry system. For example, the system can be in the form of a powder, pill, tablet, capsule, or a separate dry components for mixing into a liquid form. In these embodiments, both the phenolic compound and the reactive oxygen species are in a dry form either before or after creation of the binding pair, and the binding system can be used in the dry form, or converted to a liquid form, for any of the uses taught herein. The advantages of the dry compositions can include, for example, the ease of storage and transport. In some embodiments, the binding systems, whether in liquid or dry form, can be combined with vitamins, electrolytes, and/or other nutrients in either liquid or dry form. The dry form of the binding system can be manufactured using any drying process known to one of skill, such as solvent exchange, vacuum drying, critical point drying, heating, dessication, or a combination thereof. In some embodiments, the phenolic compound is dried as a single component. In some embodiments, the binding pair is formed, and the binding pair is dried together. And, in some embodiments, the reactive oxygen species can be, independently, in any dry form known to one of skill, such as the dry forms taught herein. In embodiments having the reactive oxygen species in an independent dry form, the dry phenolic compound and the dry reactive oxygen species can be combined in a polar solvent, for example, to create the binding pair prior to use.

The binding systems can be in the form of a kit. In some embodiments, the kit can comprise a binding system taught herein, wherein the kit comprises a dry form of the phenolic compound component and a dry form of the reactive oxygen species component, as well as instructions for mixing the components to create the binding system for administration and suggested dilution factors for various target sites. In some embodiments, the kit can comprise a dry form of the binding system, as well as instructions for diluting the binding system for administration with suggested dilution factors for various target sites. The suggested dilution factors can be selected from the ranges taught herein.

As described herein, the binding systems can be used in a method of treating a damaged dermal, mucosal, or gastrointestinal tissue. In some embodiments, the method can comprise administering an effective amount of a binding systema taught herein to the damaged tissue of the subject. The binding system can function as an antimicrobial when bioactivated at the target site of the damaged tissue and assist in the healing of the damaged tissue by inactivating compounds that promote infection at the target site.

As described herein, the binding systems can be used in a method of treating a gastrointestinal condition. In some embodiments, the method can comprise administering an effective amount of a binding system taught herein to the gastrointestinal tract of the subject. The binding system can function as an astringent, an anti-toxin, an anti-inflammatory, or an antimicrobial, for example, when bioactivated at the target site of the damaged tissue and assists in the healing of the damaged tissue by inactivating compounds that promote the condition at the target site.

As described herein, the binding systems can be used in a method of treating acute diarrhea in a subject. In some embodiments, the methods comprise orally administering an effective amount of a binding system taught herein to the subject. The binding system can prevent, inhibit, or ameliorate a symptom of acute diarrhea in the subject when compared to a second subject in a control group in which the binding system was not administered. In some embodiments, the symptom is selected from the group consisting of a stool score, heartburn, indigestion, urgency of defecation, nausea, vomiting, stomach pain, and bloating.

As described herein, the binding systems can be used in a method of promoting weight gain in a subject. In some embodiments, the method comprises orally administering an effective amount of a binding system taught herein to the subject as a supplement to the diet of the subject. The binding systems can increase the feed conversion ratio of the subject when compared to a second subject in a control group in which the binding system was not administered.

As described herein, the binding systems can be used in a method of treating irritable bowel syndrome in a subject. In some embodiments, the method comprises orally administering an effective amount of a binding system taught herein to the subject. The binding system can prevent, inhibit, or ameliorate the symptoms of irritable bowel syndrome in the subject when compared to a second subject in a control group in which the binding system was not administered. In some embodiments, the symptom is selected from the group consisting of a stool score, heartburn, indigestion, urgency of defecation, nausea, vomiting, stomach pain, and bloating.

As described herein, the binding systems can be used in a method of treating an inflammatory bowel disease in a subject. In some embodiments, the method comprises orally administering an effective amount of a binding system taught herein to the subject. The binding system can prevent, inhibit, or ameliorate the symptoms of inflammatory bowel disease in the subject when compared to a second subject in a control group in which the binding system was not administered. In some embodiments, the symptom is selected from the group consisting of a stool score, heartburn, indigestion, urgency of defecation, nausea, vomiting, stomach pain, and bloating.

As described herein, the binding systems can be used in a method of treating food poisoning in a subject. In some embodiments, the method comprises orally administering an effective amount of a binding system taught herein to the subject. The binding system can prevent, inhibit, or ameliorate the symptoms of food poisoning in the subject when compared to a second subject in a control group in which the binding system was not administered. In some embodiments, the symptom is selected from the group consisting of a stool score, heartburn, indigestion, urgency of defecation, nausea, vomiting, stomach pain, and bloating.

As described herein, the binding systems can be used in a method of treating a wound on a tissue of a subject. In some embodiments, the method comprises administering an effective amount of a binding system taught herein to a wound of the subject. The binding system can enhance the rate of healing in the subject when compared to a second subject in a control group in which the binding system was not administered. In some embodiments, the wound is to a dermal tissue, mucosal tissue, or gastrointestinal tissue.

As described herein, the binding systems can be used in a method of improving the gastrointestinal health of in a subject. In some embodiments, the method comprises orally administering a binding system taught herein, wherein, the binding system improves the gastrointestinal health in the subject when compared to a second subject in a control group in which the binding system was not administered.

Methods of Administration

In some embodiments, the binding systems can be administered to a subject in any non-parenteral manner known to one of skill, where a parenteral administration involves piercing the skin or a mucous membrane. In these embodiments, the administration can be oral, ocular, otologic, nasal, urogenital, rectal, dermal, or to a mucous membrane. In some embodiments, the administration can be oral or topical, using any manner of administration known to one of skill. Oral administration can include digestive tract, buccal, sublingual, sublabial, and respiratory tract administration, and a carrier such as a solid or liquid can be used. One of skill will appreciate that the therapeutic program selected, the agents administered, the condition of the subject, and the effects desired, can affect the administration schedule and program used.

In many embodiments, the binding systems can be administered orally in diluted in aqueous solutions, or incorporated with excipients. The binding systems can be contained in forms that include tablets, troches, capsules, elixirs, beverages, suspensions, syrups, wafers, chewing gums, gels, hydrogels, and the like. Tablets, pills, capsules, troches liquids and the like may also contain binders, excipients, disintegrating agent, lubricants, glidants, chelating agents, buffers, tonicity modifiers, surfactants, sweetening agents, and flavoring agents. Some examples of binders include microcrystalline cellulose, gum tragacanth or gelatin. Some examples of excipients include starch or maltodextrin. Some examples of disintegrating agents include alginic acid, corn starch and the like. Some examples of lubricants include magnesium stearate or potassium stearate. An example of a chelating agent is EDTA. Some examples of buffers are acetates, citrates or phosphates. Some examples of tonicity modifiers include sodium chloride and dextrose. Some examples of surfactants for micellation or increasing cell permeation include coconut soap, anionic, cationic or ethoxylate detergents. An example of a glidant is colloidal silicon dioxide. Some examples of sweetening agents include sucrose, saccharin and the like. Some examples of flavoring agents include peppermint, chamomile, orange flavoring and the like. It should be appreciated that the materials used in preparing these various compositions should be pharmaceutically pure and non-toxic in the amounts used.

In the digestive tract, a solid can include a pill, capsule, tablet, or time-release technology in some embodiments; and, a liquid can include a solution, soft gel, suspension, emulsion, syrup, elixir, tincture, or a hydrogel. Digestive tract administration can include oral or rectal administration using any method known to one of skill. For buccal, sublingual, and sublabial administration, a solid can include an orally disintegrating tablet, a film, a lollipop, a lozenge, or chewing gum; and, a liquid can include a mouthwash, a toothpaste, an ointment, or an oral spray.

For respiratory tract administration, which also includes any tissue or cavity in communication with the respiratory track, such as the sinuses, a solid can be administered using a smoking device; and, a liquid can be administered using a pressurized metered dose inhaler, a nebulizer, or a vaporizer. In some embodiments, nasal administration can be used and includes administering the binding system to the mucus membranes of the nasal passage or nasal cavity of a subject. Any method of nasal administration known to one of skill to be suitable for the compositions provided herein can be used. In some embodiments, the nasal administration can include nasal spray, nasal drop, suspension, gel, ointment, cream or powder. In some embodiments, a nasal tampon or nasal sponge can be used.

For ocular, otologic, and nasal administrations, the compounds can be administered using a nasal spray, ear drops, eye drops, an ointment, a hydrogel, nanosphere suspension, or a mucoadhesive microdisc. For urogenital administrations, the compounds can be administered using an ointment, a pessary such as a vaginal suppository, or a vaginal douche. For rectal administrations, which also includes administration into the large intestine in some embodiments, the compounds can be administered using an ointment, a suppository, an enema, a Murphy drip, a nutrient enema, or using an endoscopic device. For Dermal administrations, the compounds can be administered using an ointment, a liniment, a paste, a film, a hydrogel, liposomes, transfersome vesicals, cream, lotion, lip balm, medicated shampoo, a dermal patch, or a dermal spray.

One of skill understands that the amount of the agents administered can vary according to factors such as, for example, the type of disease, age, sex, and weight of the subject, as well as the method of administration. For example, an administration can call for substantially different amounts to be effective. Dosage regimens may also be adjusted to optimize a therapeutic response. In some embodiments, a single bolus may be administered; several divided doses may be administered over time; the dose may be proportionally reduced or increased; or, any combination thereof, as indicated by the exigencies of the therapeutic situation and factors known one of skill in the art. It is to be noted that dosage values may vary with the severity of the condition to be alleviated, as well as whether the administration is prophylactic, such that the condition has not actually onset or produced symptoms. Dosage regimens may be adjusted over time according to the individual need and the professional judgment of the person administering or supervising the administration of the compositions, and the dosage ranges set forth herein are exemplary only and do not limit the dosage ranges that may be selected by medical practitioners.

The terms "administration" or "administering" can be used to refer to a method of incorporating a composition into the cells or tissues of a subject, either in vivo or ex vivo to test the activity of a system, as well as to diagnose, prevent, treat, or ameliorate a symptom of a disease. In one example, a compound can be administered to a subject in vivo using any means of administration taught herein. In another example, a compound can be administered ex vivo by combining the compound with cell tissue from the subject for purposes that include, but are not limited to, assays for determining utility and efficacy of a composition. And, of course, the binding systems can be used in vitro to test their stability, activity, toxicity, efficacy, and the like. When the compound is incorporated in the subject in combination with one or active agents, the terms "administration" or "administering" can include sequential or concurrent incorporation of the compound with the other agents such as, for example, any agent described above. A pharmaceutical composition of the invention can be formulated, in some embodiments, to be compatible with its intended route of administration.

An "effective amount" of a compound can be used to describe a therapeutically effective amount or a prophylactically effective amount. An effective amount can also be an amount that ameliorates the symptoms of a disease. A "therapeutically effective amount" can refer to an amount that is effective at the dosages and periods of time necessary to achieve a desired therapeutic result and may also refer to an amount of active compound, prodrug or pharmaceutical agent that elicits any biological or medicinal response in a tissue, system, or subject that is sought by a researcher, veterinarian, medical doctor or other clinician that may be part of a treatment plan leading to a desired effect. In some embodiments, the therapeutically effective amount should be administered in an amount sufficient to result in amelioration of one or more symptoms of a disorder, prevention of the advancement of a disorder, or regression of a disorder. In some embodiments, for example, a therapeutically effective amount can refer to the amount of an agent that provides a measurable response of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of a desired action of the composition.

A "prophylactically effective amount" can refer to an amount that is effective at the dosages and periods of time necessary to achieve a desired prophylactic result, such as prevent the onset of an inflammation, allergy, nausea, diarrhea, infection, and the like. Typically, a prophylactic dose is used in a subject prior to the onset of a disease, or at an early stage of the onset of a disease, to prevent or inhibit onset of the disease or symptoms of the disease. A prophylactically effective amount may be less than, greater than, or equal to a therapeutically effective amount.

Any administration vehicle known to one of skill to be suitable for administration of the compounds, compositions, and formulations taught herein can be used. A "vehicle" can refer to, for example, a diluent, excipient or carrier with which a compound is administered to a subject.

The compounds can be administered in dosage units. The term "dosage unit" can refer to discrete, predetermined quantities of a compound that can be administered as unitary dosages to a subject. A predetermined quantity of active compound can be selected to produce a desired therapeutic effect and can be administered with a pharmaceutically acceptable carrier. The predetermined quantity in each unit dosage can depend on factors that include, but are not limited to, (a) the unique characteristics of the active compound and the particular therapeutic effect to be achieved, and (b) the limitations inherent in the art of creating and administering such dosage units.

A "pharmaceutically acceptable carrier" is a diluent, adjuvant, excipient, or vehicle with which the composition is administered. A carrier is pharmaceutically acceptable after approval by a state or federal regulatory agency or listing in the U.S. Pharmacopeial Convention or other generally recognized sources for use in subjects.

The pharmaceutical carriers include any and all physiologically compatible solvents, dispersion media, coatings, antibacterial and antifungal agents, isotonic and absorption delaying agents, and the like. Examples of pharmaceutical carriers include, but are not limited to, sterile liquids, such as water, oils and lipids such as, for example, phospholipids and glycolipids. These sterile liquids include, but are not limited to, those derived from petroleum, animal, vegetable or synthetic origin such as, for example, peanut oil, soybean oil, mineral oil, sesame oil, and the like.

Suitable pharmaceutical excipients include, but are not limited to, starch, sugars, inert polymers, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition can also contain minor amounts of wetting agents, emulsifying agents, pH buffering agents, or a combination thereof. The compositions can take the form of solutions, suspensions, emulsion, tablets, pills, capsules, powders, sustained-release formulations and the like. Oral formulations can include standard carriers such as, for example, pharmaceutical grades mannitol, lactose, starch, magnesium stearate, sodium saccharine, cellulose, magnesium carbonate, and the like. See Martin, E. W. Remington's Pharmaceutical Sciences. Supplementary active compounds can also be incorporated into the compositions.

In some embodiments, an administration, such as an oral or topical administration, may include liposomes. In some embodiments, the liposome may assist in a targeted delivery system. The liposomes can be designed, for example, to bind to a target protein and be taken up selectively by the cell expressing the target protein.

Therapeutic compositions typically must be sterile and stable under the conditions of manufacture and storage. The composition can be formulated as a solution, microemulsion, liposome, or other ordered structure suitable for a desired concentration of the compound. In some embodiments, the carrier can be a solvent or dispersion medium including, but not limited to, water; ethanol; a polyol such as for example, glycerol, propylene glycol, liquid polyethylene glycol, and the like; and, combinations thereof. The proper fluidity can be maintained in a variety of ways such as, for example, using a coating such as lecithin, maintaining a required particle size in dispersions, and using surfactants.

In some embodiments, isotonic agents can be used such as, for example, sugars; polyalcohols that include, but are not limited to, mannitol, sorbitol, glycerol, and combinations thereof; and sodium chloride. Sustained absorption characteristics can be introduced into the compositions by including agents that delay absorption such as, for example, monostearate salts, gelatin, and slow release polymers. Carriers can be used to protect against rapid release, and such carriers include, but are not limited to, controlled release formulations in implants and microencapsulated delivery systems. Biodegradable and biocompatible polymers can be used such as, for example, ethylene vinyl acetate, polyanhydrides, polyglycolic acid, collagen, polyorthoesters, polylactic acid, polycaprolactone, polyglycolic copolymer, and the like. Such formulations can generally be prepared using methods known to one of skill in the art.

The compounds may be administered as suspensions or emulsions. Lipophilic solvents or vehicles include, but are not limited to, fatty oils such as, for example, sesame oil; synthetic fatty acid esters, such as ethyl oleate or triglycerides; and liposomes. Suspensions that can be used for injection may also contain substances that increase the viscosity of the suspension such as, for example, sodium carboxymethyl cellulose, sorbitol, or dextran. Optionally, a suspension may contain stabilizers or agents that increase the solubility of the compounds and allow for preparation of highly concentrated solutions.

In some embodiments, a therapeutically or prophylactically effective amount of a composition may range in concentration from about 0.01 nM to about 0.10 M; from about 0.01 nM to about 0.5 M; from about 0.1 nM to about 150 nM; from about 0.1 nM to about 500 µM; from about 0.1 nM to about 1000 nM, 0.001 µM to about 0.10 M; from about 0.001 µM to about 0.5 M; from about 0.01 µM to about 150 µM; from about 0.01 µM to about 500 µM; from about 0.01 µM to about 1000 nM, or any range therein. In some embodiments, the compositions may be administered in an amount ranging from about 0.005 mg/kg to about 100 mg/kg; from about 0.005 mg/kg to about 400 mg/kg; from about 0.01 mg/kg to about 300 mg/kg; from about 0.01 mg/kg to about 250 mg/kg; from about 0.1 mg/kg to about 200 mg/kg; from about 0.2 mg/kg to about 150 mg/kg; from about 0.4 mg/kg to about 120 mg/kg; from about 0.15 mg/kg to about 100 mg/kg, from about 0.15 mg/kg to about 50 mg/kg, from about 0.5 mg/kg to about 10 mg/kg, or any range therein, wherein a human subject is often assumed to average about 70 kg.

In some embodiments, the compounds can be administered by inhalation through an aerosol spray or a nebulizer that may include a suitable propellant such as, for example, dichlorodifluoromethane, trichlorofluoromethane, dichlorotetrafluoroethane, carbon dioxide, or a combination thereof. In one example, a dosage unit for a pressurized aerosol may be delivered through a metering valve. In another embodiment, capsules and cartridges of gelatin, for example, may be used in an inhaler and can be formulated to contain a powderized mix of the compound with a suitable powder base such as, for example, starch or lactose.

Rectal administrations can be made using any method known to one of skill. For example, a suppository formulation can be prepared by heating glycerin to about 120° C., combining the binding system with the heated glycerin, mixing the combination, adding purified water to a desired consistency, and pouring the desired consistency into a mold to form the suppository.

For topical administration, suitable formulations may include a biocompatible oil, wax, gel, powder, emulsion, polymer, or other liquid or solid carriers. Such formulations may be administered by applying directly to affected tissues. For example, a liquid formulation to treat infection of aural canal can be administered dropwise into the subject's ear. In another example, a hydrogel infused with the binding system can be applied to a burn. In another example, a cream formulation can be administered to an area of psoriasis. Transdermal administration includes percutaneous absorption of the composition through the skin. Transdermal formulations include patches, ointments, creams, gels, salves, and the like.

In some embodiments, the binding system is administered in a sustained release formulation, and the formulation can include one or more agents in addition to the binding system. In some embodiments, the sustained release formulations can reduce the dosage and/or frequency of the administrations of such agents to a subject. In some embodiments, an exogenous catalyst or enzyme is introduced to a target and one or more of the reactive oxygen species, phenolic compound, or the exogeneous catalyst or enzyme are segregated by encapsulation or micellation to delay the bioactivation until target site is reached by all components.

The amount of the compound administered may vary widely depending on the type of formulation, size of a unit dosage, kind of excipients, and other factors well known to those of ordinary skill in the art. The formulation may comprise, for example, from about 0.0001% to about 6% (w/w), from about 0.01% to about 1%, from about 0.1% to about 0.8%, or any range therein, with the remainder comprising the excipient or excipients.

In some embodiments, the composition can be administered in conjunction with at least one other therapeutic agent for the condition being treated. The amounts of the agents can be reduced, even substantially, such that the amount of the agent or agents desired is reduced to the extent that a significant response is observed from the subject. A significant response can include, but is not limited to, a reduction or elimination of nausea, a visible increase in tolerance, a faster response to the treatment, a more selective response to the treatment, or a combination thereof.

In some embodiments, the compounds, compositions, and formulations can be administered in combination with a composition taught herein using any amount, time, and method of administration known to be effective by one of skill. The compound can be administered, for example, in an amount ranging from about 0.1 µg/kg to about 1 mg/kg, from about 0.5 µg/kg to about 500 µg/kg, from about 1 µg/kg to about 250 µg/kg, from about 1 µg/kg to about 100 µg/kg from about 1 µg/kg to about 50 µg/kg, or any range therein. One of skill can readily select the frequency and duration of each administration.

In some embodiments, the methods taught herein can further include the administration of an effective amount of an additional bioactive agent or therapeutic treatment. In some embodiments, the terms "agent" and "therapy" can be interchangeable. In many embodiments, the molecular weight of an agent should be at or below about 40,000 Daltons to ensure elimination of the agent from a subject. In some embodiments, the molecular weight of the agent ranges from about 300 Daltons to about 40,000 Daltons, from about 8,000 Daltons to about 30,000 Daltons, from about 10,000 Daltons to about 20,000 Daltons, or any range therein.

Combinations therapies can be administered, for example, for 30 minutes, 1 hour, 2 hours, 4 hours, 8 hours, 12 hours, 18 hours, 1 day, 2 days, 3 days, 4 days, 5 days, 6 days, 7 days, 8 days, 9 days, 10 days, 2 weeks, 3 weeks, 4 weeks, 6 weeks, 3 months, 6 months 1 year, any combination thereof, or any amount of time considered necessary by one of skill. The agents can be administered concomitantly, sequentially, or cyclically to a subject. Cycling therapy involves the administering a first agent for a predetermined period of time, administering a second agent or therapy for a second predetermined period of time, and repeating this cycling for any desired purpose such as, for example, to enhance the efficacy of the treatment. The agents can also be administered concurrently. The term "concurrently" is not limited to the administration of agents at exactly the same time, but rather means that the agents can be administered in a sequence and time interval such that the agents can work together to provide additional benefit. Each agent can be administered separately or together in any appropriate form using any appropriate means of administering the agent or agents.

As described herein, a stabilized reagent pair can be administered for aqueous transport to a target site. In some embodiments, the reagent pair comprises a tannin having a molecular weight ranging from about 500 Daltons to about 4000 Daltons; and, hydrogen peroxide. The hydrogen peroxide can be hydrogen bonded to the tannin at a tannin:peroxide weight ratio that ranges from about 1:1000 to about 10:1; the binding system can be bioactivated at a target site having an oxidoreductase enzyme; and, the binding molecule binds to the target site. In some embodiments, a pharmaceutical formulation comprising a reagant pair taught herein can be used in an administration, and a pharmaceutically acceptable excipient. The tannin can comprise a catechin, and the tannin:peroxide ratio can ranges from about 1:10 to about 1:50. In some embodiments, the oxidoreductase can comprise a peroxidase; and, there can be no, or substantially no, unbound hydrogen peroxide in the formulation.

Articles of Manufacture

The present invention provides for articles of manufacture that encompass finished, packaged and labelled products. The articles of manufacture include the appropriate unit dosage form in an appropriate vessel or container such as, for example, a glass vial or other container that is hermetically sealed. In the case of dosage forms suitable for oral administration, the active ingredient, e.g. one or more agents including a dosage form taught herein, may be suitable for administration orally, rectally, vaginally, or the like. Alternatively, the unit dosage form may be a solid suitable for oral, transdermal, topical or mucosal delivery.

In some embodiments, the unit dosage form is suitable for oral or topical delivery. Thus, the invention encompasses solutions, which are preferably stable or substantially stable, sterile, and suitable for such administrations. The concentration of agents and amounts delivered are included as described herein.

As with any such product, the packaging material and container are designed to protect the stability of the product during storage and shipment. In addition, the articles of manufacture can include instructions for use or other information material that can advise the user such as, for example, a physician, technician or patient, regarding how to properly administer the composition as a prophylactic, therapeutic, or ameliorative treatment of the disease of concern. In some embodiments, instructions can indicate or suggest a dosing regimen that includes, but is not limited to, actual doses and monitoring procedures.

In some embodiments, the instructions can include informational material indicating how to administer the binding systems for a particular use or range of uses, as well as how to monitor the subject for positive and/or negative responses to the binding systems.

In some embodiments, the articles of manufacture can comprise one or more packaging materials such as, for example, a box, bottle, tube, vial, container, sprayer, insufflator, intravenous (I.V.) bag, envelope, and the like; and at least one unit dosage form of an agent comprising an extract taught herein within the packaging material. In some embodiments, the articles of manufacture may also include instructions for using the composition as a prophylactic, therapeutic, or ameliorative treatment for the disease of concern.

In some embodiments, the articles of manufacture can comprise one or more packaging materials such as, for example, a box, bottle, tube, vial, container, sprayer, insufflator, envelope, and the like; and a first composition comprising at least one unit dosage form of an agent comprising a binding system as taught herein within the packaging material, along with a second composition comprising a second agent such as, for example, any other bioactive agent that may be administered in combination with the binding system, or any prodrugs, codrugs, metabolites, analogs, homologues, congeners, derivatives, salts, solvates, and combinations thereof. In some embodiments, the articles of manufacture may also include instructions for using the composition as a diagnostic, prophylactic, therapeutic, or ameliorative treatment for the condition of concern.

In some embodiments, the article of manufacture can include a substantially anhydrous binding system. For example, a kit can be assembled which includes the anhydrous binding system comprising an anhydrous tannin with instructions combining the tannin with and an anhydrous reactive species generating component that forms a therapeutically, prophylactically, or nutritionally useful composition upon hydration.

Without intending to be limited to any theory or mechanism of action, the following examples are provided to further illustrate the teachings presented herein. It should be appreciated that there are several variations contemplated within the skill in the art, and that the examples are not intended to be construed as providing limitations to the claims.

EXAMPLE 1

Making a Binding System of Hydrolysable Tannin Bound to Hydrogen Peroxide and Showing a Stable, or Substantially Stable, Binding Pair Chinese Gall is an excellent source of a hydrolysable tannin. Chinese Gall (GALLAE CHINENSES from the *Rhus semialata* galls), contains 60% to 75% tannic acids and 2% to 4% of gallic acid. Gall extracts characteristically do not contain significant flavanoids. The polygalloyl glucoses or polygalloyl quinic acid esters presenting 2-12 gallate residues with a relatively open and conformable steric arrangement are favorable for forming stable multiple hydrogen bonds with hydrogen peroxide.

In this experiment, 1 to 10 grams a serial different quantity of gallotannic acid from Chinese. Gall (Sigma-Aldrich Chinese Gall) was dissolved in 20 cc of 35% food grade hydrogen peroxide. Comparisons of oxidizing potential were made colorimetrically using WATERWORKS peroxide check strips (Industrial Test Systems, Inc., Rock Hill, S.C.). The solution was desiccated by heating at 80° C. until the solution was a dark highly viscous mass. Half of the solution was reconstituted to its original volume. After 2 hr equilibration time. measurement of oxidative potential of this solution showed less than 10% difference from pre-dessicated state, indicating preferential binding. A minimum molar ratio of $H_2O_2$ to tannin compounds required to retain greater than 90% of $H_2O_2$ potential was used to define an optimal ratio. We find that this minimum molar ratio varies significantly with the choice and/or combination of phenolic compounds.

The other half of the solution was placed in cold temperature (ice bath) until a precipitate formed. After centrifuging and removing 50 cc of liquid containing the precipitate from the solution and returning the samples to room temperature, the balance of the solution showed significantly lower peroxide concentration than can be accounted for by the fluid volume removed. Adding back the 50 cc liquid containing the precipitate restored free peroxide levels to original levels, clearly indicating the incorporation of a high concentration of hydrogen peroxide on the precipitate.

EXAMPLE 2

Comparing Binding Systems Using a Hydrolysable Tannin, a Condensed Tannin, a Mixture of Hydrolysable and Condensed Tannins, and Resveratrol Bound to Hydrogen Peroxide to Compare the Binding Pairs Hydrolysable Tannin—For this example, the Chinese gall of Example 1 was used as the hydrolysable tannin, in addition to the following:

Condensed Tannin—Green tea (*Camilla Sinensis*) extract contains catechins and other flavanoid compounds but characteristically does not contain significant tannic acid content. Multiple gallate and catechol residues of various catechin and flavanol dimmers, trimers oligomers and polymers are favorable structures for stable hydrogen peroxide aggregate formation, though the flavan structure is more likely to cause steric blocking than the gallotannic structure.

Mix of Hydrolysable and Condensed Tannin—Pomegranate POMx (*Punica granatum* L., POM Wonderful brand) extract of fruit residue after pressing containing 86.0% ellagitannins, The approximate distribution of polyphenols is 19% ellagitannins as punicalagins and punicalins, 4% free ellagic acid, and 77% heterogenous oligomers of gallic acid, ellagic acid, and glucose with 2-8 phenol moieties. The planar structure of the punicaligins and the generally high number of gallate residues on the ellagitannins provide abundant opportunities for stable hydrogen perhydration.

Resveratrol from polygonum cuspidatum (NutraBio 99.87%—standardized to 50% active trans-resveratrol) a stilbenoid monomer with only three hydroxyls and low water solubility (0.003 g/l). It has a low binding site ratio of 0.013. Monomers, and lower molecular weight phenolics with separated hydroxyl groups such as resorcinol moieties are unfavorable structures for stable perhydrate formation.

In order to compare the samples provided above, a test series was prepared in 30 ml tubes containing from 1 g~10 g of the above extracts of Chinese Gall, Green Tea, Pomegranate and Resveratrol. Each was dissolved in 20 ml of 35% hydrogen peroxide then separate to two aliquots. One part was heated at 80° C. to a dark viscous semi-liquid and allowed to desiccate to a final volume of 5 ml. Each was rehydrated and serially diluted to detection range. Hydrogen peroxide colorimetric strips showed qualitatively different concentrations of hydrogen peroxide were retained by the different types of polyphenolic compounds.

Chinese gall and pomegranate extracts showed the highest peroxide retention capability, green tea extracts also showed good retention (approximately ½) and the resveratrol showed relatively less ability to form stable perhydrates. The results support the hypothesized molecular characteristics for formation of useful binding systems.

The other aliquot of was placed in an ice bath to precipitate the binding systems. After centrifuging and removing the precipitate to a separate tube and re-dissolved in 10 ml of water, the material went into solution, but the initial level of oxidation was surprisingly below detection limits. Measurements taken every 10 minutes showed a gradual increase of oxidation, reaching equivalence to the other aliquot after approximately 50 minutes. This was determined using WATERWORKS peroxide check strips (Industrial Test Systems, Inc., Rock Hill, S.C.). This demonstrates that the binding systems are not covalent complexes and can also be used as a timed release medium.

EXAMPLE 3

Data Showing Enzyme Selectivity and Targetting

A key aspect of the invention is that polyphenol-hydrogen peroxide aggregates are generally nonreactive with digestive enzymes such as proteases and peptidases that split proteins into their monomers, the amino acids, lipases that split fat into three fatty acids and a glycerol molecule, carbohydrases that split carbohydrates such as starch and sugars into simple sugars, or nucleases hat split nucleic acids into nucleotides.

Binding systems responding to target specific enzymes exhibit orders of magnitude (500× or more) differential between active and passive states providing focused toxin binding, pathogen or damage specific effects with a reduction in undesirable collateral effects. In the animal body, the activated binding systems can actively form glycosydic bonds, as well as complex proteins and amino acids. The binding of the phenolic compound to, for example, glucuronic acid or other glucose moieties can neutralize the activity of lipopolysaccharides and other important toxins.

In this experiment, first, a serial dilution of a binding system of Chinese Gall-hydrogen peroxide (from 0 to 10 µg/ml) was incubated with a lipopolylsaccharide, then reacted with standard polymixin B with and without horseradish peroxidase at 37° C. The result showed that, when combined with horseradish peroxidase, the Chinese Gall-hydrogen peroxide binding system exhibited over 500× increase in lipopolysaccharide binding compared to the composition without horseradish peroxidase as determined by ELISA measurements of polymixin B binding inhibition test.

Next, we performed an anti-cholera toxin B antibody binding inhibition experiment. A serial dilution of a binding system of Chinese Gall-hydrogen peroxide (from 0 to 10 µg/ml) was combined with cholera toxin, then reacted with anti-cholera toxin B antibody with and without horseradish peroxidase at 37° C. The result showed that the combination of horseradish peroxidase and the Chinese Gall-hydrogen peroxide binding system exhibited over 500× increase over the composition without the peroxidase in anti-cholera toxin B antibody binding as determined by ELISA measurements.

These results clearly demonstrate a surprising and extraordinarily efficient binding of two distinctly different toxins upon enzyme activation. The large differential in activity indicates the viability of delivering a stable polyphenol perhydrate for localized and aggessive remote activation by tissues, tissue conditions, or pathogens that express peroxidase enzymes or other site specific enzymes utilizing hydrogen peroxide or its decomposition products as a reaction promoting substrate.

EXAMPLE 4

Data Showing that an Increase in Bound $H_2O_2$ on Chinese Gall Results in a Higher Inhibitory Activity of the Chinese Gall Sample A, which contained 100 mg of Chinese gall (Sigma Aldrich, Chinese Gall) dissolved in 100 ml of 10% hydrogen peroxide, then diluted to a total volume of 1000 ml was compared against Sample B, which contained 1 mg of Chinese gall dissolved in 100 ml of 0.1% hydrogen peroxide (a dilution of the 10% hydrogen peroxide by 100×) and was then also diluted to 1000 ml. Due to the dilution, the molarity of the diluted hydrogen peroxide was 1/100 of the sample A solution, such that 100× less $H_2O_2$ was available to bind with the Chinese gall. It was suspected that a proportionally lower amount of $H_2O_2$ would be bound on Sample A as compared to Sample B. To compare the relative effects of the different amounts of available $H_2O_2$, the activity of the two binding systems was compared using a binding assay. Sample A had a higher inhibition effect, showing that the higher amount of available $H_2O_2$ resulted in a higher activity of the phenolic compound in the binding system.

EXAMPLE 5

Data Showing Treatment of Diarrhea

Data has shown that the binding systems can protect, improve, maintain or restore body homeostasis, especially gastrointestinal health. The binding systems provide anti-secretory, anti-infective, anti-pathogenic, anti-adhesion, anti-allergenic and anti-toxin functions; as well as promote a localized tissue barrier formation, tissue healing, gross permeability reduction, astringency, and a restoration of hemeostasis.

This example illustrates how the binding systems can restore gastrointestinal health through these overlapping damage specific functions to synergistically defeat pathogen defenses without involving typical antibiotic resistance mechanisms. The binding system was shown to provide a highly effective resolution of infections and the disruption of homeostasis caused by a microbial diarrhea.

In a double blind test, 86 human subjects suffering from moderate to severe acute diarrhea. The subjects were given either a binding system or placebo on the first day, and then the opposite on the next day. The binding system contained less than 5 milligram dry weight equivalent of a binding system of a mixture of pomegranate and green tea extracts with hydrogen peroxide. The time to resolution (last loose stool) was 7 hours with a P<0.06. 43% of the subjects receiving active product on the first day had no further loose stools after single dose. Most subjects also reported rapid cessation of discomfort symptoms.

This example shows that the binding systems can treat digestive health conditions associated with pathogen colonization, toxins, overgrowth of bacteria (dysbiosis) or fungal organisms (*Candida*).

EXAMPLE 5

Data Showing Treatment of a Chronic *Candida Albicans* Infection with Related Symptoms A 42 year old Male with a diagnosed chronic *Candida Albicans* infection, or intestine expressing also as skin rashes, experienced significant reduction of both the rash and abdominal discomfort after 5 days of ingesting a pomegranate/green tea binding system with hydrogen peroxide. The symptoms gradually returned to original severity over 2 weeks after termination of regimen.

This example shows that the binding systems can not only treat a GI condition, but they can also reduce symptoms associated with the GI condition. Such symptoms can include, but are not limited to, inflammation, sepsis, allergic reaction, pain, cramping, intestinal spasms, stomach upset, acid irritation, diarrhea, constipation, bloating, nausea and fatigue.

EXAMPLE 6

Data Showing Treatment of GI Condition with Near-Immediate Relief 43 adults in a placebo-controlled 24 hr crossover study were given a 25 ml solution of a green tea/pomegranate binding system with hydrogen peroxide and observed for 2 hrs after ingestion. The subjects reported significant reduction in upper gastric acid discomfort, nausea, bloating and abdominal pain within 2 hrs of active ingestion vs no notable reduction on placebos. $P<0.05$ in all categories.

EXAMPLE 7

Data Showing Treatment of a Variety of GI Conditions

In a study of adult subjects given the binding system, the subjects reported benefits related to treatment of ulcers, fistulas, irritable bowel syndrome, acid reflux, food poisoning, inflammatory bowel diseases, food sensitivity, travelers diarrhea, dietary change, and physical agitation (i.e, agitation to GI track from running).

46 volunteer subjects not experiencing acute diarrhea, but experience frequent symptoms such as those in FIG. 6b though 6f (including 6 persons with diagnosed IBS or IBD) ingested the polyphenol/peroxide binding composition as needed for relief of symptoms. 78% reported significant benefit.

The success in such a wide variety of GI conditions suggests that the binding system may also be helpful in treating the GI symptoms and conditions related to the administration of chemotherapy and radiation therapy. Also, the binding systems would appear to be useful in the treatment of chronic gastrointestinal conditions including, but not limited to, colitis, irritable bowel syndrome, Crohn's disease, necrotic enteritis, functional colonic diseases, malabsorbtion, peptic ulcer, gastro-esophogeal reflux disease, ulcerative colitis, diverticulitis, and ameliorating their symptoms.

EXAMPLE 8

Data Showing Treatment of an Immune-Response GI Condition

The binding systems can efficiently bind, block, or neutralize inflammatory agents, as well as immune complements, antibodies and receptors. This activity facilatates modulating animal inflammatory response to biotic and abiotic factors, including reducing autoimmune activity. Bacteria can influence the phenomenon known as oral tolerance, in which the immune system is less sensitive to an antigen, including those produced by gut bacteria, once it has been ingested. This tolerance, mediated in part by the gastrointestinal immune system and in part by the liver, can induce a hyper-reactive immune response like those found in allergies and auto-immune disease.

Some suspect that inflammation in inflammatory bowel disease, for example, is due to increased permeability of the inner lining of the colon. This permeability may allow bacteria to invade the tissues and cause an immune reaction that leads to prolonged inflammation. Tissue damage in inflammatory bowel disease results from the immunological misperception of danger within the naturally occurring flora or a failure of normal tolerance to pathogenic bacteria. It is still unclear whether the inflammation that occurs is due to a specific subset of intestinal microbes or due to a problem with the tolerance of commensal gut flora. Abnormal leaky cellular junctions, which are supposed to prevent permeability, have been found in the cells of patients with inflammatory disease. Several studies have reported the inhibitory effect of green tea catechins. For example, epicatechin gallate (ECG) and eligallocatechin gallate (EGCG) can be incorporated into a binding system for oral or distal delivery to the intestinal tract to provide greater anti-inflammatory effect than EGCG or EGC alone.

In order to support this theory that the binding systems can treat such an immune response GI condition, several volunteers were treated. The volunteers experienced symptoms that suggested such an immune response problem. They had frequent painful lower abdominal pain, and they ingested a 1 milligram dry weight equivalent of a pomegranate/hydrogen peroxide binding system formulation for 5 consecutive days. All reported significant reduction in pain with a continuing effect lasting for 2-5 days after the last dose.

EXAMPLE 9

Data Showing Treatment of a GI Condition Relating to an Innate Immune Response Most allergy symptoms tie to the innate immune system. Sometimes the body over responds to allergens by releasing excess amounts of histamine, serotonin, prostaglandin, interleukins, etc causing allergy symptoms. Because of the structural and behavioral similarities of certain portions of these immune molecules to phenolic compounds or proteins, an enzyme activated binding system can have the potential to directly complex to, and inactivate, immune response compounds or inhibit their receptors.

In order to support this theory that the binding systems can treat such an innate immune response in the GI tract, several people with frequent food allergies were treated. The allergies related to gluten, dairy and unidentified compounds, and the subjects were expressing a variety of symptoms such as headaches, diarrhea, bloating, nausea, rash, or fatigue, anecdotally reported a consistent reduction or elimination of symptoms after ingestion of the binding system.

EXAMPLE 10

Data Showing Topical Treatment of a Dermal Wound

Without intending to be bound by any theory or mechanism of action, it is believed that the binding systems can facilitate the wound healing by at least two mechanisms. The first mechanism is the activation of binding system at the wounded tissue by the peroxidase from the damaged tissue. This activation will initiate the release of reactive oxygen and oxygen molecule to either damage the potential harmful pathogens at wounded site or initiate the crosslinking or binding function to neutralize the toxin and interfere with the pathogen's normal growth function to reduce the potential infection. The second mechanism is the rapid crosslinking of damaged tissue surface with a similar function to protein crosslinking mechanisms during the normal growth and healing process. The astringent effects and rapid formation of a refractory barrier by the binding system help to reduce fluid loss and act as a substrate for facilitate faster healing of the epithelial tissue.

In order to support this theory, a controlled wound healing test was done by providing 0 to 20 µg/ml of a perhydrated green tea extract directly to bilateral lancet wounds on the backs of nude mice. Sub-dermal healing was measured electronically using a BioelectricMed skin potential scanner and visual observation. The healing time was 3× lower than the healing time of comparison Neosporin treated wounds and equivalent to the healing time observed using a O2Cure hyperbaric oxygen emulsion.

To further support this theory, a 10 ug/mg solution of a green tea extract/peroxide binding system was applied by spraying twice daily to the injuries of a 62 year old man with full depth skin abrasions on calf and thigh. Exudate from the injuries substantially stopped within 12 hours. Epithelialization was 95% complete within 21 days, and a 3 month follow-up showed only minor discoloration, as well as normal hair follicles and skin texture.

To further support this theory, a 12 year old boy with a large $2^{nd}$ degree burn on his calf and a 9 year old girl with a $2^{nd}$ degree burn on her upper arm. Both subjects exhibited cessation of exudation from the burns within one day of application and unusually rapid epithelialization. The wounds healed without visible infection or scarring.

This experiment shows that the binding systems can facilitate the wound healing process for cuts, abrasions, and burns of dermal tissue.

EXAMPLE 11

Data Showing Topical Treatment of an Inflammatory Condition

The synergistic combination of antimicrobial, anti-inflammatory and tissue repair effects presented by direct or indirect application of the binding systems to compromised tissues have valuable application in correcting abnormal conditions on any dermal, epidermal tissue or mucosal tissue. These include inflammatory or autoimmune conditions of the alimentary canal, urinary tract, reproductive tract, respiratory tract, sinuses, aural canal, tear ducts, peritoneum and skin.

To illustrate the applicability of the binding systems to inflammatory conditions, anecdotal observation of complete and permanent resolution of long standing scaly psoriasis isolated to the legs and hands, face or scalp of 5 individuals after direct topical application of pomegranate/green tea extract binding system with hydrogen peroxide for 7 days. Twice daily, a spray of 20 ug/ml solution was administered and caused the scale to begin sloughing off within 2 days with significant reduction in itching. Within 5 days healthy skin with normal barrier function was emerging, and substantially complete resolution was observed in 7 days. The administration was terminated and a follow-up on all subjects showed complete restoration of normal skin with no visible indication or previous disorder. Similar results were observed upon application to skin sores, and abnormal skin areas of a number of domestic pets.

EXAMPLE 12

Data Showing How Maintaining a Healthy Digestive Tract in Animals Promotes Growth, Reduces the Mortality Rate, and Improves the General Health of the Animals The binding systems interact with animal digestive mucosa to promote healthy digestive function; provide prophylactic effect against intestinal infection; reduce incidence and duration or scour, improve fecal scores; reduce mortality rate; improve weight gain rate and feed/gain ratio; improve vigor; reduce fecal shedding of pathogens; and, reduce the effect of endotoxins. The binding system can be used as an alternative to animal production antibiotics, and particularly feed additives. The binding system has a method of action distinct from current antibiotics, making it useful against antibiotic resistant bacteria and unlikely to promote antibiotic resistance.

The effect of the binding systems on damaged gut tissue is to reduce irritation and inflammatory stimuli while providing protection against further assaults until compromised tissue is healed. As such, the use of the binding systems is an efficient strategy for improving feed conversion ratios without the use of antibiotics. A healthy digestive tract remains available for maximum nutritional uptake. In comparison, appetite and immune system stimulating additives can be counterproductive to feed conversion maximization. Moreover, the convention wisdom is that the use of tannin compounds in effective quantities in animal feeds is counter-nutritional. The following represents surprising results to those of ordinary skill in the art.

FIGS. 1A and 1B illustrate the surprising results of adding the binding system to the drinking water of piglets, according to some embodiments. In FIG. 1A, a binding system of green tea 50/50 extract/pomegranate in a 1:10 ratiohydrogen peroxide was introduced in drinking water to weaned piglets to achieve a target dosage of 2 ug total dry-plant weight equivalent per kg animal weight). After 5 weeks, the supplemented animals cumulatively gained 26% more weight during the period than controls. FIG. 1B shows 93 pre-weaned piglets receiving the same target dosage in drinking water provides reduced mortality by over 40% and improved stool scores.

Other experiments were performed on other animals to see if the results would be obtained in a different species. Several hundred free range chickens were fed antibiotic free diets that were supplemented with a similar relative quantity of the binding system. The supplement reduced the variation in individual animal weight, improved stool consistency, and again reduced mortality over a control flock.

EXAMPLE 13

Data Showing In Vitro Microbiologic Performance

FIG. 2 shows the minimal inhibitory concentration (MIC) tests for a composition of 50/50 pomegranate-green tea extract binding system with hydrogen peroxide at a ratio of 10:1 for the hydrogen peroxide:plant compound (molar wt/dry wt). compared to the MIC for other common antimicrobial compounds taken from published data, according to some embodiments. The binding system has very strong antimicrobial activity, having MIC levels similar to the most potent of industrial biocides (Kathon). Moreover, the performance of the binding system is notably consistent against the gram positive and the gram negative bacteria. It's worthy to note that all of the compounds have very different chemistry and modes of action. All are relatively slow acting bacteriostatic compounds, and it's important to emphasize that only RIFAXAMIN and the binding system are intended for human consumption. The MIC range of the binding system is also significantly times lower than MIC for hydrogen peroxide alone.

The binding system is a 50/50 pomegranate-green tea binding system with hydrogen peroxide at a ratio of 10:1 for the hydrogen peroxide:phenolic compound (dry wt/dry wt). The binding system has very strong antimicrobial activity, having MIC levels similar to the most potent of industrial biocides (Kathon). Moreover, the performance of the binding system is notably consistent against the gram positive and the gram negative bacteria. It's worthy to note that all of the compounds have very different chemistry and modes of action. All are relatively slow acting bacteriostatic compounds, and it's important to emphasize that only RIFAXAMIN and the binding system are intended for human consumption. RIFAXAMIN performed poorly compared to the binding system.

FIG. 3 shows the binding system's the effective inhibition of a broad spectrum of bacteria by the binding system, according to some embodiments. The binding system of FIG. 2 was used in this example, and the selection of bacteria represent different classes of pathogens including gram positive and gram negative types. Similar results were obtained with several different formulations using green tea extract, pomegranate extract and combinations thereof. The system showed that 3-23 ug/ml of plant extract to water was the minimal inhibitory concentration against the entire range of bacteria. One of skill will also appreciate that this again shows a very low concentration is needed to be effective as an antimicrobial. The identical performance of the binding system between the non-resistant and resistant staphylococcus strains is an indication that the mechanism of action is unlike that of antibiotics. Legend: the '+' indicates visible growth in broth culture (turbidity), the '−' indicates no growth (no turbidity), and the MIC falls within the first '+'.

FIG. 4 shows effective reduction of virus maintaining the host cell culture viability, according to some embodiments. The binding system of FIG. 2 was used in this example, and this figure indicates that the binding system is not dependent on cellular metabolism and is able to kill a virus.

Figure 5A:
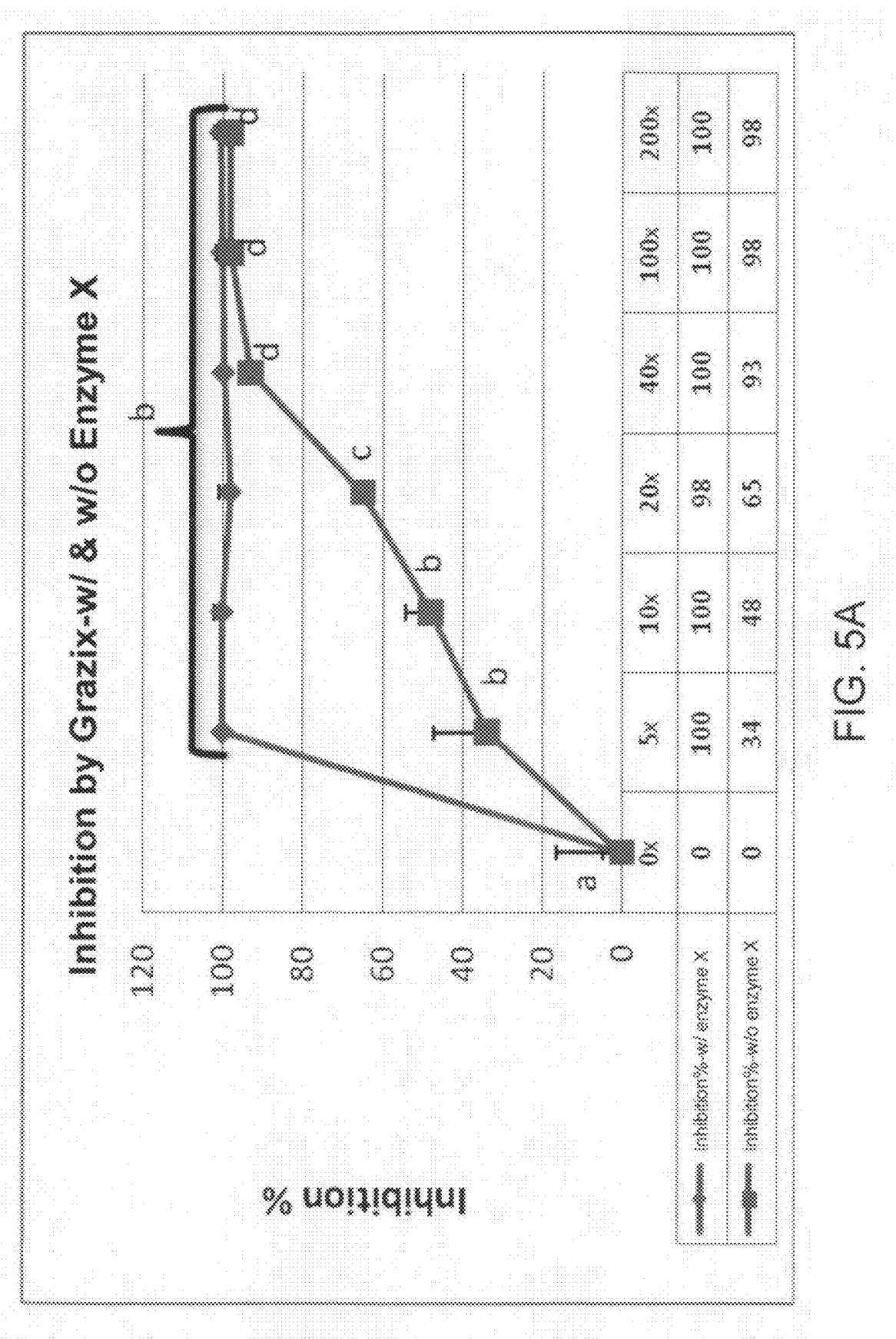
Figure 5B:
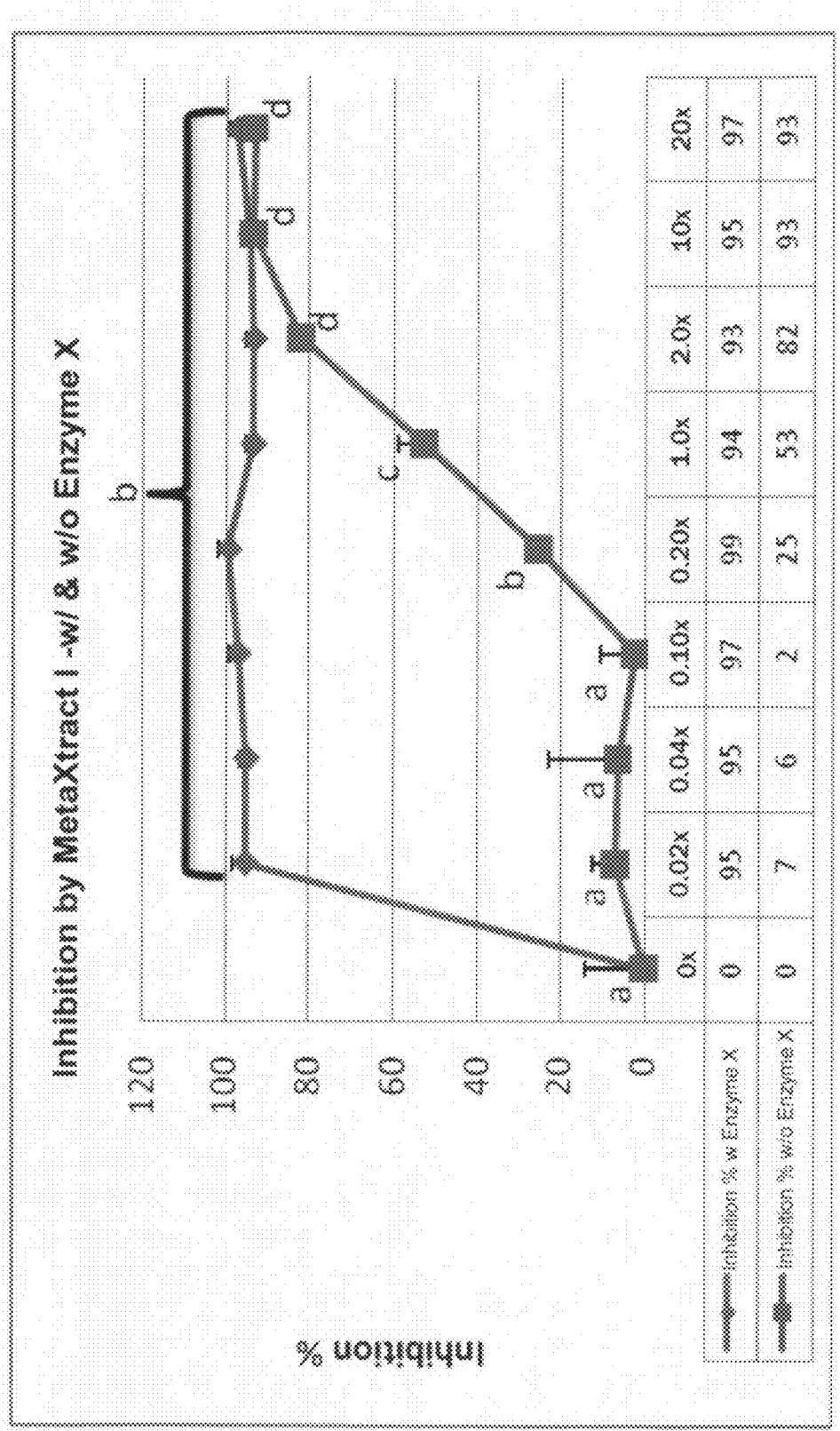

FIGS. 5A and 5B are studies showing significant elevation of polymixin B inhibition, according to some embodiments. The binding system of FIG. 2 was used in this example, and this figure shows that when horseradish peroxidase is added to the binding system, effectiveness on both lipopolysaccharide endotoxin, a common food poisoning toxin, and the cholera exotoxin, a typical protein-based bacterial toxin, indicating the ability to inactivate a wide range of pathogen virulence factors responsible for tissue damage, inflammation and other undesirable physiologic effects. As such, this is an in vitro demonstration of the increased activation effect of the enzymes on the binding system. It also shows the highly effecting binding on a range of toxins, a lipopolysaccharide (has no protein structure but, rather a glucose structure) and a protein structure, the endotoxin.

FIGS. 6A and 6F show the rapid resolution of acute watery diarrhea in 86 subjects, according to some embodiments. The study is a crossover study of 86 people from ages 2 and up with acute watery diarrhea and shows rapid reduction in duration compared to a placebo group which received treatment 24 hours later. The time scale is last time to watery or unformed stool.

In FIG. 6A, it can be seen that upon receiving a single 1.125 mg dose of the binding system either on the first day or second day, the mean time to the last unformed stool was 7 hours for the subjects. FIG. 6B through 6F show significant reduction of various secondary symptoms in the same study as FIG. 6A. in FIG. 6B, heartburn and indigestion symptoms in patients with acute infectious diarrhea were rapidly reduced in duration compared to a placebo group which received treatment 24 hours later. In FIG. 6C, nausea symptoms in patients with acute infectious diarrhea were significantly reduced compared to a placebo group which received treatment 24 hours later. In FIG. 6D, vomiting symptoms in patients with acute infectious diarrhea were significantly reduced compared to placebo group which received treatment 24 hours later. In FIG. 6E, abdominal pain in patients with acute infectious diarrhea were significantly reduced compared to a placebo group which received treatment 24 hours later. In FIG. 6F, bloating in patients with acute infectious diarrhea were significantly reduced compared to a placebo group which received treatment 24 hours later.

Although these symptoms are associated with pathogen induced acute diarrhea, those skilled will recognize that some of these symptoms are typical of many chronic gastrointestinal conditions such as irritable bowel syndrome (IBS), inflammatory bowel diseases (IBD) and gastroesophogeal reflux disease. Based on the highly effective amelioration of such systems by the polyphenol/peroxide binding system, it is reasonable to expect similar benefits to those suffering these other gastrointestinal conditions.

It should be appreciated that the experimental conditions and components provided herein are for illustration and example only. One of skill can vary the experimental conditions and components to suit a particular or alternate experimental design. The experimental conditions can be in vitro or in vivo, or designed for any subject, for example, human or non-human. For example, animal testing can be varied to suit a desired experimental method.

We claim:

1. A method of treating a damaged mucosal, or gastrointestinal tissue, the method comprising: administering an effective amount of a composition to the damaged tissue of a subject in need thereof, the composition comprising hydrogen peroxide and a mixture of an aqueous pomegranate extract and an aqueous green tea extract wherein the mixture comprises phenolic compounds; wherein the composition is prepared by combining the mixture with hydrogen peroxide to form an aqueous solution such that the final concentration of hydrogen peroxide in the solution is 0.05-3%;
   the mixture to hydrogen peroxide ratio in the composition is about 1:2 to about 1:20 on a molar weight basis;
   the hydrogen peroxide is releasably bound to the phenolic compounds of the mixture;
   the composition is bioactivated at a target site having a peroxidase or oxidase that is expressed in response to the tissue damage; and
   the composition contains no unbound hydrogen peroxide prior to the bioactivating at the target site;
   wherein the composition functions as an antitoxin when bioactivated at the target site of the damaged mucosal, or gastrointestinal tissue and assists in the healing of the damaged tissue by inactivating toxic compounds at the target site.

2. The method of claim 1, wherein the mixture comprises a flavanol.

3. The method of claim 1, wherein the mixture comprises a catechin.

4. The method of claim 1, wherein the mixture comprises gallic acid, epigallic acid, or a combination thereof.

5. The method of claim 1, wherein the damaged tissue is mucosal tissue.

6. The method of claim 1, wherein the damaged tissue is gastrointestinal tissue.

* * * * *